US011685960B2

(12) United States Patent
Cho et al.

(10) Patent No.: US 11,685,960 B2
(45) Date of Patent: Jun. 27, 2023

(54) RAPID NUCLEIC ACID DETECTION WITHOUT SAMPLE PREPARATION

(71) Applicant: CROSSLIFE TECHNOLOGIES INC., Carlsbad, CA (US)

(72) Inventors: HyunDae Cho, Carlsbad, CA (US); Yuanyuan Wu, Carlsbad, CA (US); Jarred Yasuhara-Bell, Carlsbad, CA (US)

(73) Assignee: CROSSLIFE TECHNOLOGIES INC., Carlsbad, CA (US)

( * ) Notice: Subject to any disclaimer, the term of this patent is extended or adjusted under 35 U.S.C. 154(b) by 364 days.

(21) Appl. No.: 16/868,403

(22) Filed: May 6, 2020

(65) Prior Publication Data

US 2020/0354800 A1   Nov. 12, 2020

Related U.S. Application Data

(60) Provisional application No. 62/844,917, filed on May 8, 2019.

(51) Int. Cl.
*C12Q 1/6862* (2018.01)
*C12Q 1/70* (2006.01)
*G01N 33/543* (2006.01)

(52) U.S. Cl.
CPC ........... *C12Q 1/701* (2013.01); *C12Q 1/6862* (2013.01); *C12Q 1/702* (2013.01); *G01N 33/54366* (2013.01); *C12Q 2600/156* (2013.01); *C12Q 2600/178* (2013.01); *G01N 2333/11* (2013.01); *G01N 2333/16* (2013.01); *G01N 2800/26* (2013.01)

(58) Field of Classification Search
CPC ........... C12Q 1/6862; C12Q 2525/155; C12Q 2525/191; C12Q 2565/625; C12Q 1/701; C12Q 2523/109; C12Q 2533/107; C12Q 2563/179
See application file for complete search history.

(56) References Cited

U.S. PATENT DOCUMENTS

| 8,323,888 | B2 | 12/2012 | Mirkin |
| 10,626,447 | B2 | 4/2020 | Cho et al. |
| 2008/0124810 | A1 | 5/2008 | Terbrueggen |
| 2010/0099574 | A1 | 4/2010 | Moon |
| 2014/0094383 | A1 | 4/2014 | Lee et al. |
| 2016/0266118 | A1 | 9/2016 | Cho et al. |
| 2019/0106729 | A1 | 4/2019 | Pel et al. |

OTHER PUBLICATIONS

Abe et al., "Rapid DNA Chemical Ligation for Amplification of RNA and DNA Signal," Bioconjugate Chem., vol. 19, pp. 327-333. (Year: 2008).*
Jou et al., "Deletion Detection in the Dystrophin Gene by Multiplex Gap Ligase Chain Reaction and Immunochromatographic Strip Technology," Human Mutation, vol. 5, pp. 86-93. (Year: 1995).*
Daher et al., "Recombinase Polymerase Amplification for Diagnostic Applications," Clinical Chemistry, vol. 62, No. 7, pp. 947-958. (Year: 2016).*
Maruyama et al., "Chemical ligation of oligonucleotides using an electrophilic phosphorothioester," Nucleic Acids Reserach, vol. 45, No. 12, pp. 7042-7048. (Year: 2017).*
Maruyama et al., Chemical Ligation Of Oligonucleotides Using An Electrophilic Phosphorothioester, Nucleic Acids Research, vol. 45, No. 12, pp. 7042-7048, 2017.
International Search Report and Written Opinion dated Aug. 13, 2020 in International Application No. PCT/US2020/031726.
Alexander et al., Multicentre Prospective Study On Dengue Classification In Four South-East Asian And Three Latin American Countries, Tropical Medicine & International Health, vol. 16, No. 8, pp. 936-948, 2011.
Andresen et al., High Sensitivity Of A Rapid Immunochromatographic Test For Detection Of Influenza A Virus 2009 H1N1 In Nasopharyngeal Aspirates From Young Children, Journal of Clinical Microbiology, vol. 48: pp. 2658-2659, 2010.
Blacksell et al., Commercial Dengue Rapid Diagnostic Tests For Point-Of-Care Application: Recent Evaluations And Future Needs?, Journal Of Biomedicine And Biotechnology, vol. 2012, No. 151968, 2012.
Blacksell et al., Comparison Of Performance Of Serum And Plasma In Panbio Dengue And Japanese Encephalitis Virus Enzyme-Linked Immunosorbent Assays, The American Society of Tropical Medicine and Hygiene, vol. 87, No. 3, pp. 573-575, 2012.
Blacksell et.al., Comparison Of Seven Commercial Antigen And Antibody Enzyme-Linked Immunosorbent Assays For Detection Of Acute Dengue Infection, Clinical And Vaccine Immunology, vol. 19, No. 5, pp. 804-810, 2012.
CDC, Evaluation of Rapid Influenza Diagnostic Tests For Detection Of Novel Influenza A (H1N1) Virus—United States, Morbidity and Mortality Weekly Report, vol. 58, pp. 826-829, 2009.
CDC, Performance Of Rapid Influenza Diagnostic Tests During Two School Outbreaks Of 2009 Pandemic Influenza A (H1N1) virus infection—Connecticut, Morbidity and Mortality Weekly Report, vol. 58: pp. 1029-1032, 2009.
Chan et al., Analytical sensitivity of rapid influenza antigen detection tests for swine-origin influenza virus (H1N1), Journal of Clinical Virology—Elsevier, vol. 45, pp. 205-207, 2009.

(Continued)

*Primary Examiner* — Young J Kim
(74) *Attorney, Agent, or Firm* — Knobbe, Martens, Olson & Bear LLP

(57) ABSTRACT

Sensitive and specific detection of nucleic acids can be achieved using a chemical ligation-based template assisted rapid assay (TARA-L) with simple chemical reactions between probes and without the need for enzymes. Probes are designed to form a ligation product when they anneal to adjacent portions of a target nucleic acid. The ligation products can be detected, such as in immunochromatographic assays. The methods allow for the fast, efficient analysis of biological samples for the presence of nucleic acids and can be used, for example, in point of care settings.

28 Claims, 34 Drawing Sheets

Specification includes a Sequence Listing.

(56) References Cited

OTHER PUBLICATIONS

Chen et al., Consecutive Signal Amplification for DNA Detection Dased on De Novo Fluorophore Synthesis and Host-Guest Chemistry, Angewandte Chemie, vol. 51, pp. 4479-4483, 2012.
Ellis et al., Evaluation of Four Real-Time PCR Assays For Detection Of Influenza A(H1N1) Viruses, Eurosurveillance, vol. 14, No. 22, pii: 19230, 2009.
Faix et al., Rapid-test Sensitivity For Novel Swine-Origin Influenza A (H1N1) virus in humans, The New England Journal of Medicine, vol. 361, pp. 728-729, 2009.
Ganzenmueller et al., Comparison Of The Performance Of Direct Fluorescent Antibody Staining, A Point-Of-Care Rapid Antigen Test And Virus Isolation With That Of RT-PCR For The Detection Of Novel 2009 Influenza A (H1N1) Virus In Respiratory Specimens, Journal of Medical Microbiology, vol. 59, pp. 713-717, 2010.
Grossmann et al., Achieving Turnover in DNA-Templated Reactions, Angewandte Chemie, vol. 47, pp. 7119-7122, 2008.
Grossmann et al., DNA-catalyzed transfer of a reporter group, Journal of the American Chemical Society, vol. 128, pp. 15596-15597, 2006.
Grossmann et al., Target-Catalyzed Transfer Reactions for the Amplified Detection of RNA, Angewandte Chemie, vol. 47, No. 37, pp. 7119-7122, 2008.
Gryaznov et al., Template Controlled Coupling And Recombination Of Oligonucleotide Blocks Containing Thiophosphoryl Groups, Nucleic Acids Research, vol. 21, No. 6, pp. 1403-1408, 1993.
Guan et al., Molecular Epidemiology of H5N1 Avian Influenza, Revue Scientifique Et Technique, vol. 28, No. 1, pp. 39-47, 2009.
Guzman et.al., Dengue: a continuing global threat, Nature Reviews Microbiology, vol. 8, 12 Suppl:S7-16, 2010.
Halstead et al., Observations Related To Pathogenesis Of Dengue Hemorrhagic Fever. IV. Relation Of Disease Severity To Antibody Response And Virus Recovered, Yale Journal Of Biology And Medicine, vol. 42, pp. 311-328, 1970.
Hawkes, et al., Sensitivity Of Rapid Influenza Diagnostic Testing For Swine-Origin 2009 A (H1N1) Influenza Virus In Children, Pediatrics, vol. 125, pp. e639-644, 2010.
Hunsperger et al., Evaluation of Commercially Available Anti-Dengue Virus Immunoglobulin M tests, Emerging Infectious Diseases, vol. 15, pp. 436-440, 2009.
Hurt et al., Performance Of Influenza Rapid Point-Of-Care Tests In The Detection Of Swine Lineage A(H1N1) influenza viruses, Influenza and Other Respiratory Viruses, vol. 3, pp. 171-176, 2009.
Karre et al., Comparison of Becton Dickinson Directigen EZ Flu A+B test against the CDC real-time PCR assay for detection of 2009 pandemic influenza A/H1N1 virus, Journal of Clinical Microbiology, vol. 48, No. 1, pp. 343-344, 2010.
Kok et al., Comparison Of A Rapid Antigen Test With Nucleic Acid Testing During Cocirculation Of Pandemic Influenza A/H1N1 2009 And Seasonal Influenza A/H3N2, Journal of Clinical Microbiology, vol. 48, pp. 290-291, 2010.
Levy-Bruhl et al., Modified surveillance of influenza A(H1N1) virus infections in France, Eurosurveillance, 2009.
Li et al., DNA-Catalyzed Polymerization†, Journal of the American Chemical Society, vol. 124, pp. 746-747, 2002.
Luebke et al., Nonenzymatic Ligation Of Oligodeoxyribonucleotides On A Duplex DNA Template By Triple-Helix Formation, Nucleic Acids Research, vol. 20, No. 12, 3005-3009, 1992.
MacKay et al., Real-time PCR In Virology, Nucleic Acids Research, vol. 30, pp. 1292-1305, 2002.
Marshall et al., DNA Chips: An Array Of Possibilities, Nature Biotechnology, vol. 16, No. 1, pp. 27-31, 1998.
Martina et al., Dengue Virus Pathogenesis: An Integrated View, Clinical Microbiology Reviews, vol. 22, pp. 564-581, 2009.
Metelev, et al., Oligodeoxyribonucleotides with Internucleotidic or Terminal Phosphorothioate Groups: Different Pathways in the Reaction with Water-Soluble Carbodhmide, Nucleosides & Nucleotides, vol. 18, pp. 2711, 1999.
Parida et al., Rapid detection and differentiation of dengue virus serotypes by a real-time reverse transcription-loop-mediated isothermal amplification assay, Journal of Clinical Microbiology, vol. 43, No. 6, pp. 2895-2903, 2005.
Peeling et al., Evaluation of Diagnostic Tests: Dengue, Nature Reviews Microbiology, vol. 8, 12 Suppl:S30-8, 2010.
Peiris et al., Emergence of a Novel Swine-Origin Influenza A Virus (S-OIV) H1N1 virus In Humans, Journal of Clinical Virology—Elsevier, vol. 45, No. 3, pp. 169-173, 2009.
Rubin et al., Convergent DNA synthesis: A Non-Enzymatic Dimerization Approach To Circular Oligodeoxynucleotides, Nucleic Acids Research, vol. 23, No. 17, pp. 3547-3553, 1995.
Santiago et.al., Analytical and clinical performance of the CDC real time RT-PCR Assay For Detection And Typing Of Dengue Virus, PLOS Neglected Tropical Diseases, vol. 7, No. 7, 2013.
Shabarova et al., Chemical ligation of DNA: The First Non-Enzymatic Assembly Of A Biologically Active Gene, Nucleic Acids Research, vol. 19, No. 15, pp. 4247-4251, 1992.
TDR/WHO. "Evaluation of commercially available antidengue virus immunoglobulin M tests." Diagnostics Evaluation Series No. 3 [online] <http://apps.who.int/ tdr/publications/tdr-research-publications/diagnostics evaluation- 3/pdf/diagnostics evaluation-3.pdf> (TDR/WHO, Geneva. Switzerland, 2009).
TDR/WHO. Dengue diagnostics: Proceedings of an international workshop Oct. 4-6, 2004. [online] <http://apps.who.int/tdr/publications/tdrresearch- publications/dengue-diagnosticsproceedings/pdf/dengue_diagnostics.
Teoh et al., Detection of dengue viruses using reverse transcription-loop-mediated isothermal amplification, BMC Infectious Diseases, vol. 13, No. 387, 2013.
Uyeki et al., Diagnostic testing for 2009 pandemic influenza A (H1N1) Virus Infection In Hospitalized Patients, The New England Journal of Medicine, vol. 361, pp. e114, 2009.
Van Der Vries et al., Satisfying The Need For Rapid Diagnosis Of New Variant Influenza A H1N1, Expert Review of Molecular Diagnostics, vol. 3, pp. 251-253, 2010.
Vasoo et al., Rapid Antigen Tests For Diagnosis Of Pandemic (Swine) influenza A/H1N1, Clinical Infectious Diseases, vol. 49, No. 7, pp. 1090-1093, 2009.
Vázquez et al., Templated Native Chemical Ligation: Peptide Chemistry Beyond Protein Synthesis, Journal of Peptide Science, 2014.
Waggoner et al., Development Of An Internally Controlled Real-Time Reverse Transcriptase PCR Assay For Pan-Dengue Virus Detection And Comparison Of Four Molecular Dengue Virus Detection Assays, Journal of Clinical Microbiology, vol. 51, No. 7, pp. 2172-2181, 2013.
Waggoner et.al., Comparison of the FDA-approved CDC DENV-1-4 Real-Time Reverse Transcription-PCR With A Laboratory-Developed Assay For Dengue Virus Detection And Serotyping, Journal Of Clinical Microbiology, vol. 51, No. 10, pp. 3418-3420, 2013.
World Health Organization (2009) Statement to the press by WHO Director—General Dr Margaret Chan. Available: http://www.who.int/mediacentre/ news/statements/2009/h1n1_pandemic_phase6_20090611/en/index.html. Accessed on Aug. 15, 2009.
World Health Organization, Dengue: Guidelines For Diagnosis, Treatment, Prevention And Control, WHO Press, Geneva, Switzerland, 2009.
Xu et al., Chemical And Enzymatic Properties Of Bridging 5'-S-Phosphorothioester Linkages in DNA, Nucleic Acids Research, vol. 26, No. 13, pp. 3159-3164, 1998.
Xu et al., Nonenzymatic Autoligation In Direct Three-Color Detection of RNA and DNA Point Mutations, Nature Biotechnology, vol. 2, pp. 148-152, 2001.
Xu et al., Novel 5'-Iodonucleoside Allows Efficient Nonenzymatic Ligation of Single-stranded and Duplex DNAs, Tetrahedron Lett, vol. 38, No. 32, pp. 5595-5598, 1997.
Zhang et al., MicroRNAs And Their Regulatory Roles In Animals And Plants, Journal of Cellular Physiology, vol. 210, No. 2, pp. 279-289, 2007.

\* cited by examiner

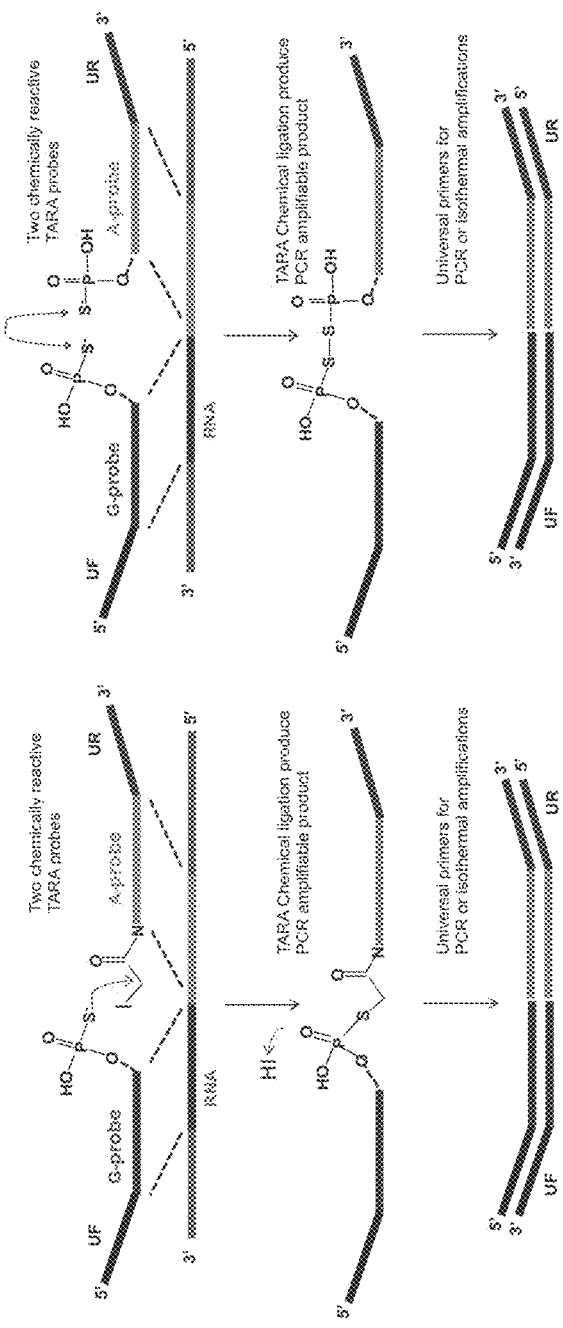

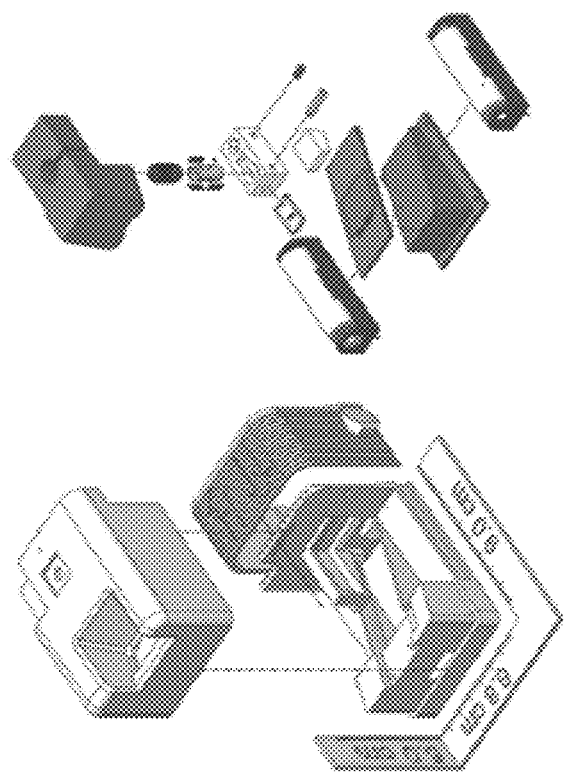
Figure 4C
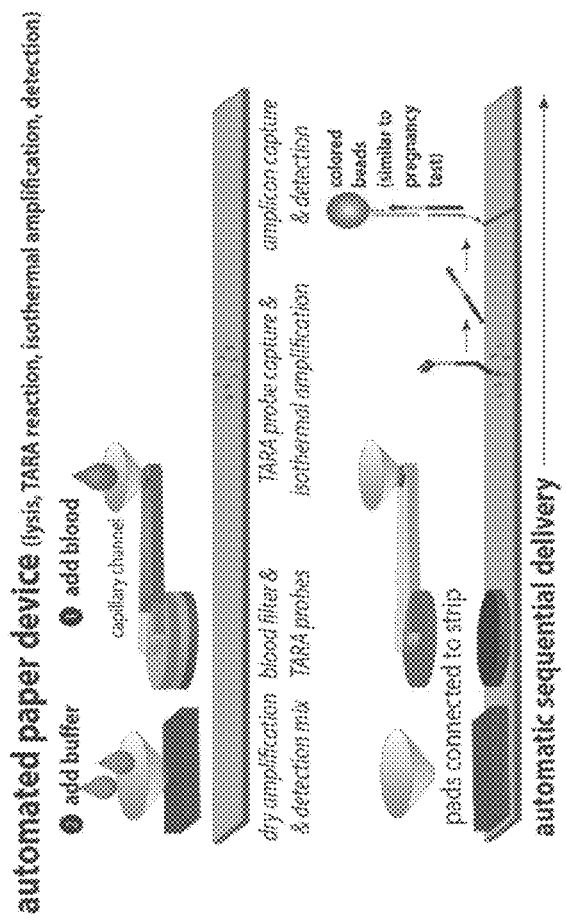
Figure 4A
Figure 4B

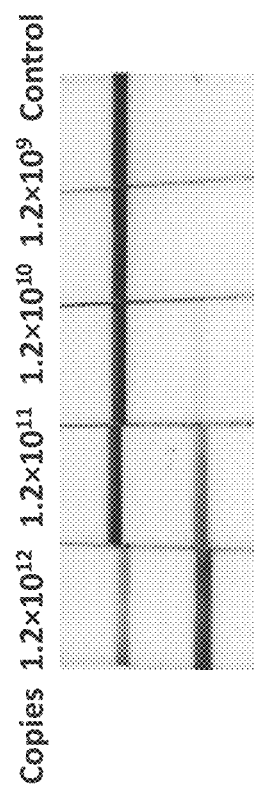
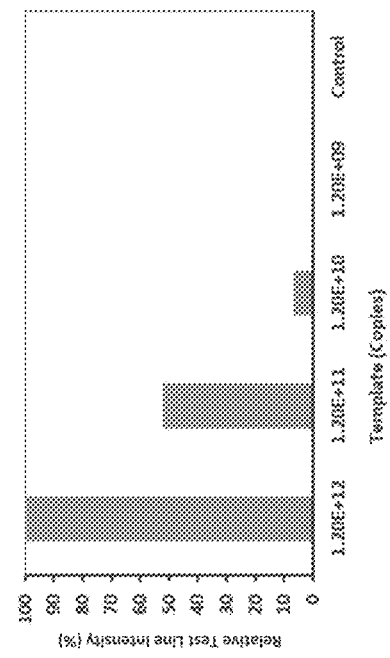
Figure 15A
Figure 15B

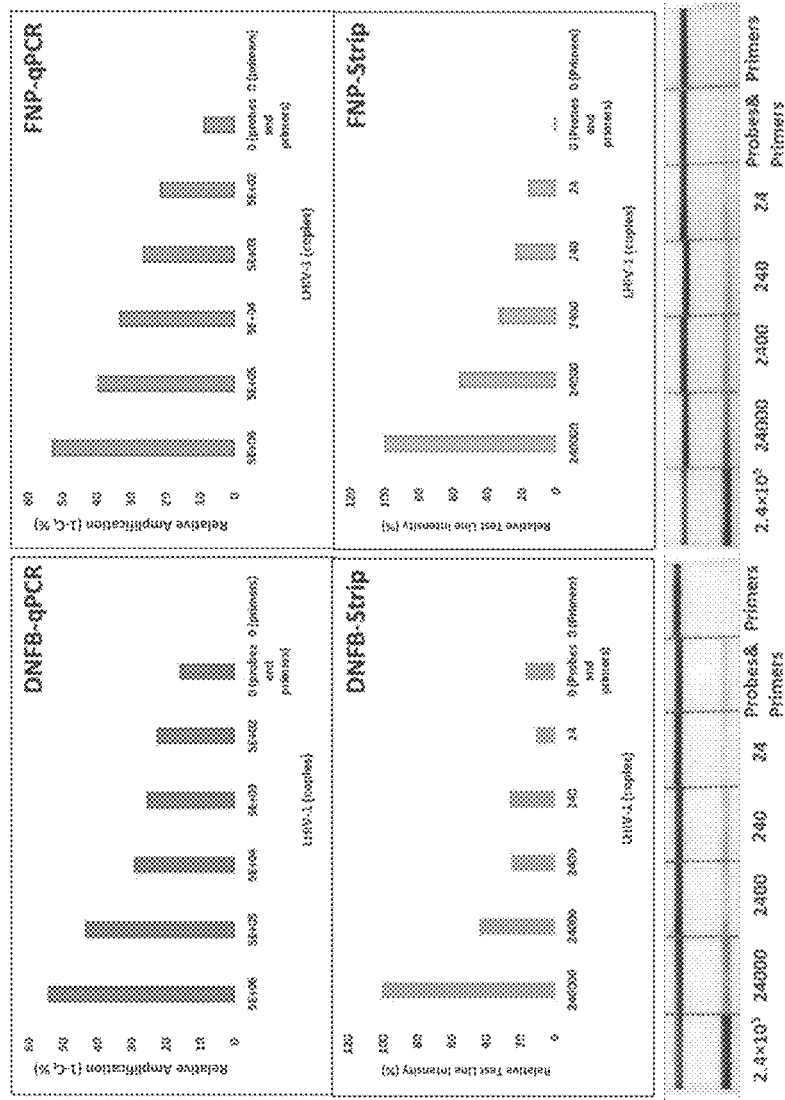

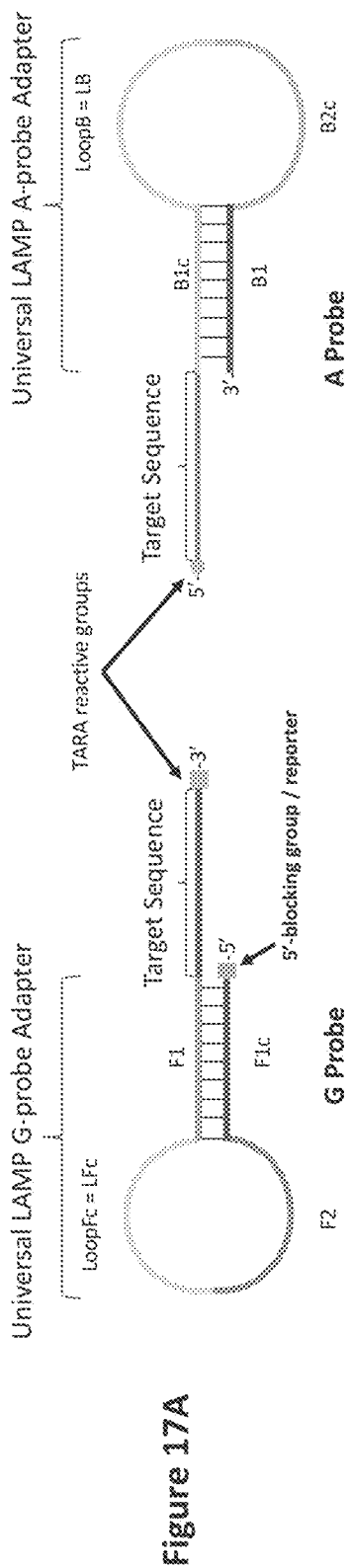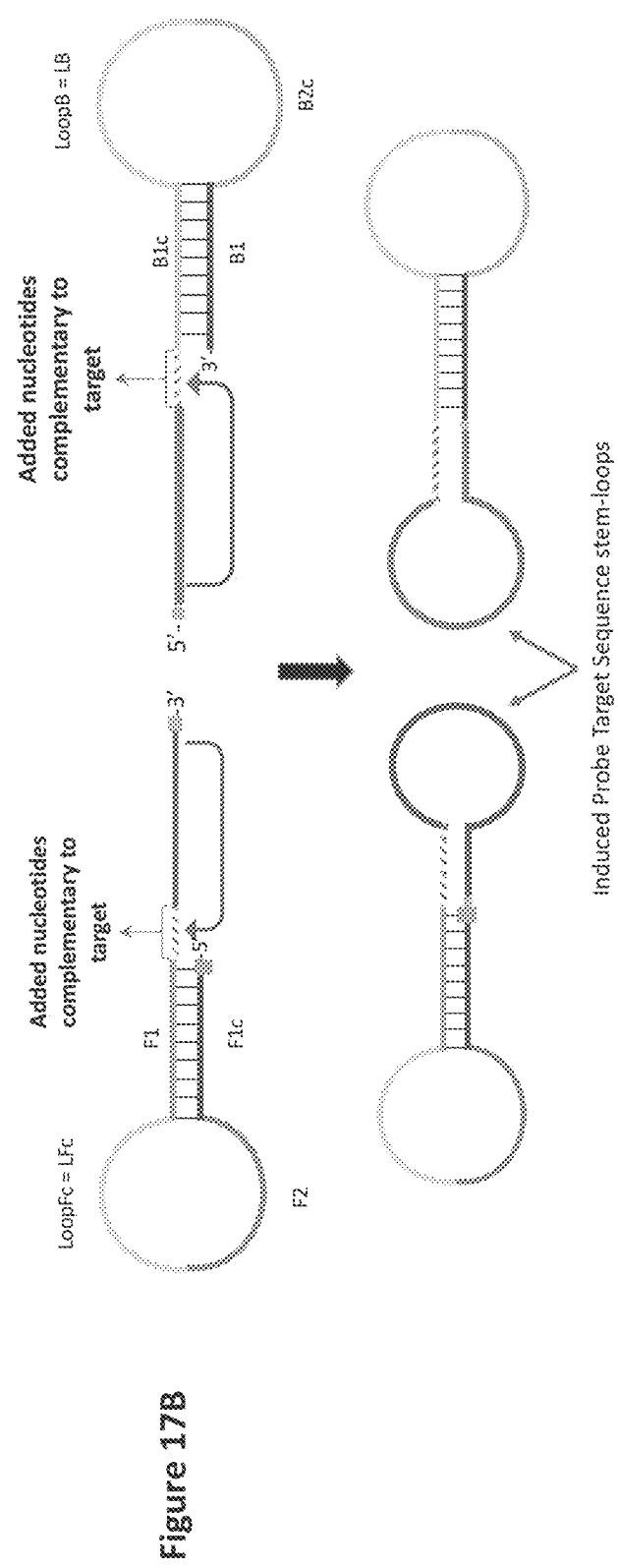
Figure 17A
Figure 17B

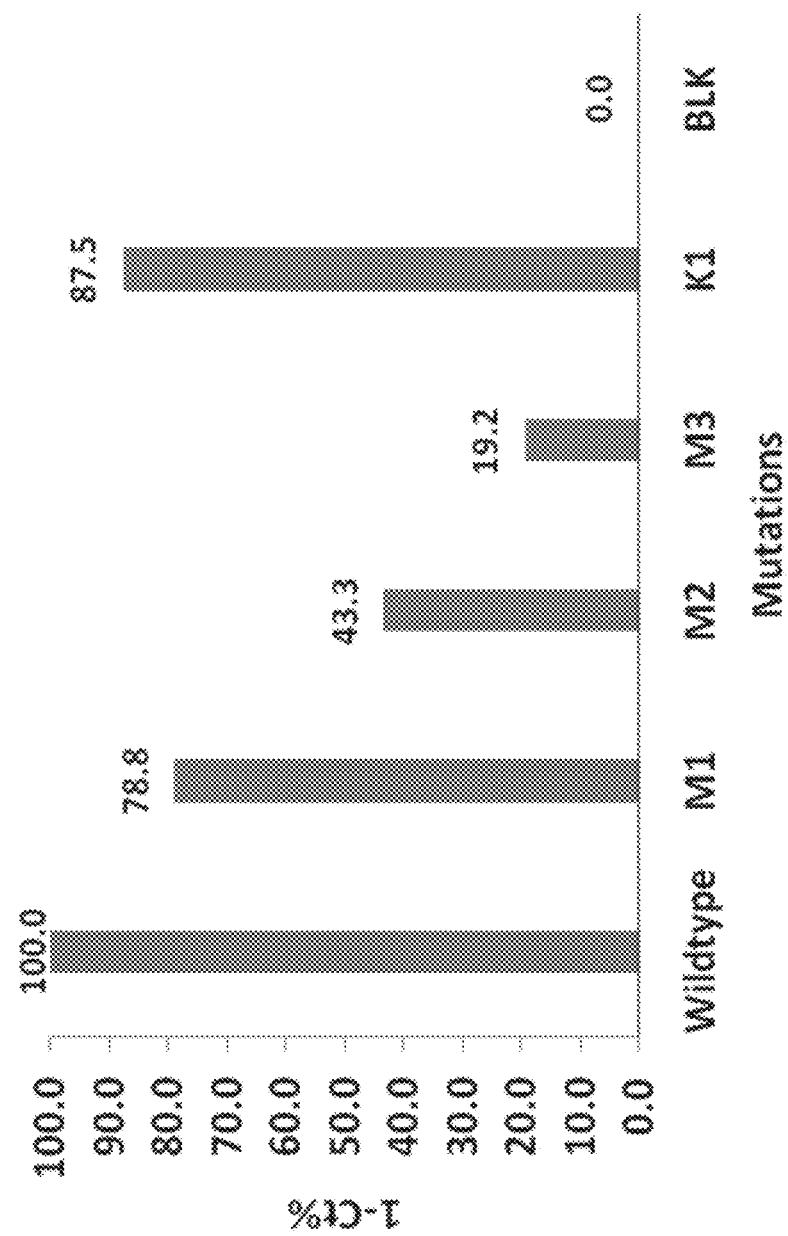

RAPID NUCLEIC ACID DETECTION WITHOUT SAMPLE PREPARATION

PRIORITY AND CROSS REFERENCE TO RELATED APPLICATIONS

This application claims the benefit of U.S. Provisional Application 62/844,917 filed on May 8, 2019, which is hereby incorporated by reference in its entirety.

SEQUENCE LISTING IN ELECTRONIC FORMAT

The present application is being filed along with an Electronic Sequence Listing as an ASCII text file via EFS-Web. The Electronic Sequence Listing is provided as a file entitled CLIFE002ASEQLIST.txt, created and last saved on May 6, 2020, which is 11,898 bytes in size. The information in the Electronic Sequence Listing is incorporated herein by reference in its entirety.

BACKGROUND

Field

The present disclosure is related to methods, kits, and devices for rapid nucleic acid detection.

Description of the Related Art

Molecular diagnostics is a collection of techniques that apply molecular biology to medical testing. Molecular diagnostics can be used to diagnose and monitor diseases, detect disease risks, and also offers the prospect of personalized medicine, which has been widely applied to fields such as prenatal screening, disease treatment, infectious disease diagnostics, disease risk management, and cancer risk assessment. However, many molecular diagnostics methods are dependent on an enzyme-based system, such as PCR or RT-PCR techniques that increase the number of nucleic acid molecules and amplify the target sequences in a patient sample, and typically require complex instrumentation and a trained technician.

SUMMARY

In some embodiments, methods of determining the presence of a target nucleic acid in a sample are provided. The methods can be used, for example, to diagnose the presence of a disease or disorder in a subject, where the presence of a target nucleic acid in a sample taken from the subject is indicative of the disease or disorder. In some embodiments the methods can be used to identify the presence of a pathogen, parasite or other organism in a sample.

In some embodiments, methods of determining the presence of a target nucleic acid in a sample comprise contacting the sample with a reaction mixture comprising an activator and at least one set of chemically-reactive probes. The at least one set of chemically-reactive probes comprises a plurality of a first probe comprising a first nucleic acid region that is complementary to a first part of the target nucleic acid sequence and a first chemical group at a 3' end of the first nucleic acid sequence, and a plurality of a second probe, the second probe comprising a second nucleic acid region complementary to a second, different part of the target nucleic acid sequence and a second, different chemical group at a 5' end. The first and second parts of the target nucleic acid sequence may be separated by 10 nucleotides or less, for example by 1, 2, 3, 4, 5, 6, 7, 8, or 10 nucleotides. In some embodiments the first and second parts of the target nucleic acid sequence are directly adjacent to each other, with no intervening nucleotides. In the presence of the target nucleic acid in the sample the first probe and second probe anneal to the first and second parts of the target nucleic acid sequence and the first and second chemical groups are brought into proximity of each other. The first and second chemical groups are selected such that when in proximity and in the presence of the activator they ligate together through a chemical ligation reaction between the first chemical group and the second chemical group to form a chemically ligated product. The chemically ligated product can be detected, for example by capturing and visualizing the chemically ligated product on an immunochromatographic test strip. Detection of the chemically ligated product indicates the presence of the target nucleic acid in the sample.

In some embodiments, the first chemical group is a thiophosphate group. In some embodiments, the second chemical group is a primary amine.

In some embodiments, the chemical ligation reaction comprises activation of the first chemical group or the second chemical group by the activator and ligation of the activated first chemical group or the activated second chemical group to the second chemical group or the first chemical group, respectively, in the presence of the target nucleic acid.

In some embodiments, the activator is selected from the group consisting of 2-Fluoro-5-nitropyridine (FNP), 1-Fluoro-2,4-dinitrobenzene (FDNB), 1-Fluoro-2,4,6-Trinitrobenzene (FNTB) and succinimidyl iodoacetate (SIA).

In some embodiments, the first part and the second part of the target nucleic acid sequence are substantially adjacent to each other in the target nucleic acid sequence.

In some embodiments of the method of determining the presence of a target nucleic acid in a sample, the sample is contacted with the reaction mixture at a temperature of 50 to 60° C.

In some embodiments, detecting the chemically ligated product by capturing and visualizing the chemically ligated product on an immunochromatographic test strip is performed at room temperature within 5 to 10 min of contacting the sample with the reaction mixture.

In some embodiments, the sample comprises a nasal swab, nasal aspirate, oropharyngeal swab, urine, sweat, tears, lymph, plasma, serum, saliva, semen, cerebrospinal fluid, synovial fluid, or blood.

In some embodiments the sample is contacted with one, two, three or more additional sets of chemically reactive probes. For example, one or more additional set of chemically reactive probes may be configured to ligate in the presence of a different target nucleic acid sequence. In some embodiments one or more additional sets of chemically reactive probes are configured to anneal to different parts of the same target nucleic acid as the first set of chemically reactive probes.

In some embodiments, the target nucleic acid sequence is not amplified prior to contacting the sample with the reaction mixture.

In some embodiments, the chemically ligated product may be amplified prior to detecting the chemically ligated product, such as by capturing and visualizing the chemically ligated product on an immunochromatographic test strip.

In some embodiments, the ligated product may be amplified by one or more of TARA-L-PCR, TARA-L-RPA, and TARA-L-LAMP.

In some embodiments, the chemically ligated product is amplified by an isothermal amplification process, such as by loop-mediated isothermal amplification (LAMP) or recombinase-polymerase amplification (RPA).

In some embodiments, the first and second probes further comprise universal primer sequences, specific primer sequences, or both. In some embodiments, the first and second probes further comprise universal or specific adapter sequences. In some emodiments, the adapter sequences comprise at least one barcode sequence.

In some embodiments, the first probe comprises an adapter sequence that is blocked at the 5' end with a blocking group. In some embodiments, the blocking group is selected from a group consisting of Biotin, FITC, FAM, phosphate, and C3-spacer.

In some embodiments, the universal or specific primers sequences are located 5' to the first nucleic acid region of the first probe and 3' to the second nucleic acid region of the second probe.

In some embodiments at least one of the first and second probes comprises a reporter molecule. In some embodiments both the first and second probes each comprise a reporter. In some embodiments, the reporter is configured for detection, product capture, multiplexing, or a combination thereof. In some embodiments, the reporter may comprise, for example, Biotin, FITC, FAM or digoxin.

Methods of diagnosing a condition in a subject are also provided. The subject may be, for example, a patient believed to be or at risk of suffering from the disease or disorder to be diagnosed. In some embodiments, the methods may comprise obtaining a sample from the subject that may comprise a target nucleic acid associated with the condition. The presence of the target nucleic acid in the sample can be used to diagnose the condition. The sample is contacted with a reaction mixture comprising at least one set of chemically reactive probes. The at least one set of probes comprises a plurality of a first probe comprising a first nucleic acid region that is complementary to a first part of the target nucleic acid sequence and a first chemical ligation group, such as a thiophosphate group, at a 3' end. The set of probes also comprises a plurality of a second probe, the second probe comprising a second nucleic acid region complementary to a second, different part of the target nucleic acid sequence and a second chemical ligation group at a 5' end, such as a primary amine group. The first and second chemical ligation groups are selected such that when they are brought into proximity of each other under appropriate conditions, the first and second probes are chemically ligated to each other through reaction of the first and second chemical ligation groups. The reaction mixture may also comprise an activator, that activates one or both of the first and second chemical ligation groups, facilitating the ligation when the groups are in proximity to each other. In some embodiments the activator is selected from the group consisting of 2-Fluoro-5-nitropyridine (FNP), 1-Fluoro-2,4-dinitrobenzene (FDNB), 1-Fluoro-2,4,6-Trinitrobenzene (FNTB) and succinimidyl iodoacetate (SIA). In some embodiments the first part and the second part of the target nucleic acid sequence are separated by 0 to 10 nucleotides. In some embodiments the first part and second part of the target nucleic acid sequence are directly adjacent. In the presence of the target nucleic acid sequence the first and second products anneal to the target nucleic acid and the chemical ligation groups are brought into proximity of each other such that the first and second primers are ligated to each other to form a chemically ligated product. In some embodiments first and second primers are ligated through a reaction between a thiophosphate group and a primary amine group to form a chemically ligated product. Following sufficient time to allow for the annealing and ligation, any chemically ligated product is detected. In some embodiments the chemically ligated product is detected by immunochromatographic analysis. Detection of the chemically ligated product diagnoses the condition in the subject.

In some embodiments, the target nucleic acid is from or related to infection with a pathogen. In some embodiments the target nucleic acid is from or related to the presence of a bacterium, fungus, virus, or parasite.

In some embodiments, the target nucleic acid is from or related to a virus selected from the group consisting of dengue virus, influenza virus, chikungunya virus, the human immunodeficiency virus (HIV), the hepatitis C virus (HCV), human papillomavirus (HPV), Middle East respiratory syndrome (MERS) virus, arboviruses, respiratory syncytial virus (RSV; also known as human orthopneumovirus), coronavirus, and Ebola virus.

In some embodiments, the target nucleic acid is from or related to a bacterium selected from the group consisting of methicillin-resistant *Staphylococcus aureus* (MRSA).

In some embodiments, the target nucleic acid is from or related to a parasite such as *Plasmodium falciparum* (malaria), *Candida auris* and Opisthorchiid liver flukes consisting of *Opisthorchis sinensis* (also known as *Clonorchis sinensis*), *Opisthorchi viverrini* or *Opisthorchis felineus*.

In some embodiments of the method of diagnosing a condition in a subject, the target nucleic acid is selected from the group consisting of RNA and DNA. In some embodiments the target nucleic acid is microRNA.

In some embodiments, the sample comprises a nasal swab, nasal aspirate, oropharyngeal swab, urine, sweat, tears, lymph, plasma, serum, saliva, semen, cerebrospinal fluid, synovial fluid, or blood.

In some embodiments, a kit for detecting the presence of a target analyte in a sample, such as for diagnosing a condition in subject, is provided. In some embodiments, a kit comprises a reaction mixture comprising at least one set of chemically-reactive probes. The at least one set of chemically-reactive probes may comprise a plurality of a first probe (G probe) and a second probe (A probe). In some embodiments the reaction mixture also comprises an activator. The first probe may comprise a first chemical group at a 3'end, and a first nucleic acid region that is complementary to a first part of a target nucleic acid sequence. The second probe may comprise a second chemical group at a 5'end, and a second nucleic acid region complementary to a second, different part of the target nucleic acid sequence. In some embodiments a distance between the first part and the second part of the target nucleic acid sequence is from 0 to 10 nucleotides. The first probe and the second probe are configured to ligate by a chemical ligation reaction between the first chemical group and the second chemical group in the presence of the target nucleic acid sequence to generate a chemically ligated product. The presence of the chemically ligated product can then be used to confirm the presence of the target analyte in the sample. The chemically ligated product can be detected, for example, with immunochromatographic strips coated with test and control line reagents that bind the chemically ligated product and allow for its visualization.

In some embodiments the target analyte is associated with a pathogen selected from a group consisting of bacteria, fungi, viruses, and parasites. For example, the virus may be one selected from the group consisting of dengue virus, influenza virus, chikungunya virus, the human immunodeficiency virus (HIV), the hepatitis C virus (HCV), human papillomavirus (HPV), Middle East respiratory syndrome (MERS) virus, arboviruses, respiratory syncytial virus (RSV; also known as human orthopneumovirus), coronavirus, and Ebola virus. In some embodiments the target analyte is associated with methicillin-resistant *Staphylococcus aureus* (MRSA). In some embodiments the target analyte is associated with a parasite such as *Plasmodium falciparum* (malaria), *Candida auris* and Opisthorchiid liver flukes consisting of *Opisthorchis sinensis* (also known as *Clonorchis sinensis*), *Opisthorchi viverrini* or *Opisthorchis felineus*.

In some embodiments the target nucleic acid comprises RNA or DNA. In some embodiments the target nucleic acid comprises microRNA.

In some embodiments a sample is selected from the group consisting of nasal swab, nasal aspirate, oropharyngeal swab, urine, sweat, tears, lymph, plasma, serum, saliva, semen, cerebrospinal fluid, synovial fluid, and blood. In some embodiments the sample is a liquid sample. In some embodiments a sample is dissolved in or suspended in liquid for analysis.

In some embodiments of the kit for diagnosing a condition in a subject, the first chemical group is a thiophosphate group. In some embodiments of the kit for diagnosing a condition in a subject, the second chemical group is a primary amine.

In some embodiments of the kit for diagnosing a condition in a subject, the activator is selected from the group consisting of 2-Fluoro-5-nitropyridine (FNP), 1-Fluoro-2,4-dinitrobenzene (FDNB), 1-Fluoro-2,4,6-Trinitrobenzene (FNTB) and succinimidyl iodoacetate (SIA).

In some embodiments, a set of chemically-reactive nucleic acid probes is provided. The set of chemically-reactive nucleic acid probes may comprise a plurality of a first probe (G probe), the first probe comprising a first chemical group at a 3'end, a first nucleic acid region that is complementary to a first part of a target nucleic acid sequence, and a first LAMP adapter, and a plurality of a second probe (A probe), the second probe comprising a second chemical group at a 5'end, a second nucleic acid region complementary to a second, different part of the target nucleic acid sequence, and a second LAMP adapter, wherein each of the first and second LAMP adapters comprise a first stem region, a first loop region, a second loop regions and a second stem region, wherein the first stem region and second stem region are complementary to, and configured to bind to each other.

In some embodiments, each of the first and second probes further comprises a sequence between the first nucleic acid region and second nucleic acid region, respectively, wherein the sequence in the first probe is complementary to, and configured to bind to, a portion of the first nucleic acid region and the sequence in the second probe is complementary to, and configured to bind to, a portion of the second nucleic acid region.

In some embodiments, each of the first and second LAMP adapters further comprising a barcode sequence between the first loop region and the second loop region, wherein the barcode sequence in the first LAMP adapter is complementary to, and configured to bind to, the barcode sequence in the second LAMP adapter.

BRIEF DESCRIPTION OF THE DRAWINGS

FIGS. 1A-1E show schematics of embodiments of chemical ligation-based Template Assisted Rapid Assay (TARA-L).

FIG. 1A illustrates embodiments of 2-Fluoro-5-Nitropyridine (FNP)-based TARA.

FIG. 1B illustrates embodiments of 1-Fluoro-2,4,6-Trinitrobenzene (FTNB)-based TARA.

FIG. 1C illustrates embodiments of 1-Fluoro-2,4-Dinitrobenzene (FDNB)-based TARA.

FIG. 1D illustrates embodiments of Succinimidyl iodoacetate (SIA)-based TARA.

FIG. 1E illustrates embodiments of Thiophosphate (PS)-based TARA.

FIGS. 4A-4C show examples of a design of the TARAplex device and components according to some embodiments.

FIG. 4A shows an example of a test having dry reagents stored in the cartridge that are released upon test activation by the sequential addition of sample and buffer. In some embodiments on-board heaters heat the sample tube where a sample such as the illustrated blood is added (for example at 95° C., 2 min) and the reaction zone, illustrated as the TAA probe capture and isothermal amplification region (for example at 60° C., depending on the amplification method selected). In some embodiments ligated TARA probes are captured, and sample/CLBuffer are followed downstream by amplification mix. In some embodiments, a buffer wash prior to amplification can be included by adding a "blank" pad to the device.

FIG. 4B shows an example of how in some embodiments, after applying the sample to the pads, as illustrated in FIG. 4A, a mechanical system such as a slider can be used to connect the reagent pads to the test strip to initiate sequential delivery to the reaction zone and capture and detection portions of the test strip. This can be done passively in a 1DPN device as illustrated.

FIG. 4C shows a TARAplex device including a buffer syringe and paper strip, a housing with a slider (center), and heaters for the swab tube and paper reaction zone (right). All processes from sample input, for example blood input, to detection can be integrated into a simple cartridge with heaters. In some embodiments a single buffer port can be used to distribute buffer to dry reagent pads.

FIG. 7A shows the results of the time test for SIA chemistry. TARA-ligation tests were run as 50-μl reactions containing 0.4 μM probes and template. TARA-ligation reactions took place at 55° C. and were 'stopped' at various time points by mixing samples 1:1 v:v with 'STOP' solution (95% formamide, 5 mM EDTA and 0.25 mg/ml bromophenol blue) and heating at 95° C. for 5 min. Reactions were loaded onto a 16% SDS-PAGE gel at 30 μl per well. TARA-L reactions were stopped at 0, 10 s, 30 s, 1 min, 5 min, 10 min, 15 min, 20 min, 30 min, 45 min, and 60 min. A TARA-L no-template control was also included and reacted for 60 min. Results show that ligation can occur as quickly as 10 s.

FIG. 7B shows the percent ligation vs. time. Gel analysis was performed using ImageJ to determine the percent ligation at each time point. Gel band density of the ligated product was measured and divided by the sum of the band intensities of the ligated product and the unligated FAM-G probe. Data was graphed and shows that majority of the ligation occurs very fast (i.e. within a minute).

FIG. 8 shows TARA-L-PCR tests on various chemistry pairs. Results corroborated SDS-PAGE analyses, showing the recovery of the test line post-PCR for chemistry combinations 1-4, 6, and 8-9, while no test line was observed for chemistry combinations 5, 7 and 10. The data also shows that while no non-specific ligation in the absence of template was observable following TARA-L, non-specific ligation was observed following downstream amplification by PCR.

FIG. 10A shows TARA-L employing FDNB-activated probe G.

FIG. 10B shows TARA-L employing FNP-activated probe G.

FIG. 11A shows TARA-L employing FDNB-activated probe G.

FIG. 11B shows TARA-L employing FNP-activated probe G.

FIG. 12A shows TARA-L with a pre-incubation at 95° C. for 2 min.

FIG. 12B shows TARA-L without a pre-incubation at 95° C. for 2 min.

FIGS. 13A-3(b) show strip detection of TARA-L products after reaction at different temperatures (37° C., 45° C., 50° C., and 55° C.). Positive reactions contained both probes and template. Negative reactions contained probes only. PBST was used as chase buffer to run all samples on strips. PBST, without a TARA-L sample, was also run as control.

FIG. 13A shows lateral flow strip tests of TARA-L products.

FIG. 13B shows line intensity analysis by Image J. In the line graph, upper line represents "Positive" and lower line represents "Negative."

FIG. 14A shows TARA-L lateral flow strip detection.

FIG. 14B shows TARA-rt-PCR normalized amplification detection values.

FIGS. 15A-15B show embodiments of lateral flow test strip detection of serial diluted TARA-L ligation products in a comparison of TARA-L reactions employing DNFB or FNP as probe G activating agent. A series of TARA-L reactions, containing the same concentrated templates and probes, were carried out. FDNB- or FNP-activated probe G were quantified using UV absorption at 260 nm. After TARA-L reactions, products were both quantitated using real-time PCR (FNP-qPCR and FDNB-qPCR), and end-point strip detection after PCR amplified for 22 cycles (FNP-strip and FDNB-strip). FIG. 15A shows lateral flow strip results. FIG. 15B shows an embodiment of percentage test line intensities; results were normalized such that the most and least intense test lines were assumed to be 100% and 0%, respectively.

FIG. 16A shows TARA-L reactions employing FDNB as probe G activating agent.

FIG. 16B shows TARA-L reactions employing FNP as probe G activating agent.

FIGS. 17A-17B show examples of TARA-L-LAMP probe design according to some embodiments.

FIG. 17A shows the general design of TARA-L-LAMP probes according to some embodiments. 'Universal' adapters were designed using LAMP primer parameters to create a synthetic dumbbell structure that is directly compatible with LAMP. The probe target sequence may be unique to each analyte/organism/nucleic acid target and has sequences complimentary to the target nucleic acid sequence.

FIG. 17B shows an additional modification to TARA-L-LAMP probes to reduce or prevent non-specific ligation in the absence of a target nucleic acid. Hairpin stem-loops were designed into one or both probe target sequences to prevent non-specific ligation in the absence of template by physically occluding probe reactive ends.

FIG. 18A shows that in the presence of a target molecule stem-loops preferentially anneal/bind, open and allow the reactive ends to ligate FIG. 18B shows that ligated TARA products may essentially be LAMP dumbbell structures that can be directly amplified in a subsequent LAMP reaction, with only four primers, the 'universal' FIP/BIP and loop primers.

FIG. 20A shows agarose gel analysis of PCR-amplified gel-extracted ligated TARA-L-LAMP probes for FLU, OLF, MAL and DEN.

FIG. 20B shows lateral flow strip results for LAMP-amplified gel-extracted ligated TARA-L-LAMP probes for FLU, OLF, MAL and DEN.

FIG. 22A shows a 20-μl LAMP reaction for 30 min.
FIG. 22B shows a 20-μl LAMP reaction for 15 min.
FIG. 22C shows a 20-μl LAMP reaction for 10 min.
FIG. 22D shows a 50-μl LAMP reaction for 10 min.

FIG. 26A shows TARA-L-LAMP probe design for multiplexing according to some embodiments. A unique barcode sequence is inserted between the LB and B2c sequences located in the single-stranded loop portion of the A probe. A corresponding reverse complement sequence is inserted between the F2 and LFc sequences located in the single-stranded loop portion of the G probe. Probe sets designed to detect different targets will have their own unique barcodes.

FIG. 26B shows the early LAMP cascade and products produced according to some embodiments. The ligated product produce dumbbell structure 1. LAMP amplification of dumbbell structure 1 by BIP primers 5'-tagged with a reporter generate dumbbell structure 2, as well as a larger more complex product. The larger product continues in the LAMP cascade to produce complex products of increasing size and complexity. Dumbbell structure 2 contains a 5' reporter and the barcode sequence in the 3' end stem loop. LAMP amplification of dumbbell structure 2 by FIP primers 5'-tagged with a reporter regenerate dumbbell structure 1, as well as a larger more complex product that is essentially the reverse complement of the one produced by dumbbell structure 1. This larger product also continues in the LAMP cascade to produce complex products of increasing size and complexity. Products with a 5' reporter tag and a barcode sequence located in a single-stranded loop region are detectable by lateral flow assay. Specific oligonucleotides complementary to each unique barcode sequence allow selective capture of specific products within the lateral flow strip for multiplexing.

FIG. 27A shows TARA-L-PCR results.
FIG. 27B shows TARA-L-RPA results.
FIG. 27C shows TARA-L-RPA under optimized conditions for the RPA reaction.

FIG. 31 shows normalized relative amplifications levels based on Ct values from TARA-rt-PCR assays of mutated ssDNA sequences (FLUA1-M1, FLUA1-M2, FLUA1-M3 and FLUA1-K1) with mismatched nucleotides at various sites. The results were compared with that of wild-type template (FLUA1-WT). Results are shown for $10^{-5}$ µM (10 pM) template. BLK is a negative control for rt-PCR.

DETAILED DESCRIPTION

Figure 1A:
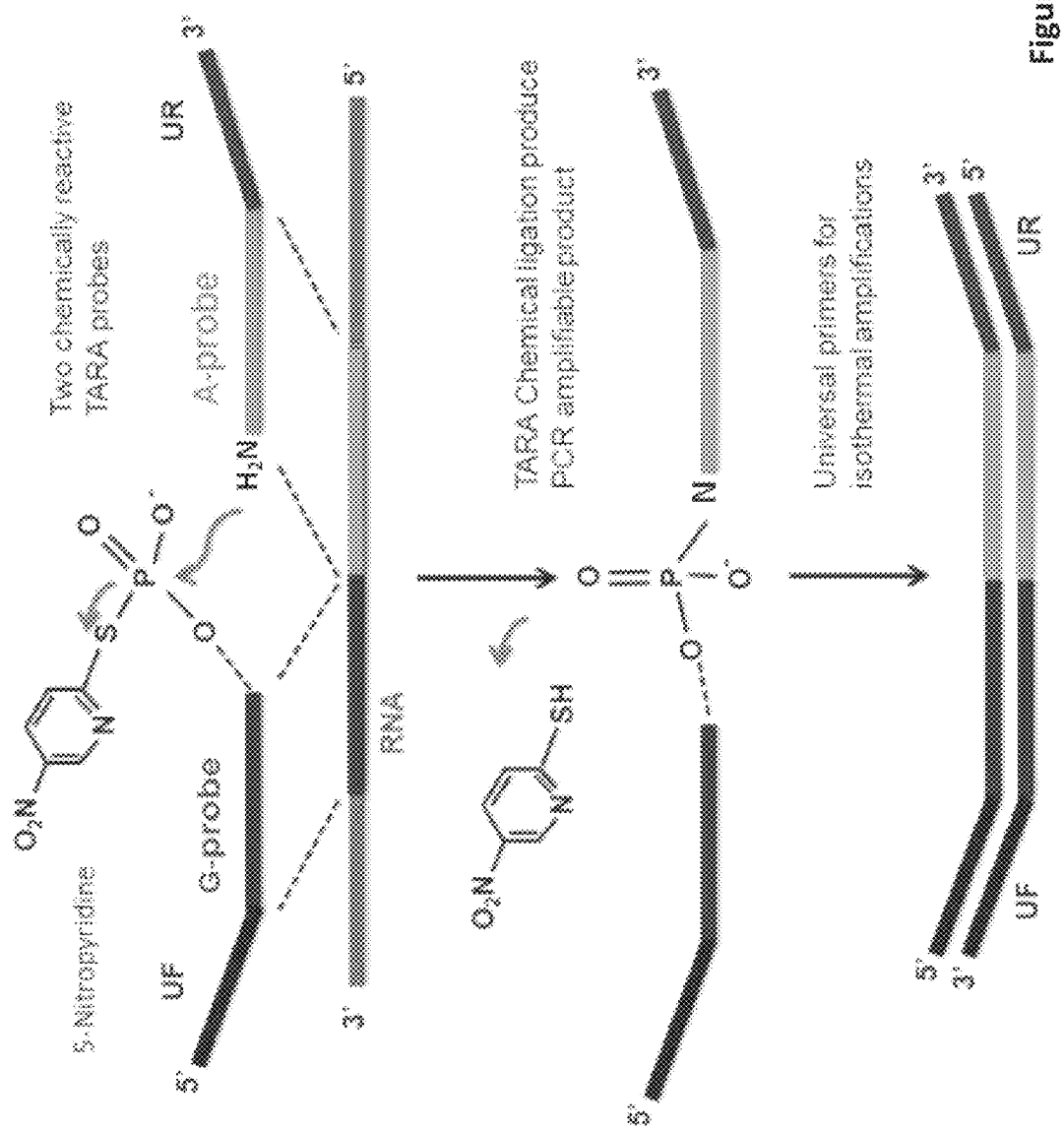

Ligase chain reaction (LCR) is a molecular diagnostic method that not only amplifies nucleic acids such as DNA, but allows for the discrimination of as little as a single-base substitution in nucleic acids. LCR typically uses two enzymes to operate: a thermostable enzyme called DNA ligase to join probe molecules together, and a thermostable polymerase to amplify those ligated probe molecules. The ligase works on its substrates, a 3-hyrdoxyl (OH) group on one nucleic acid probe, and a 5-phosphate (PO4) group on another nucleic acid probe, which have been brought directly adjacent to each other by hybridization with a template sequence comprising adjacent regions that are target sites for the probes. Thus, LCR can detect point mutations at the junction of the target sites for the two probes by performing the ligation right at the $T_m$ of the oligonucleotide probes.

Ligation-Based Template Assisted Rapid Assay (TARA-L)

Different from LCR, disclosed herein is a chemical ligation-based template assisted rapid assay (TARA-L) that works without the need of the ligase enzyme, utilizing chemical reactions between probes, such as chemical ligation. As used herein, "chemical ligation" or "ligation" refers to chemical reaction-based ligation of TARA probes without the need for or use of an enzyme to bring about the ligation reaction, unless indicated otherwise. In some embodiments, no enzymes are used in the TARA-L methods to achieve ligation of two or more probes. Thus, the reaction conditions and reagent storage conditions of TARA-L are much more environment-tolerant than LCR. As discussed below, in some embodiments enzymes may be used following the TARA-L ligation of the probes, for example to amplify the resulting ligation product.

Molecular diagnosis based on TARA-L, instead of LCR, is more compatible with point-of-need scenarios wherein point-of-care (POC) testing is desired. Non-limiting examples include blood glucose testing, blood gas and electrolytes analysis, rapid coagulation testing, rapid cardiac markers diagnostics, drugs of abuse screening, urine strips testing, pregnancy testing, fecal occult blood analysis, food pathogens screening, hemoglobin diagnostics, infectious disease testing and cholesterol screening.

TARA-L is based on the ligation of two different probes that are brought into proximity of each other. The probes comprise nucleic acid sequences that allow them to anneal (or hybridize) to a specific portion of a target analyte. In some embodiments a first probe anneals to a first specific portion of a target analyte and a second probe anneals to a second specific portion of a target analyte. The probes are designed and first and second portions of the target analyte are selected such that upon annealing of the first probe to the first portion of the target analyte and the second probe to the second portion of the target analyte the probes are in close enough proximity that they undergo chemical ligation to form a ligation product. Detection of the ligation product can thus be used to confirm the presence of the target analyte in a sample that has been contacted with the first and second probes.

In some embodiments a sample is to be evaluated for the presence of a nucleic acid associated with an analyte of interest. For example, a sample may be evaluated for the presence of a nucleic acid associated with a pathogen, such as a virus, bacteria or parasite. In some embodiments, a biological and/or clinical sample is evaluated for the presence of a nucleic acid associated with an analyte of interest. In some embodiments, the sample is taken from a patient suspected of suffering from or having been exposed to a disease and/or disorder and the analyte of interest is a target nucleic acid associated with the disease or disorder. In some embodiments, the sample is taken from a patient to determine if a target nucleic acid is present. In some embodiments, the target nucleic acid is a nucleic acid marker for a disease and/or disorder. In some embodiments, the target nucleic acid is associated with a disease and/or disorder, for example, an infection with a pathogen, clinical condition and/or genetic condition. In some embodiments, a sample is obtained from a patient to be tested for a disease and/or a disorder, for example, from a patient suspected of being exposed to or suspected of having a disease and/or a disorder.

In some embodiments, a wide range of types of samples can be evaluated for the presence of one or more target nucleic acids. Non-limiting examples include urine, nasal swab, nasal aspirate, oropharyngeal swab, urine, sweat, tears, blood, plasma, serum, saliva, semen, cerebrospinal fluid, lymph, and synovial fluid. In some embodiments the sample may not be from a subject. For example, in some embodiments samples may be taken from industrial processes, water treatment facilities, water storage facilities, and the like.

In some embodiments, the sample is a solid sample, a liquid sample, or a semi-solid sample. In some embodiments, the sample is dissolved or dispersed in a liquid (e.g., saline solution or a buffer).

In some embodiments, the target analyte (also referred to herein as an analyte of interest or simply an analyte) is or comprises a target nucleic acid molecule (also referred to herein as a target nucleic acid). Thus, in some embodiments the probes anneal (or hybridize) to specific portions of a target nucleic acid by pairing between complementary nucleotides. In some embodiments, the target nucleic acid comprises DNA and/or RNA. In some embodiments, the probes comprise nucleic acid sequences that allow them to anneal in close proximity to each other on a target nucleic acid, and the probes comprise chemical modifications to facilitate the ligation of the different probes upon annealing or otherwise binding to the target nucleic acid in close enough proximity and under the appropriate reaction conditions. In some embodiments, the probes are referred to herein as the G probe and the A probe. In some embodiments, the G probe anneals downstream of the A probe on the target nucleic acid such that the 3' end of the G probe and 5' end of the A probe are brought into close proximity upon annealing and undergo a chemical ligation reaction to join the G and A probes, resulting in the formation of a single nucleic acid sequence comprising the G and A probes ("chemically ligated product", "ligated product" or "ligation product").

In some embodiments, the probes comprise first probe (e.g., G probe) comprising a first nucleic acid region, which is complementary to a first part of a target nucleic acid. The 3' end of the G probe may be modified with a first chemical group. A second probe (e.g., A probe) comprises a second nucleic acid region, which is complementary to a second part of the target nucleic acid. The 5' end of the A probe may be modified with a second chemical group. The first and second chemical groups used to modify the G probe and A probe, respectively, are selected such that when the 3' end of the G probe is in proximity of the 5' end of the A probe under appropriate reaction conditions and in the presence of a target nucleic acid, the G and A probes are chemically ligated to form a ligation product.

In some embodiments, the first part and the second part of the target nucleic acid are substantially adjacent to each other within the target nucleic acid such that the first and second chemical groups of the first and second probe are in close enough proximity to chemically ligate to each other upon binding of the first and second probes to the target nucleic acid. Thus, when the first nucleic acid region of the first probe hybridizes to or otherwise binds to the first part of the target nucleic acid and the second nucleic acid region of the second probe hybridizes to or otherwise binds to the second part of the target nucleic acid, the first and second probes ligate to each other through a reaction between the first and second chemical groups.

In some embodiments, the probes anneal on the target nucleic acid sequence substantially adjacent to each other. In some embodiments, the first part and the second part of the target nucleic acid sequence are substantially adjacent to each other in the target nucleic acid sequence. In some embodiments the first part and second part of the target nucleic acid sequence are directly adjacent to each other, with no intervening nucleotides. In some embodiments there is a separation of at most 50 nucleotides between the first and second part of the target nucleic acid sequence. In some embodiments there is a separation of at most 10 nucleotides between the first and second part of the target nucleic acid sequence. In some embodiments there is a separation of 0, 1, 2, 3, 4, 5, 6, 7, 8, 9 or 10 nucleotides between the first and second part of the target nucleic acid sequence. The particular spacing can be selected based on, in part, the selected ligation chemistry.

In some embodiments, a distance between the first part and the second part of the target nucleic acid sequence is from 1 to 2, 1, or 0 nucleotides. In some embodiments of the method of determining the presence and/or level of an analyte in a sample, a distance between the first part and the second part of the target nucleic acid sequence is from 1 to 5 nucleotides. In some embodiments of the method of determining the presence and/or level of an analyte in a sample, a distance between the first part and the second part of the target nucleic acid sequence is from 0 to 10 nucleotides. In some embodiments of the method of determining the presence and/or level of an analyte in a sample, a distance between the first part and the second part of the target nucleic acid sequence is from 0 to 20 nucleotides. In some embodiments of the method of determining the presence and/or level of an analyte in a sample, a distance between the first part and the second part of the target nucleic acid sequence is from 0 to 50 nucleotides.

In some embodiments, the probes anneal on the target nucleic acid such that there is a separation of at most 10 nucleotides between the first part and the second part of the target nucleic acid. In some embodiments, the probes anneal on the target nucleic acid such that there is a separation of 0, 1, 2, 3, 4, 5, 6, 7, 8, 9, or 10 nucleotides.

In some embodiments, the size of the probes can range from about 10 nucleotides to about 50 nucleotides. The size of each of the first and second probes can be independently selected. In some embodiments the size of the first probe and the size of the second probe are the same. In some embodiments the first and second probes have different sizes. In some embodiments, the size of the probes can range from about 20 nucleotides to about 100 nucleotides. In some embodiments, the size of the probes can range from about 30 nucleotides to about 150 nucleotides. In some embodiments, the size of the probes can range from about 40 nucleotides to about 200 nucleotides. In some embodiments, the size of the probes can range from about 50 nucleotides to about 250 nucleotides. In some embodiments, the size of the probes can range from about 100 nucleotides to about 500 nucleotides.

In some embodiments, the probes are designed in a way that the probes are able to anneal to a target nucleic acid under the desired conditions. In some embodiments, the probes comprise a nucleic acid with a specific sequence that allows them to anneal to a target nucleic acid. As noted previously, annealing brings the probes into close proximity and chemical ligation takes place. In this way, target nucleic acid is identified in the sample. In some embodiments, probes can be designed such that they will only anneal and ligate when the sequence match between the probes and the target nucleic acid is perfect (i.e., 100%). Thus, in some embodiments, the probes are nucleic acids that are completely complementary to the target nucleic acid. Therefore, even a single nucleotide mismatch between one or both probes and the target nucleic acids can be discriminated. In some embodiments, it is not necessary to have 100% sequence match between the probes and the target nucleic acid. In some embodiments, the probes and the target nucleic acid are 75, 80, 85, 90, 95, 96, 97, 98, 99, 99.1, 99.2, 99.3, 99.4, 99.5, 99.6, 99.7, 99.8, 99.9, or 100% complementary to each other. In some embodiments, one of the probes is 100% complementary to the target nucleic acid whereas the other probe is 75, 80, 85, 90, 95, 96, 97, 98, 99, 99.1, 99.2, 99.3, 99.4, 99.5, 99.6, 99.7, 99.8, or 99.9% complementary to the target nucleic acid. In some embodiments, both probes are 100% complementary to the target nucleic acid. In some embodiments, a desired specificity between the probes and the target nucleic acids can be obtained by other means.

In some embodiments, the probes are designed in a way that the probes are able to anneal to a target nucleic acid and ligate under the desired conditions. For example, in some embodiments the probes are designed such that the probes are able to anneal to the target nucleic acid and ligate at a desired temperature. In some embodiments, the probes are designed such that the probes are able to anneal to the target nucleic acid sufficiently to ligate and form a ligation product at room temperature.

In some embodiments, the concentration of the probes, in a sample in which a target nucleic acid is to be detected, is less than 1 nM. In some embodiments, the concentration of the probes, after mixing with a sample in which a target nucleic acid is to be detected, is less than 1 nM. In some embodiments, the concentration ranges from less than about 1 nM to about 10 pM. In some embodiments, the concentration ranges from less than about 1 nM, 500 pM, 250 pM, 100 pM, 50 pM, 25 pM, or 10 pM. In some embodiments, the concertation is less than 10 pM.

In some embodiments, target nucleic acids comprise one or more of nucleic acids from various organisms such as influenza virus, dengue virus, HCV, coronavirus, malaria, *Toxoplasma*, Opisthorchiid liver flukes. In some embodiments, the target nucleic acid comprises mRNA, DNA, and/or microRNA. In some embodiments, TARA-L probes are designed to detect microRNAs. For example, Table 1 shows non-limiting examples of the sequences of the probes, primers, and templates designed and synthesized for TARA-L-based microRNA detection.

In some embodiments, one or more additional sets of probes can be utilized. In some embodiments, each additional set of probes hybridizes to a different target nucleic acid sequence. In some embodiments, one or more additional sets of probes can be directed to a different nucleic acid sequence on the same target analyte. In some embodiments one or more additional sets of probes can be directed to different target analytes, allowing for the detection of multiple different analytes in the same sample simultaneously.

Chemical Ligation Chemistries

The chemical ligation between the G and A probes can be based on any of several different chemistries of chemical groups. For example, TARA-L may be based on any of the several specific chemical reactions of chemical groups as illustrated in FIGS. 1A-1E.

In some embodiments, the two or more different TARA-L probes, such as the G probe and A probe, are modified with different chemical ligatoin groups. In some embodiments, TARA-L probes comprise various combinations of the different chemical groups. The various combinations of the different chemical ligation groups provide different options for ligations in a template-assisted manner under TARA-L reaction conditions. Table 2 shows non-limiting examples of ten different chemical-group combinations that can be used for TARA-L. Other combinations of chemical groups that can be applied for chemical ligation of the probes are also contemplated.

In some embodiments, a first probe is modified to allow it to ligate to a second (or more) probe that is brought into proximity of the first probe when the first and second probes anneal to or otherwise bind to a target nucleic acid. In some embodiments the probes contain a chemical modification at one or both of the 5' and/or 3' ends. In some embodiments a probe set includes a first probe that is modified at the 3' end and configured to bind to a first part of a target nucleic acid and a second probe configured to anneal to the target nucleic acid in proximity to the first probe, where the second probe is modified at the 5' end in such a way that when the first and second probes anneal in proximity to each other on the target the modified ends are able to interact and ligate the two probes, forming a chemically ligated product.

In some embodiments, the probes are provided in a probe buffer. In some embodiments, an activator is included in the probe buffer. The activator serves to activate or drive the chemical ligation of the two or more probes when they are annealed in proximity on the target nucleic acid. Non-limiting examples of activators include 2-Fluoro-5-nitropyridine (FNP), 1-Fluoro-2,4,6-Trinitrobenzene (FTNB), 1-Fluoro-2,4-dinitrobenzene (FDNB), and succinimidyl iodoacetate (SIA). In some embodiments the probes are provided to a sample comprising a target analyte in the absence of activator and the activator is subsequently added. In some embodiments the probes are provided to a sample comprising a target analyte and activator. In some embodiments a sample to be evaluated for the presence of a target analyte is added to a reaction mixture comprising one or more probe sets and an activator. In some embodiments an activator is added to a reaction mixture after the sample. In some embodiments an activator is not used.

In some embodiments, TARA-L utilizes 2-Fluoro-5-nitropyridine (FNP), to activate ligation of two probes through a thiophosphate (—PS) group at the end of a first probe and a primary amine group (—$NH_2$) at the end of a second probe. In some embodiments, one probe comprises a —PS group at one of the 3' or 5' end and a second probe comprises a primary amine group at the other of the 3' or 5' end relative to the first probe. For example, in some embodiments, one probe comprises a —PS group at the 3' end and a second probe comprises a primary amine group (—$NH_2$) at the 5' end. The FNP activator may be included to facilitate the ligation of the two probes when they are in sufficiently close proximity on the target nucleic acid.

In some embodiments, TARA-L utilizes 1-Fluoro-2,4,6-Trinitrobenzene (FTNB) to activate ligation through a thiophosphate (—PS) group at one end of a first probe and a different group at the end of a second probe, for example a primary amine groups (—$NH_2$), when the first and second probes are in close proximity on a target nucleic acid. For example, in some embodiments, one probe comprises a —PS group at the 3' end and a second probe comprises a primary amine group (—$NH_2$) at the 5' end. The FTNB activator may be included to facilitate the ligation of the two probes when they are in sufficiently close proximity on the target nucleic acid.

In some embodiments, TARA-L utilizes 1-Fluoro-2,4-dinitrobenzene (FDNB) to activate ligation through a thiophosphate (—PS) group at one end of a first probe and a different group at the end of a second probe, for example a primary amine groups (—$NH_2$), when the first and second probes are in close proximity on a target nucleic acid. For example, in some embodiments, one probe comprises a —PS group at the 3' end and a second probe comprises a primary amine group (—$NH_2$) at the 5' end. The FDNB activator may be included to facilitate the ligation of the two probes when they are in sufficiently close proximity on the target nucleic acid.

In some embodiments, TARA-L utilizes succinimidyl iodoacetate (SIA) to activate ligation through a primary amine groups (—$NH_2$) at the one end of one probe, such as at the 5'-end of one probe, and a second chemical group, for example a thiophosphate (—PS) group, at one end of a second, different probe, such as at the 3'-end, when the first and second probes are in close proximity on a target. For example, in some embodiments, one probe comprises a —PS group at the 3' end and a second probe comprises a primary amine group (—$NH_2$) at the 5' end. The SIA activator may be included to facilitate the ligation of the two probes when they are in sufficiently close proximity on the target nucleic acid.

In some embodiments more than one activator can be used. For example, in some embodiments, TARA-L utilizes at least two of 2-Fluoro-5-nitropyridine (FNP), 1-Fluoro-2,4-dinitrobenzene (FDNB), and 1-Fluoro-2,4,6-Trinitrobenzene (FNTB) to activate ligation of two probes, where one probe comprises a thiophosphate (—PS) groups at one end, such as at the 3'-end and a second, different probe comprises a primary amine group (—NH$_2$) at the opposite end, such as at the 5'-end, when the two probes are in close proximity on a target nucleic acid.

Figure 1B:
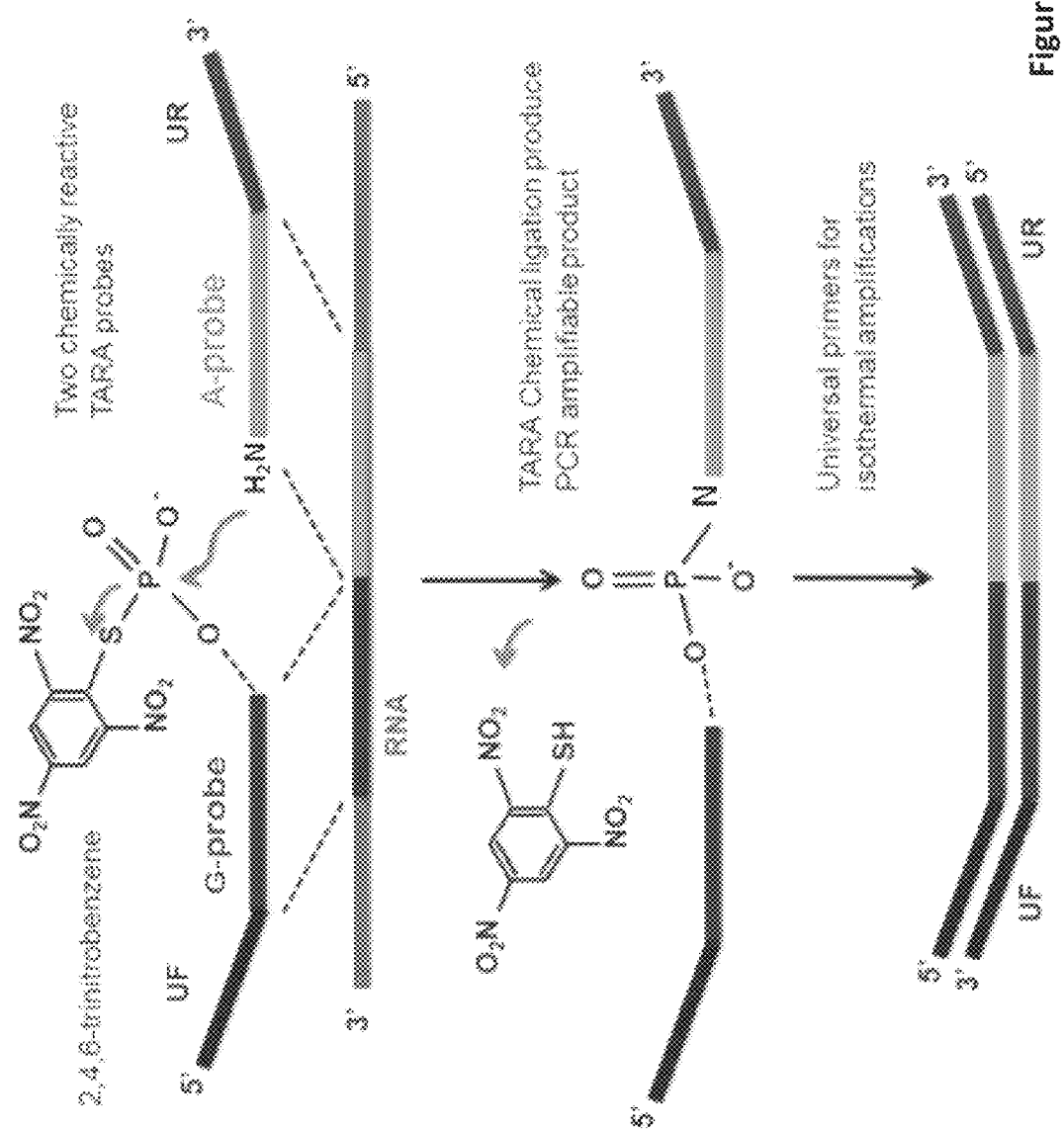
Figure 1C:
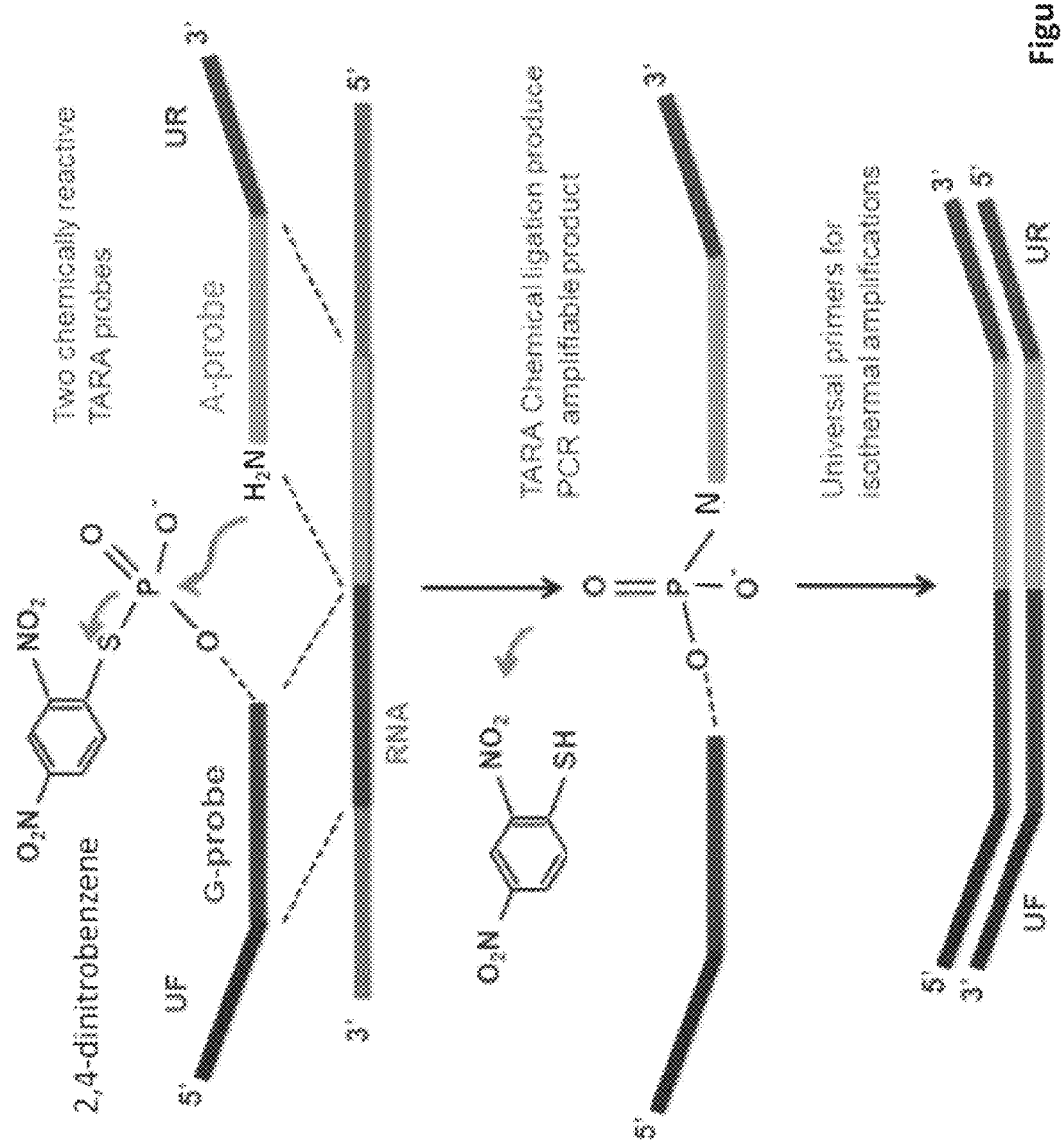

In some embodiments, TARA-L chemical ligation is based on 2-Fluoro-5-Nitropyridine (FNP) s illustrated in FIG. 1A. In some embodiments, TARA-L chemical ligation is based on 1-Fluoro-2,4,6-Trinitrobenzene (FTNB) as illustrated in FIG. 1B. In some embodiments, TARA-L chemical ligation is based on 1-Fluoro-2,4-Dinitrobenzene (FDNB) as illustrated in FIG. 1C. In some embodiments, TARA-L chemical ligation is based on succinimidyl iodoacetate (SIA)-based as illustrated in FIG. 1D. In some embodiments, TARA-L chemical ligation is based on thiophosphate (FTNB) as illustrated in FIG. 1E.

In some embodiments, the chemical ligation reaction comprises activation of a thiophosphate group by an activator and ligation of the activated thiophosphate group on one primer to a primary amine group on a second primer.

In some embodiments, the chemical ligation reaction comprises activation of a primary amine group by an activator and ligation of two probes through the activated amine group and a thiophosphate group.

In some embodiments, the chemical ligation reaction comprises no activation of a thiophosphate group and ligation of two thiophosphate groups.

In some embodiments, no activator is used.

In some embodiments one or more additional sets of probes is utilized to evaluate a sample for the presence of a target nucleic acid. In some embodiments each set of probes utilizes the same chemical ligation groups. In some embodiments different sets of probes utilize different chemical ligation groups.

In some embodiments, each additional set of probes utilizes the same activator. In some embodiments, each additional set of probes utilizes a different activator.

Without being limited by any particular theory, due to the reactive nature of the chemical groups (Table 2), it is possible for ligation to occur between modifications among the same probe (e.g., G-G probe ligation) at high concentrations and in the absence of an inhibitor compound such as a reducing agent. Such non-specific ligations can be seen, for example, on SDS-PAGE as the appearance of an extra band of ligated product or a shift in the band position of the chemically ligated product. In some embodiments, such as when high concentrations of probes are present, a reducing agent or other inhibitor compound may be included in the reaction mixture to reduce non-specific interaction between probes.

In some embodiments, probe storage buffers and/or ligation reaction buffers contain reducing agents selected from a group consisting of, but not limited to, DTT (dithiothreitol) and TCEP (tris(2-carboxyethyl)phosphine).

In some embodiments, the reducing agent in the probe storage buffers and/or ligation reaction buffers is one or more of DTT and TCEP.

Without being limited by any particular theory, in some embodiments, there exists the potential for homo-ligated-dimers of probes containing the PS chemistry (G-G or A-A). There also exists the potential for PS-containing probes to non-specifically ligate to either 5'- or 3'-OH groups present in unmodified synthetic oligonucleotides. In some embodiments, such issues can be resolved by the addition of a reducing agent, such as TCEP or DTT. In some embodiments, no reducing agent is used.

In some embodiments, the TARA ligation reactions occur extremely rapidly. In some embodiments, the TARA ligation reaction occurs within 10 seconds of mixing the probes with a sample/of adding the probes to a sample in which a target nucleic acid is to be detected In some embodiments, the TARA ligation reaction occurs within 10, 20, 30, 40, 50, or 60 seconds. In some embodiments, the majority of the ligation takes place in less than 5 minutes. In some embodiments, the TARA ligation reaction occurs within 1, 1.5, 2, 2.5, 3, 3.5, 4, or 4.5 minutes of mixing the probes with a sample/of adding the probes to a sample in which a target nucleic acid is to be detected. In some embodiments, the ligation is rapid for FNP chemistry, with a 5-min reaction producing similar amount of ligated product as a 15-min reaction. In some embodiments, the ligation is rapid for SIA chemistry, with a 5-min reaction producing similar amount of ligated product as a 15-min reaction. In some embodiments, the ligation is rapid for both FNP and SIA chemistries, with a 5-min reaction producing similar amount of ligated product as a 15-min reaction. In some embodiments, a majority of the ligation product is formed within the first five minutes and very little additional ligation product is produced between 5 and 15 minutes.

In some embodiments, the probes and/or activator are added to a sample comprising an analyte at room temperature and the ligation reaction occurs at room temperature. In some embodiments, the probes and/or activator are contacted with the sample such that the ligation occurs at room temperature if the analyte is present in the sample. In some embodiments, the sample can be heated, if necessary, to obtain a desired condition for the ligation reaction to occur. In some embodiments, the ligation occurs at a temperature of about 30-40° C. This may be achieved by heating if necessary. In some embodiments of the method of determining the presence and/or level of an analyte in a sample, the ligation occurs at a temperature of about 35-45° C. In some embodiments of the method of determining the presence and/or level of an analyte in a sample, the ligation occurs at a temperature of about 40-50° C. In some embodiments of the method of determining the presence and/or level of an analyte in a sample, the ligation occurs at a temperature of about 45-55° C. In some embodiments of the method of determining the presence and/or level of an analyte in a sample, the ligation occurs at a temperature of about 50-60° C. In some embodiments of the method of determining the presence and/or level of an analyte in a sample, the ligation occurs at a temperature of about 55-65° C. In some embodiments of the method of determining the presence and/or level of an analyte in a sample, the ligation occurs at a temperature of about 60-70° C.

In some embodiments, the sample is mixed directly with the probe buffer comprising the probes and one or more activators. In some embodiments, the sample is first dissolved or dispersed in a liquid before mixing with the probe buffer comprising the probes and one or more activators.

In some embodiments, when the sample is mixed directly with the probe buffer comprising the probes and one or more activators, the TARA-ligation reaction is performed directly on the sample. For example, in some embodiments, TARA-ligation reactions can be performed directly on saliva, blood, plasma, urine, and BSA (Bovine Serum Albumin). In some embodiments, no/minimal inhibition of the TARA-ligation reaction occurs in the presence of saliva, blood plasma and BSA (e.g., FIG. 9). In some embodiments, TARA ligation can even be performed in the presence of harsh lysis buffer conditions, for example, when a sample is mixed directly with a lysis buffer (e.g., CLBuffer-1 and CLBuffer-2). Thus, TARA-ligation reactions are robust and applicable for testing with biological samples.

In some embodiments, TARA-L-based molecular diagnostic methods for detecting and/or quantitating an analyte of interest are provided. In some embodiments, TARA-L-based molecular diagnostic methods utilize a chemical ligation and annealing of the probes in the presence of a target nucleic acid followed by an immunochromatographic assay including, but not limited to, lateral flow assays (LFAs) that in turn comprise aspects of one or more of immunoaffinity technology, immunoblotting technology, and spot thin-layer chromatography technology.

In some embodiments, TARA-L-based molecular diagnostic methods involves target detection by TARA-L-based chemical ligation of the probes upon annealing in close proximity to each other on a target nucleic acid followed by detection of the ligated product using an immunochromatographic strip (e.g., an LFA strip).

In some embodiments, a sample is directly mixed with specifically designed probes and buffers. Probes are ligated to each other when they anneal in close proximity on a target nucleic acid, if present in the sample. In some embodiments, based on the amount of target nucleic acid in the sample, the probes ligate to each other when they anneal in close proximity on a target nucleic acid in a quantity that corresponds to the amount of target nucleic acid in the sample. Following the ligation reaction, the presence of ligated product can be determined by immunochromatography (e.g., LFA). The signal of the ligated product as determined by immunochromatography (e.g., LFA) is quantitatively related to the amount and/or concentration of target nucleic acid.

In some embodiments the molecular diagnostic methods for detecting and quantifying a target nucleic acid in a sample comprises two steps: Step 1 adding the probes, designed to anneal specifically to the target nucleic acid of interest, to a sample that is to be analyzed for the presence and/or quantity of the target nucleic acid. The probes anneal at adjacent target sites, the target sites being close enough that the annealed probes are in close enough proximity to undergo chemical ligation under the reaction conditions, resulting in chemical ligation of the probes. In some embodiments, the ligation reaction happens essentially instantly (<1 min) at a relatively mild temperature (50-60° C.). Step 2 comprises detection of the ligated product.

In some embodiments, the sample is first mixed with probes, which are specifically designed for the specific target nucleic acid (e.g., a molecular marker of a disease or disorder) and buffers. A simple and short incubation results in the probes annealing to the specific target nucleic acid, if present, among all of the nucleic acids in the sample, resulting in chemical ligation of the probes upon annealing in close proximity to each other on a target nucleic acid ligated quantitatively. For example, probes can be ligated to each other in a short reaction (e.g., 1 minute) at an elevated temperature (e.g., 50-60° C.).

The target nucleic acid serves as a template for the probes to anneal. The probes chemically ligate to form a single nucleic acid molecule that produces a double-stranded sequence comprising the ligated product and the target nucleic acid.

In some embodiments, the probes are highly specific to the sequence of the target nucleic acid in the sample. In some embodiments, the first and second nucleic acid regions are exactly complementary to the first and second parts of the target nucleic acids. In other embodiments, the complementarity may be less, provided that it provides the desired level of specificity for detecting the target sequence under the desired reaction conditions. Thus, the chemical ligation reaction is highly specific to the sequence of the target nucleic acid. In some embodiments, target nucleic acids with single nucleotide polymorphisms can be differentiated. In some embodiments, target nucleic acids with at least one nucleotide polymorphism can be differentiated polymorphism.

In some embodiments, one or more blocking groups can be added to one or both probes. For example, different 5'-blocking groups (e.g., 5-FAM) can be used as labels to provide multiplexing capabilities by capture and signal reporting.

Due to the reactive nature of the chemical groups (Table 2), it is possible for ligation to occur between modifications among the same probe (e.g., G-G probe ligation) at high concentrations. In some embodiments, the G and A probes are labeled with different labels to create dual labelled ligation products such that they can be distinguished from non-specific ligation between the same probe (e.g., G-G probe ligation).

In some embodiments, one or more barcoding sequence/barcodes can be added to the probes to allow for specific capture of ligation products. In some embodiments, one or more barcoding sequence/barcodes can be added to the primers to allow for subsequent ligation and capture of ligation products. In some embodiments, adding different barcoding sequences/barcodes to different sets of probes allows for multiplexed reactions. In some embodiments, a multiplexed reaction comprises detecting one target nucleic acid with multiple sets of probes. In some embodiments, a multiplexed reaction comprises detecting multiple target nucleic acids with multiple sets of probes.

In some embodiments, a barcoding sequence can be added between the two primers sequences within the single stranded region of the dumbbell stem-loop for one or both probes, thus allowing for probe capture, as well as have applications in multiplexing, for example, by allowing you to identify particular ligated products.

Combination of TARA-L with Amplification

In some embodiments, in situations where the target analyte is present in a very small amount (e.g., a single copy), the methods can be combined with amplification tools to increase the detection sensitivity. Thus, in some embodiments, the formation of the chemically ligated product by TARA-L in the presence of a target nucleic acids does not involve the use of an enzyme. However, an enzyme may be used later, such as to amplify the ligated product. In some embodiments, probes are chemically ligated to each other when they anneal in close proximity on a target nucleic acid. The chemically ligated product are then amplified using non-isothermal and isothermal nucleic acid amplification methods. Non-limiting examples include PCR, real time-PCR (rt-PCR), reverse transcriptase-PCR (RT-PCR), quantitative-PCR (qPCR). In some embodiments, the chemically ligated product are amplified using isothermal nucleic acid amplification. Non-limiting examples include recombinase-polymerase amplification (RPA) and loop-mediated isothermal amplification (LAMP). In some embodiments, the chemically ligated products are amplified using both non-isothermal and isothermal nucleic acid amplification methods. In some embodiments, the ligated product can be amplified using non-isothermal (e.g., PCR) and/or isothermal (for example, RPA or LAMP) nucleic acid amplification compatible.

In some embodiments, for example for early diagnosis of a disease in a patient sample that may only contain a limited number of the target nucleic acid (e.g., <100 copies of a target nucleic acid that is a molecular marker for a disease), the chemically ligated product from TARA-L can be amplified, such as by PCR, RPA, and/or LAMP. The amplified chemically ligated product can then be an immunochromatography assay (e.g., LFA). In this way, it is possible to obtain an ultrasensitive nucleic acid-based diagnosis of the presence of a presence of a target nucleic acid, such as a molecular marker of a condition such as a disease, disorder and/or a condition.

In some embodiments, the number of copies of the target nucleic acid that can be detected can range from 1 to about 10. In some embodiments, the number of copies of the target nucleic acid can range from 10 to about 100. In some embodiments, the number of copies of the target nucleic acid can range from 100 to about 1000. In some embodiments, the number of copies of the target nucleic acid can range from 1000 to about 10,000. In some embodiments, the number of copies of the target nucleic acid can range from 10,000 to about 100,000.

In some embodiments, TARA-L-based the chemical ligation of the probes in the presence of a target nucleic acids can be further combined with PCR (referred to as TARA-L-PCR). In some embodiments, TARA-L-based the chemical ligation of the probes in the presence of a target nucleic acids can be further combined with RPA (referred to as TARA-L-RPA). In some embodiments, TARA-L-based the chemical ligation of the probes in the presence of a target nucleic acids can be further combined with LAMP (referred to as TARA-L-LAMP).

In some embodiments, TARA-L-RPA employs a primer/probe (Example 4.1) for detection in real-time and/or on lateral flow strips.

In some embodiments, TARA-L-RPA does not employ a primer/probe for detection in real-time and/or on lateral flow strips.

In some embodiments, one or more probes comprise 'universal' and/or specific primer sequences for downstream amplification with, for example, PCR, RPA and/or LAMP. In some embodiments, one or more probes comprise 'universal' and/or specific adapters comprising 'universal' and/or specific primer sequences for downstream amplification with, for example, PCR, RPA and/or LAMP.

In some embodiments, the probes comprise universal primer sequences that allow for amplification with universal primers. In some embodiments, the probes comprise specific primer sequences for amplification with specific primers. In some embodiments, the probes comprise both universal and specific primer sequences that allow for amplification with universal and specific primers. Non-limiting examples of universal primer sequences include M13, T7, and SP6 primer sequences.

In some embodiments, one or more probes comprise 'universal' and/or specific primers sequences, and/or 'universal' and/or specific adapters sequences comprising 'universal' and/or specific primers sequences, located 5' to the first nucleic acid region of the first probe (e.g., G probe) and 3' first nucleic acid region of the second probe (e.g., A probe) for downstream amplification with, for example, PCR, RPA and/or LAMP.

In some embodiments, ligated product is amenable to amplification with PCR, RPA, and/or LAMP. In some embodiments, the probes can be first tested on LFA strips to ensure proper initial TARA ligation. In situations where the signal of the ligated product on the LFA strips requires further verification, the ligated product can be subjected to PCR, RPA, and/or LAMP and again tested on LFA strips (e.g., FIG. 8).

In some embodiments, the probes do not contain a reporter. Instead, reporters are attached to primers used during an amplification reaction (PCR, RPA, and/or LAMP) post-TARA-L. For example, the first probe is ligated to the second probe in the presence of the target nucleic acid sequence, and then ligated product is amplified by PCR, RPA, or LAMP using at least one primer that comprises a reporter, whereby products containing the reporter(s) are produced and the presence and/or level of the reporter(s) can be measured to determine the presence and/or amount of analyte. In some embodiments, a reporter is present only on a primer that is specific for one of the probes. In some embodiments, a reporter is present on primers that are specific for both probes.

In some embodiments, the primers are labeled with reporters. Non-limiting examples of reporters include Biotin, FITC, 5-FAM, and digoxin.

In some embodiments, the universal and/or specific adapters in the one or more probes comprise one or more secondary structures such as, but not limited to, stem-loops and/or hairpins. In some embodiments, the one or more secondary structures specifically designed for functionality with downstream amplification (e.g., LAMP).

In some embodiments, hairpin stem-loops are designed into one or both probes to prevent non-specific ligation in the absence of a template. In some embodiments, hairpin stem-loops are designed into only one of the two probes to prevent non-specific ligation in the absence of a template. In some embodiments, hairpin stem-loops are designed into both probes to prevent non-specific ligation in the absence of a template.

In some embodiments, non-specific ligation of TARA probes can occur in the absence of a target molecule, especially at high concentrations, due to the reactive ends of the probes coming into proximity randomly within solution. This becomes increasingly more important when TARA ligation is followed by a subsequent amplification step (e.g., as seen in FIG. 8 and FIG. 16). In some embodiments, hairpin stem-loops are designed into one or both probe (on G and/or A probe) to prevent non-specific chemical ligation of the probes when the target nucleic acid is not present (e.g., FIG. 17B).

In some embodiments, one or both probe target sequences contain secondary structures such as, but not limited to, stem loops and hairpins, specifically designed to prevent non-template (non-specific) ligation in the absence of the target analyte. These structures are meant to physically occlude reactive probe ends from contacting and ligating with one another without annealing to a target analyte in a specific manner as to bring the reactive ends into close proximity for ligation.

Combination of TARA-L with Immunochromatography

In some embodiments, the ligated product is detected. Detection of the ligated product can be used to confirm the presence of a target nucleic acid in the sample. This, in turn, can be used, for example, to identify the presence of a pathogen in a sample, or to diagnose a disease or disorder in a subject. Detection can be carried out by any of a variety of methods, such as by labelling one or both probes. In some embodiments, one or both probes are labelled with, and comprise, one or more reporter molecules such that the ligated product can be detected. In some embodiments, at least one probe carries a label. In some embodiments, both probes carry a label. In some embodiments, the probes carry labels that can be directly detected using one or more techniques such as immunochromatograph-based assays. In some embodiments unligated probes are removed such that only ligated products are detected.

Non-limiting examples of reporters include fluorophores (e.g., fluorescein, fluorescein isothicyanate (FITC), (phycoerythrin) PE, Hydroxycoumarin, and the like), 5-Carboxyfluorescein (5-FAM), Biotin, and digoxin. In some embodiments, the reporters are one or more fluorescent proteins (e.g., GFP, RFB, BFFP, and the like). In some embodiments, the reporters include nano-particles (e.g., quantum dots), micro-particles, or another reporter. In some embodiments, the probes comprise one or more fluorophores, fluorescent proteins, and/or nano- or micro-particles or another reporter.

In some embodiments, only one of the two probes in a probe ligation pair comprises a reporter. In some embodiments, only the first of the two probes comprises a reporter. In some embodiments, the first probe comprises one or more reporters. In some embodiments, the second probe comprises one or more reporter. In some embodiments, both probes comprise comprises one or more reporters. In some embodiments, both probes comprise different one or more reporters. For example, the first probe may be associated with one or more nano- or micro-particles or other reporter, and the second probe may be associated with one or more nano- or micro-particles or another reporter different from the first probe. In some embodiments, both probes comprise the same one or more reporters. In some embodiments, when both probes comprise the same one or more reporters, an enhanced and/or stronger signal may be obtained.

In some embodiments, the first and second probes comprise one or more light-sensitive reporters such that the one or more light-sensitive reporters on the first and second probes produce a fluorescence resonance energy transfer (FRET) signal only when the probes are brought into close proximity via ligation in the presence of a target nucleic acid. Thus, in some embodiments, the one or more light-sensitive reporters on the first and second probe interact with each other to generate a signal only when the first and second probes are ligated to each other. In some embodiments, the first and second probes comprise one or more bioluminescent reporters for bioluminescent resonance energy transfer (BRET).

In some embodiments, when the probes comprising one or more reporters are ligated to each other in the presence of a target nucleic acid, the presence and/or level of the reporter can be measured to determine the presence and/or amount of analyte based on a level of signal obtained from the one or more reporters. In some embodiments, probes comprising one or more reporters can be used to detect the presence and/or quantify a target nucleic acid.

In some embodiments, the probes carry labels that can be directly detected using one or more techniques such as immunochromatograph-based assays. In some embodiments, the probes carry labels that can be directly detected using on or more immunochromatograph-based assays such as LFA In some embodiments, the detection can be visual. In some embodiments, the detection is using equipment such as a scanner, a colorimeter, a fluorescence microscope, and the like. In some embodiments, the detection is both visual and using equipment.

In some embodiments, LFA involves binding the ligation product to gold particles or some other label and then capturing the bound complex and visualizing it.

In some embodiments, the labeled ligated products are purified before visualization by LFA. In some embodiments, the labeled ligated products are purified before visualization by LFA such that only the labeled ligated products are visualized and not unligated labeled probes.

In some embodiments, an LFA comprises an immunochromatography test strip comprising a sample pad, a conjugation pad, a reaction membrane, and an absorbent pad. A sample in liquid form comprising a target analyte is loaded into the sample pad. The sample pad acts as a sponge and holds an excess of the sample in liquid form. Once the sample pad is soaked, the sample flows from the sample pad to the conjugation pad. When the labeled chemically ligated product reaches the conjugation pad, the label on the chemically ligated product and is bound by the an immobilized agent (e.g., an antibody) in the conjugation pad. The conjugation pad comprises control and test lines. The former acts as a control for the performance of the assay. The latter is to determine whether or not the target nucleic acid is present in the sample (a positive test line is indicative of the target nucleic acid being present in the sample). As the labeled chemically ligated product pass through the conjugation pad across the test and control lines, if the probes are chemically ligated (i.e., when the target nucleic acid being present in the sample), the test line shows a positive signal.

In some embodiments, an LFA comprises a colloid gold immunochromatography test strip comprising gold nanoparticles. The chemically ligated product bind to the gold nanoparticles in the conjugation pad. Gold nanoparticles flow through the reaction membrane and are captured by the antibodies (e.g., against an label on a probe) on the test line and control line regions. Finally, excess solution flows to the absorbent pad. In an LFA strip, all samples undergo a continuous reaction through a narrow reaction membrane, aggregating and concentrating in a specific area where receptors are coated. The whole process usually takes 3-15 minutes.

The immunochromatographic strips are typically coated with test and control line reagents and signal particles. The ligated product is captured by the test line reagents and reacted with the signal particles. The presence and/or amount of a signal generated by the capture of the ligated product can be determined by the naked eye, or detected by an instrument due to the appearance of a visual signal (e.g., a color change or the appearance of a test line).

The signal particles and detection conditions are preferentially selected such that the results can be easily observed by the naked eye. However, in some aspects, the results may be detected by an instrument (e.g., a scanner, a colorimeter, a fluorescence microscope, and the like). In some embodiments, no thermal cycling instrument is necessary. In some embodiments, immunochromatography-based detection is usually carried out within 5-10 min at room temperature.

In some embodiments, instead of the gold nanoparticles, the assay comprises carbon nanoparticles or colored latex nanoparticles to allow for visual inspection of the test and control line regions. The signal of the ligated product is determined by immunochromatography (e.g., LFA) is quantitatively related to the presence, amount, and/or concentration of target nucleic acid. In some embodiments, the ligated product already comprising the reporter molecules is captured and visualized.

In some embodiments, molecular diagnostic methods are simple two-step processes. The methods may take less than 10 minutes. In some embodiments, the methods are non-isothermal and/or isothermal amplification-free (amplification-free methods), i.e., no non-isothermal and/or isothermal amplification is required. In some embodiments, the disclosed diagnostic methods are two step processes. In some embodiments, they make take 10 minutes or less, for example 1 to 10 minutes. In some embodiments, the methods do not comprise the use of an enzyme, such as a polymerase or ligase. In some embodiments, the methods do not comprise PCR.

In some embodiments, the target nucleic acid sequence is not amplified prior to contacting the sample with the reaction mixture.

Third, the sample is applied to an immunochromatography strip for detection, wherein the sample will comprise ligated product if the target is present. In some embodiments, the presence of the ligated product produces a detectable signal on the immunochromatographic strip. A yes or no answer to the question of whether the target analyte is present in the sample is thus obtained through this diagnostic process.

In some embodiments, these molecular diagnostic methods (i.e., amplification-free methods) can be used in point-of-care and point-of-need scenarios. For example, the methods can be carried out quickly and inexpensively at bedside and/or in the field.

In some embodiments, the immunochromatographic analysis is performed at room temperature within 1 to 5 min of ligating the first probe and the second probe. In some embodiments of the method of determining the presence and/or level of an analyte in a sample, the immunochromatographic analysis is performed at room temperature within 5 to 10 min of ligating the first probe and the second probe. In some embodiments of the method of determining the presence and/or level of an analyte in a sample, the immunochromatographic analysis is performed at room temperature within 10 to 15 min of ligating the first probe and the second probe. In some embodiments of the method of determining the presence and/or level of an analyte in a sample, the immunochromatographic analysis is performed at room temperature within 15 to 20 min of ligating the first probe and the second probe. In some embodiments of the method of determining the presence and/or level of an analyte in a sample, the immunochromatographic analysis is performed at room temperature within 20 to 40 min of ligating the first probe and the second probe.

Combination of TARA-L with SDS-PAGE

In some embodiments, other methods for detecting and/or quantifying the chemically ligated product can be used. In some embodiments, probes are ligated to each other when they anneal in close proximity on a target nucleic acid, and the chemically ligated product are resolved and visualized on a gel. For example, the ligated product can be resolved and visualized by SDS-PAGE (sodium dodecyl sulfate-polyacrilymide gel electrophoresis) analysis. In some embodiments, one or more probes comprise a 5-FAM group, which allows for the assessment of ligation by SDS-PAGE.

In some embodiments, TARA reaction can be carried out using 0.4 µM probes and template for direct viewing by 16% SDS-PAGE. The denaturing properties of the SDS-PAGE gel allows a band shift to be detected only when the probes are chemically ligated to each other and not when the probes do not undergo chemical ligation.

In some embodiments, the G probe (anneals downstream of the A probe on the target nucleic acid) is blocked at the 5' end with 5-FAM, which doubles as a reporter molecule for direct viewing of bands in the SDS-PAGE gel as well as prevents non-specific reactions.

In some embodiments, the TARA-L reaction can stop using a 'STOP' solution. In some embodiments, the 'STOP' solution comprises 95% formamide, 5 mM EDTA (ethylenediaminetetraacetic acid).

In some embodiments, when using SDS-PAGE analysis, the TARA-L reaction can stop using a 'STOP' solution. In some embodiments, the 'STOP' solution comprises 95% formamide, 5 mM EDTA (ethylenediaminetetraacetic acid) as well as 0.25 mg/ml bromophenol blue. In some embodiments, the STOP solution comprising bromophenol blue is added in a 1:1 (v:v) ratio to each reaction to halt the TARA reaction and doubles up not only as a 'STOP' solution but also as a loading dye for SDS-PAGE analysis.

In contrast, such non-specific G-G probe ligations would not appear on LFA strips that are designed to detect dual-labelled ligation products (e.g., Biotin-FAM dual-labels). The labels not only prevent non-specific ligation, they also allow for specific detection of the ligated product on the LFA strips.

Figure 6:
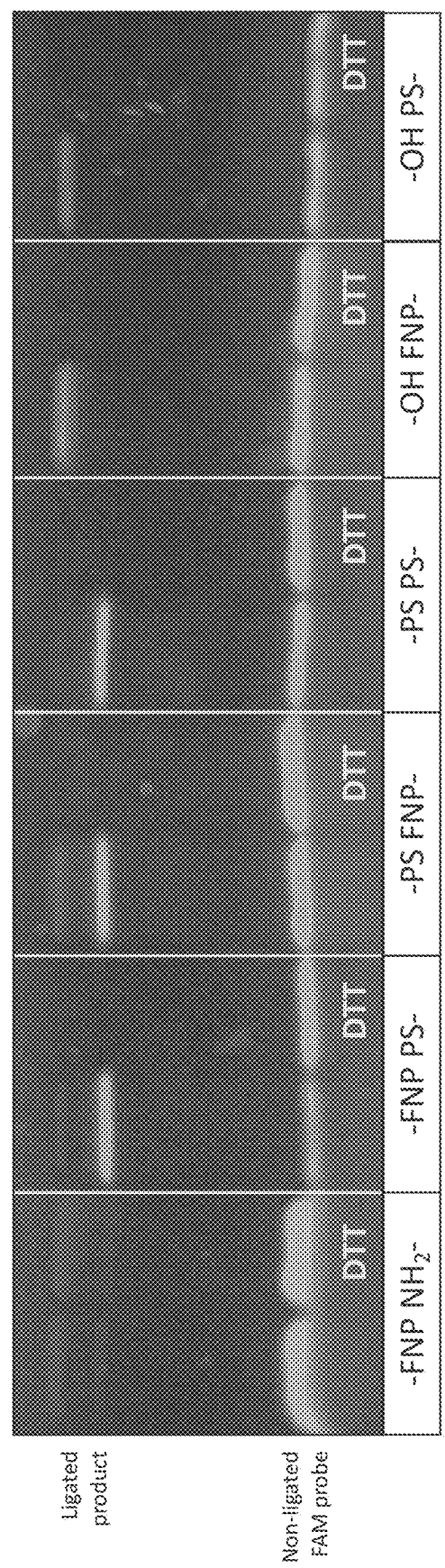
FIG. 6 shows TARA-L chemistry ligation tests with and without reducing agent (DTT). TARA-ligation tests were run as 50-μl reactions containing 0.4 μM probes and template (synthesized complementary DNA to probe sequences), with or without 1 mM DTT in 10 mM Tris buffer (pH 8.0). TARA-ligation reaction conditions were 55° C. for 15 min. Samples were mixed 1:1 v:v with 'STOP' solution containing 95% formamide, 5 mM EDTA and 0.25 mg/ml bromophenol blue, heated to 95° C., and then loaded onto a 16% SDS-PAGE gel at 30 μl per well. Results show that ligation was disrupted in all the tested chemistries, except chemistry pair 1 (—FNP NH$_2$—), when the reducing agent DTT was added to the reaction. SIA chemistry was not included, as DTT was already present in the SIA reaction buffer.

Without being limited by any particular theory, reactions between PS and PS (Chemistry Pair #6 in Table 2) are known to produce disulfide bonds (S—S) that can be broken using reducing agents. In some embodiments, TCEP and DTT can be used to test if reaction products can be disrupted using reducing agents. Thus, in some embodiments, the inhibitor may be, for example, DTT or TCFP. In some embodiments, for chemistry pairs 2-4, 6 and 8 an inhibitor such as DTT (FIG. 6) or TCEP is used, and for some chemistry pairs, such as 1 and 9, in some embodiments no inhibitor is used.

In some embodiments, SDS-PAGE allows for separation of unligated labeled probes from labeled ligated products. In some embodiments, SDS-PAGE allows for separation of unligated labeled probes from labeled ligated products and visualization of the labelled ligation products (e.g., FIGS. 5, 6 and 7A). In some embodiments, SDS-PAGE allows for separation of unligated labeled probes from labeled ligated products and visualization of both unligated labeled probes and the labelled ligation products (e.g., FIGS. 5, 6 and 7A).

In some embodiments, the labeled ligated products are purified before visualization by SDS-PAGE. In some embodiments, the labeled ligated products are purified before visualization by SDS-PAGE such that only the labeled ligated products are visualized only SDS-PAGE and not unligated labeled probes.

Combination of TARA-L with LAMP

In some embodiments, different primer schemes can be used, for example, to facilitate amplification after formation of the chemically ligated product. For example, primers can be designed that allow for LAMP amplification after annealing and ligation. In some embodiments, disclosed herein are probes that combine TARA chemistries with the LAMP for highly specific and sensitive detection of target analytes. Also provided are methods for highly specific and sensitive detection of target analytes using TARA-L-LAMP probes (described in Notomi, T., Okayama, H., Masubuchi, H., Yonekawa, T., Watanabe, K., Amino, N., et al. (2000). Loop-mediated isothermal amplification of DNA. Nucleic Acids Res., 28, e63; Nagamine, K., Hase, T., & Notomi, T. (2002). Accelerated reaction by loop-mediated isothermal amplification using loop primers. Mol. Cell. Probes, 16(3), 223-229; Mori, Y., & Notomi, T. (2009). Loop-mediated isothermal amplification (LAMP): a rapid, accurate, and cost-effective diagnostic method for infectious diseases. J. Infect. Chemother., 15, 62-69, which are incorporated by reference in their entireties).

In some embodiments, TARA probes are designed specifically to be used directly with downstream LAMP assays through the creation of synthetic dumbbell-loop structures, which are attached to the 5'- and 3'-ends of the G and A probe target sequences, respectively. These 'universal' LAMP adapters are designed from purely randomized synthetic sequences and chosen to include all portions of a LAMP dumbbell, while meeting the suggested parameters for proper LAMP assay performance (e.g., FIG. 17A).

In some embodiments, TARA-L-LAMP probe target sequences are chosen to specifically anneal to a desired nucleic acid target. Non-limiting examples include specific viral DNA/RNA, specific bacterial DNA/RNA, specific fungal DNA/RNA and/or specific parasite DNA/RNA.

In some embodiments, nucleotides are added between the LAMP adapters and the probe target sequences such that they have complementary base pairing with the distal end of the target sequence, thus promoting secondary hairpin stem-loop formation.

Figures 18A, 18B:
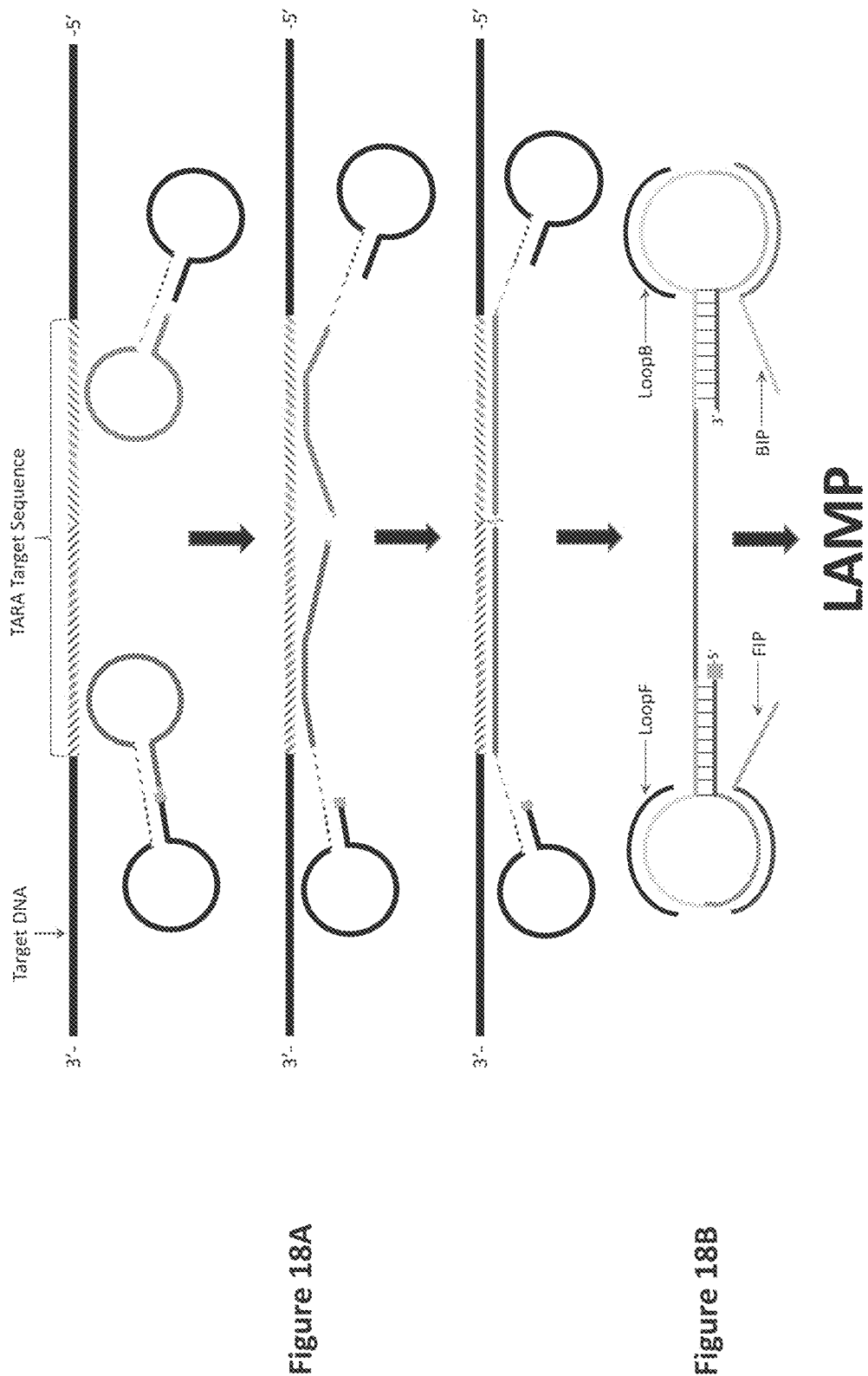
FIGS. 18A-18B show a schematic of a TARA-L-LAMP probe ligation reaction according to some embodiments.

In some embodiments, in the presence of a target molecule with complementary sequence to the probes, the stem-loops preferentially bind/anneal, open and allow the reactive ends to come into proximity to allow ligation (e.g., FIG. 18A). The 'universal' LAMP adapters produce a product, upon proper ligation, that can be directly amplified using LAMP (FIG. 18B). This product essentially represents the first dumbbell loop structure created during a LAMP reaction, therefore the outer primers (F3/B3) required by a standard LAMP reaction can be omitted, as they are only required to assist in creating the initial dumbbell loop structure. The subsequent LAMP reaction of the TARA-L-LAMP assay requires only four primers, the 'universal' inner (FIP/BIP) and loop (LF/LB) primers (e.g., FIG. 18B). Loop primers are tagged, for example with biotin and FAM/FITC, allowing results to be viewed by a simple lateral flow strip. In some embodiments, in addition to the reduced primer requirement, starting with the prefabricated dumbbell loop structure provides a significant speed advantage. Given that amplification and reproduction of the dumbbell loop structure during LAMP will begin immediately, not having to organically build the initial dumbbell loop structure using primers reduces reaction time.

In some embodiments, the TARA-L-LAMP probe design comprises G and A probes that comprise a pair of reactive groups at their 3'- and 5'-ends, respectively.

In some embodiments, a synthetic DNA template can be used to represent the "target" sequence that would be present in a DNA/RNA molecule of interest, for example, when reaction conditions are to be optimized prior to testing a patient sample.

In some embodiments, probes are activated with either FNP or SIA and then heated (e.g., to 90° C. for 5 min) and cooled (e.g., at −20° C.) to induce secondary structures designed into the 'universal' LAMP adapters, as well as the probe target sequences.

In some embodiments, the TARA-L-LAMP probes can be used in ligation reactions under different conditions. For example, the reaction times can range from about 5-20 min, the temperature can range from about 55-75° C., and the probe concentration can be varied.

Figure 19:
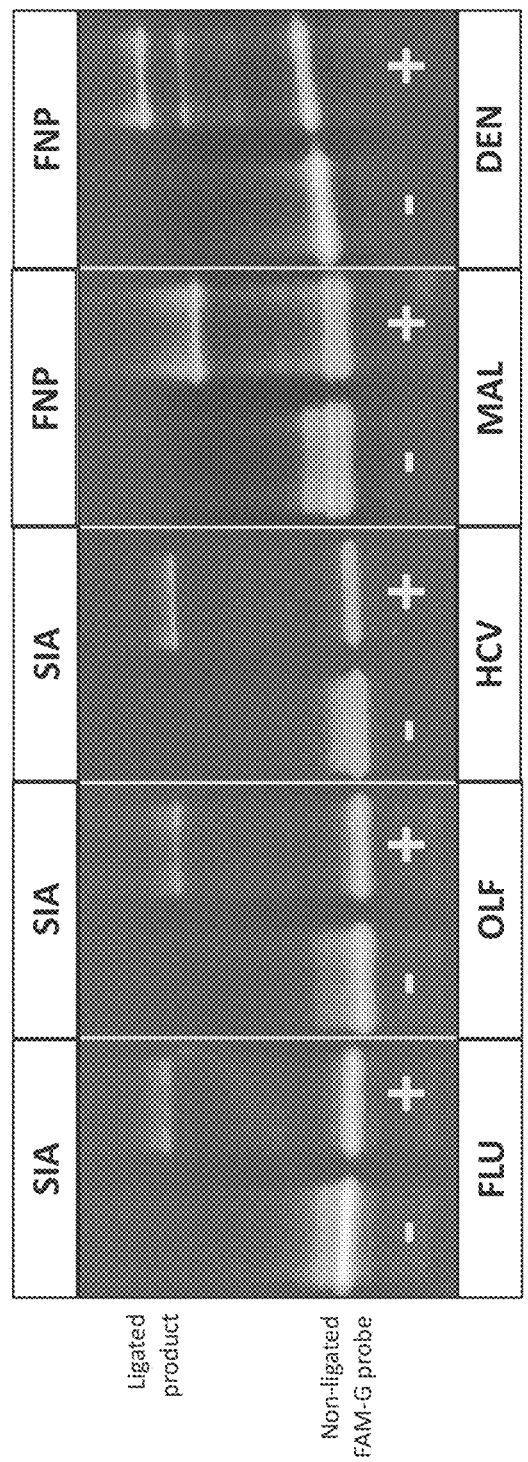
FIG. 19 shows SDS-PAGE analyses of TARA-L-LAMP ligation. Probes for influenza A (FLU), hepatitis C virus (HCV), Opisthorchiid liver flukes (OLF), malaria (MAL) and dengue virus (DEN) were synthesized, activated with either SIA or FNP, heat/cooled to initiate proper folding, and then reacted in ligation reactions. TARA reactions were analyzed using SDS-PAGE to demonstrate true ligation, as annealed probes would not show a band shift because the SDS-PAGE creates single stranded molecules. G-probes were labelled with FAM at the 5'-end for direct viewing of the results under UV illumination. Results show that for all target sequences tested and for both SIA and FNP chemistries, ligation occurred as predicted (positives; +), and no observable ligation occurred in TARA reactions without template (negative; −).

An example of the successful design of TARA-L-LAMP probes is provided in FIG. 19. In an SDS-PAGE analysis, a band suggesting proper ligation of the FAM-labelled G probe with the A probe can be seen in "positive" samples, while no band was observed in the "negative" samples (e.g., FIG. 19).

Figures 20A, 20B:
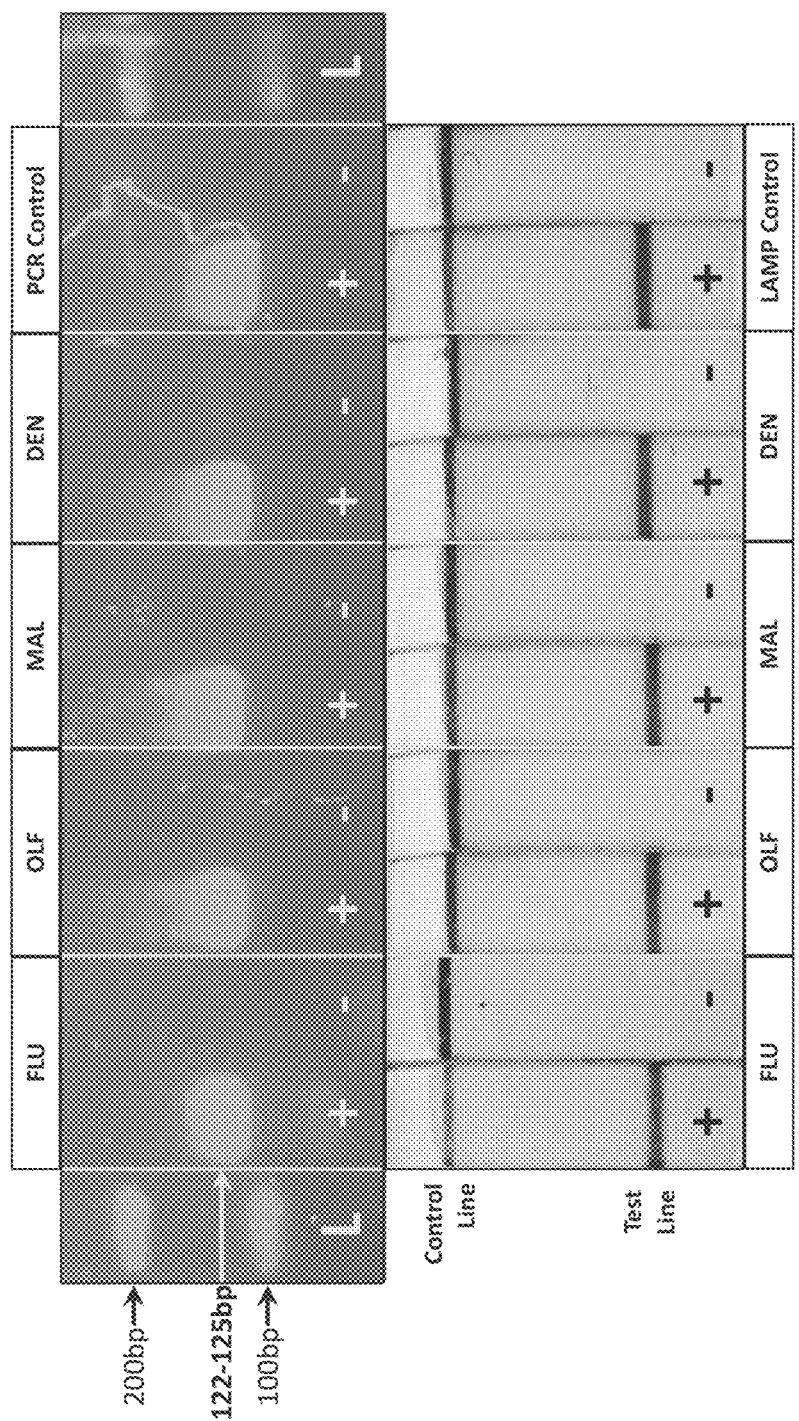
FIGS. 20A-20B show PCR and LAMP tests using SDS-PAGE gel-extracted 'ligated' product.

In some embodiments, proper probe ligation was shown by ligating the probes and resolving them on SDS-PAGE, extracting the ligated product from the SDS-PAGE gel, amplifying the ligated product by PCR and LAMP, and testing the amplified probes by LFA (FIGS. 20A and 20B).

Thus, in some embodiments, the hairpin stem-loop structures added into probe target sequences are valuable and useful in preventing non-specific ligation.

In some embodiments, one temperature is used for the TARA ligations reactions step and a second temperature is used for the LAMP assay. In some embodiments, a single temperature is used for both the TARA ligation and LAMP assay. In some embodiments, a single temperature is used for the entire TARA-L-LAMP assay. In some embodiments, a TARA-ligation reaction temperature is 65° C. as this is the operating temperature of the downstream LAMP, allowing a single temperature to be used for the entire TARA-L-LAMP assay. In some embodiments, the temperature can range from about 62.5° C. to about 67.5° C.

In some embodiments, the rapidity of the newly designed TARA-L-LAMP probe ligation reaction significantly shortens the overall reaction time (time-to-positive, i.e., time to see a positive result). In some embodiments, the reaction time is relatively shorter compared to assays such as PCR and/or assays involving long sample preparation steps. In some embodiments, the rapidity of the newly designed TARA-L-LAMP probe ligation reaction significantly shortens the overall reaction time (time-to-positive), which is ideal for POC testing, for example, where rapid and accurate testing of analytes from a biological sample collected directly (i.e., without further processing of the sample) from a patient is desired. In some embodiments the sample is analyzed without preparation. Non-limiting examples for which rapid and accurate testing of analytes from a biological sample may be required include situations where a biological sample is collected for blood glucose testing, blood gas and electrolytes analysis, rapid coagulation testing, rapid cardiac markers diagnostics, drugs of abuse screening, urine strips testing, pregnancy testing, fecal occult blood analysis, food pathogens screening, hemoglobin diagnostics, infectious disease testing and cholesterol screening.

In some embodiments, LAMP assays can be performed using mock 'ligated' product as the target molecule, for example, when reaction conditions are to be optimized prior to testing a patient sample. For example, G and A probe sequences can be synthesized as single DNA molecule. The synthetic target molecule can be heated (e.g., to 90° C. for 5 min) and cooled (e.g., at −20° C.) to induce secondary structures designed into the 'universal' LAMP adapters. In some embodiments, reaction conditions can be determined using the synthetic target molecule in LAMP assays using different concentrations to establish a base-level sensitivity, as well as different reaction times to determine the minimum time required to maintain sensitivity. In some embodiments, the LAMP-reaction master mix comprises 1.6 µM FIP/BIP, 0.8 µM LF/LB, 1×IsoAmp buffer (New England Biolabs), 6 mM additional (8 mM total) $MgSO_4$, 1.4 mM dNTPs, 320 U/ml Bst 2.0 (New England Biolabs), and water to a 20 µl volume per reaction.

In some embodiments, LAMP can consistently and rapidly amplify as little as 150 copies of target molecule for viewing on a lateral flow strip. In some embodiments, LAMP can consistently and rapidly amplify fewer than 150 copies of target molecule for viewing on a lateral flow strip. In some embodiments, LAMP can consistently and rapidly amplify as little as 150 copies of target molecule for viewing on a lateral flow strip following a LAMP reaction for 10 minutes at 65° C. (e.g., FIG. 21). In some embodiments, the minimum number of copies that LAMP can amplify ranges from about 75 to about 150. In some embodiments, the minimum number of copies that LAMP can amplify is about 75, 80, 85, 90, 95, 100, 105, 110, 115, 120, 125, 130, 135, 140, 145, or 150. In some embodiments, the minimum number of copies that LAMP can amplify can be fewer than 75.

In some embodiments, the combination of TARA-L-LAMP can work for POC testing with results determined in around 15-20 minutes total time. In some embodiments, the combination of TARA-L-LAMP can provide results in around 5-10 minutes total time. In some embodiments, the combination of TARA-L-LAMP can provide results in around 10-15 minutes total time.

In some embodiments, based on the sensitivity of the downstream LAMP assay and a workflow combining TARA-L and LAMP steps (e.g., perform a 50-µl TARA-ligation reaction and then take 5 µl completed TARA as the sample for the LAMP assay), the upstream TARA reaction should have about 1,500 copies of template/target to be present in the 50-µl TARA-ligation reaction to be detectable by a 10-min downstream LAMP reaction and lateral flow assessment).

In some embodiments, by decreasing the volume of the upstream TARA-ligation reaction, to a 25-µl reaction for example, the copies required by the TARA-ligation reaction would decrease to 750 copies. In some embodiments, decreasing the amount of water in the LAMP-reaction master mix to make it 15 µl per LAMP reaction and use 10 µl of TARA-ligation reaction to maintain the 25-µl total LAMP-reaction volume would decrease the copies required in a 50-µl TARA-ligation reaction to 750 copies. In some embodiments, further decreasing the volume of the TARA-ligation reaction, to a 25-µl reaction for example, would decrease the copy requirement to 375 copies. Similarly, the LAMP-reaction volume could be increased to 50 µl and 10 µl or more of the TARA-ligation reaction could be added, thus decreasing the upstream copy requirement.

Figure 26B:
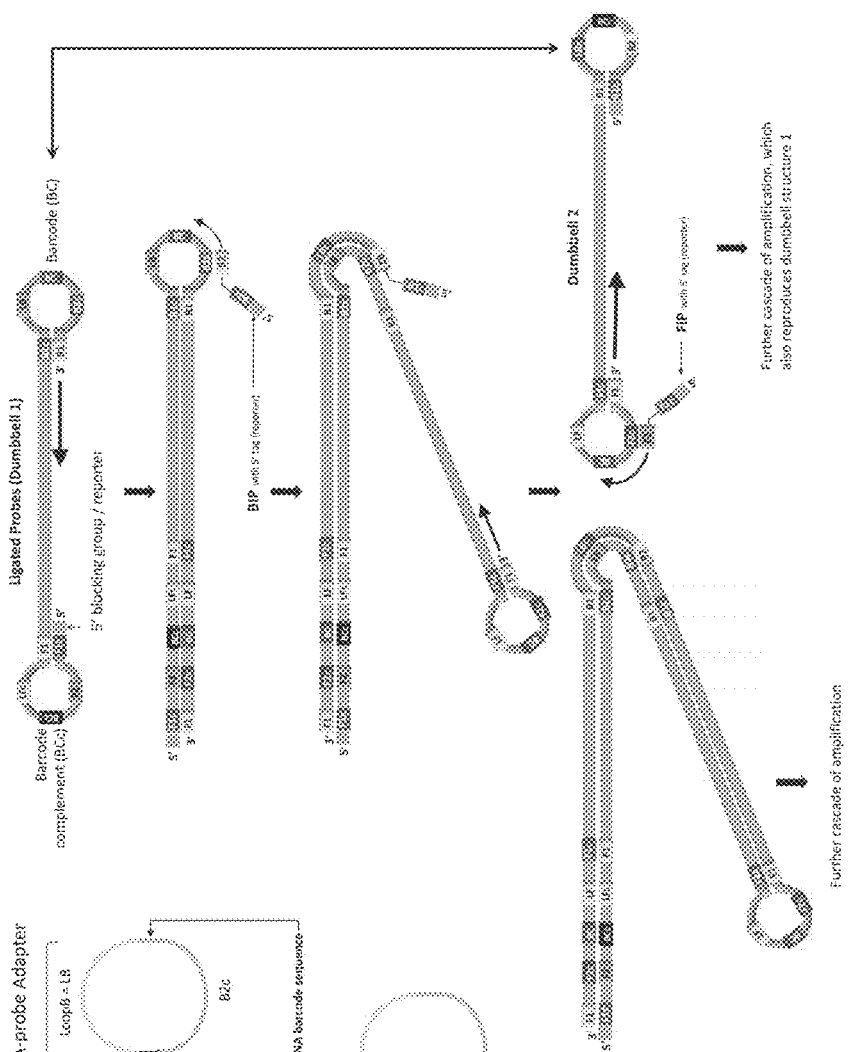
FIGS. 26A-26B show TARA-L-LAMP probe design for multiplexing and the early LAMP cascade products for detection.
Figure 26A:
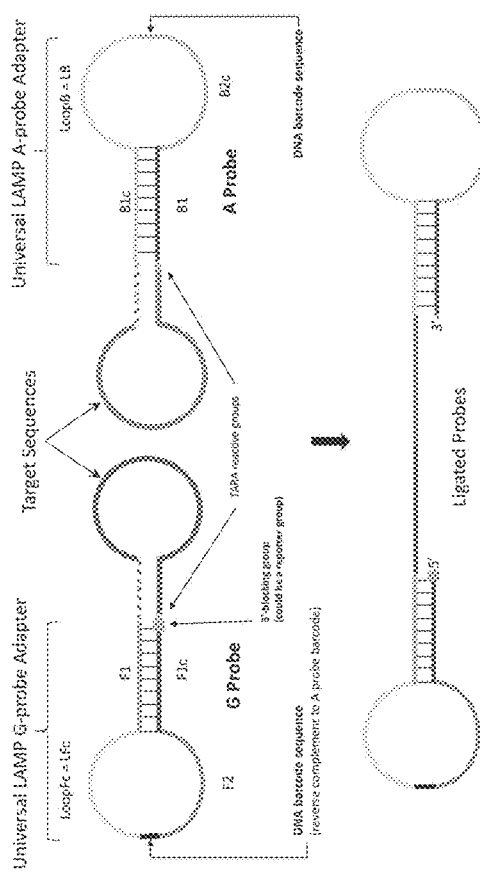

In some embodiments, TARA-L-LAMP probes are designed for multiplexing (e.g., FIG. 26A). In some embodiments, probe sets are designed to detect different targets. In some embodiments, probe sets designed to detect different targets have their own unique barcode sequences.

In some embodiments, different 5'-blocking groups (e.g., 5-FAM) can be used as labels to provide multiplexing capabilities by capture and signal reporting.

In some embodiments, a barcoding sequence can be added between the two primers sequences within the single stranded region of the dumbbell stem-loop for one or both probes, thus allowing for probe capture, as well as have applications in multiplexing, for example, by allowing you to identify particular ligated products. In some embodiments, probe capture can occur before running the LAMP reaction to capture the probes themselves and ligated products. In some embodiments, probe capture can occur after the LAMP reactions to capture the LAMP reaction products.

In some embodiments, different ligand pairs can be used in the same sample to test for different targets, with the different ligand pairs including markers that allow for separate identification, such as barcode sequences In some embodiments, barcoding can also be used in conjunction with labeled primers (e.g., LF, LB, FIP and BIP) to provide multiplexing capabilities by capture and signal reporting. In some embodiments, the location of the barcoding sequences is specific to LAMP and the probe structures. In some embodiments, the number and/or location of the barcoding sequences is specific to LAMP and fixed in the probe structures. In some embodiments, the number and/or location of the barcoding sequences is specific to LAMP and variable in the probe structures. In some embodiments, the number and/or location of the barcoding sequences are variable in the probe structures and can be combined with other multiplexing methods.

In some embodiments, one or both loop primers (LF/LB) are labeled with a reporter selected from a group consisting of, but not limited to, Biotin, FITC, FAM and digoxin.

In some embodiments, one or both inner primers (FIP/BIP) are labeled with a reporter selected from a group consisting of, but not limited to, Biotin, FITC, FAM and digoxin.

In some embodiments, one or more primers are labeled with a reporter selected from a group consisting of, but not limited to, Biotin, FITC, FAM and digoxin, to be used for product capture.

In some embodiments, one or more primers are labeled with a reporter selected from a group consisting of, but not limited to, Biotin, FITC, FAM and digoxin, to be used for multiplexing.

In some embodiments, the G probe adapters are blocked at the 5' end.

In some embodiments, the G probe adapters are blocked at the 5' end with a blocking group selected from a group consisting of, but not limited to, Biotin, FITC, FAM, phosphate and C3-spacer.

In some embodiments, the 5'-blocking group of the G probe is one or more of Biotin, FITC, FAM, phosphate and C3-spacer.

In some embodiments, the 5'-blocking group of the G probe is used for probe capture.

In some embodiments, the 5'-blocking group of the G probe is used for multiplexing.

In some embodiments, one or more probes contain 'universal' or specific adapter sequences containing an additional barcoding sequence.

In some embodiments, one or more probes contain 'universal' or specific adapters sequences containing an additional barcoding sequence used for probe capture.

In some embodiments, one or more probes contain 'universal' or specific adapters sequences containing an additional barcoding sequence used for multiplexing.

In some embodiments, the barcoding sequence used for multiplexing is 5-10 nucleotides. In some embodiments, the barcoding sequence used for multiplexing is 10-15 nucleotides. In some embodiments, the barcoding sequence used for multiplexing is 15-20 nucleotides.

In some embodiments, the barcode sequence is captured by an oligonucleotide UV-crosslinked to a membrane. In some embodiments, the barcode sequence is captured by an oligonucleotide containing a label that binds to a ligand that is bound to a membrane.

In some embodiments, the capturing oligonucleotide is comprised solely of the barcode complement sequence. In some embodiments, the capturing oligonucleotide is comprised of the barcode and some probe stem-loop complement sequences.

In some embodiments, using different 5'-blocking groups as labels and/or adding a barcoding sequence between the two primers sequences within the single stranded region of the dumbbell stem-loop for one or both probes allows for probe capture, as well as have applications in multiplexing.

In some embodiments, LAMP assays can be tested for any potential and possible inhibition by biological samples (e.g., blood, saliva, or urine sample). This is important in the context of providing POC testing of samples directly collected (without further processing) from a patient. In some embodiments the sample is analyzed without preparation. For example, in some embodiments, mock 'TARA' samples can be prepared by adding 30,000 copies of mock 'ligated' product to 50-μl reactions (1 fM) containing as much as 15 μl saliva, blood plasma or urine (30% total), or 15 μl 10% BSA (4% total). In some embodiments, LAMP reactions can also be tested for inhibition by the harsh lysis buffer conditions of CLBuffer-1 and CLBuffer-2. These spiked samples can be tested by LAMP, for example, using about 5 μl of mock 'TARA' sample (i.e., about 3,000 copies per LAMP reaction). Non-limiting examples are shown in FIGS. 22A-22D, which represent one set of experiments to test the effect of lysis buffer and biological material on LAMP performance.

In some embodiments, inhibitory effects of harsh conditions (e.g., lysis buffers) or inhibitory factors in biological samples/materials can be can be negated by increasing the reaction time, reaction volume, or both. In some embodiment, increasing the reaction time alone is sufficient. In some embodiment, increasing the reaction volume alone is sufficient. In some embodiment, both the reaction time and volume may have to be adjusted. For example, for urine samples and when using CLBuffer-1, increasing the reaction time or reaction volume was able to negate the inhibitory effects (e.g., FIGS. 22A-22D)

In some embodiments, addition of a ligated product capture and wash step can be used to remove any inhibitory factors before performing a downstream LAMP assay.

In some cases, the designed TARA-L-LAMP G and A probes both comprise at least one LAMP-primer binding site, and the A probe structure allows 3' extension and possible amplification in a manner similar to a normal LAMP reaction. As a result, real-time analysis of TARA-L-LAMP is not feasible due to the potentially non-specific amplification of individual probes masking the amplification of true ligated TARA probes. However, in these cases, rt-LAMP-based assessment of 'ligated' product is possible due to the absence of probes and the absence of potentially non-specific amplification of individual probes.

Thus, in some embodiments, non-specific amplification by the A probe is limited by by addition of a 3'-blocking group. In some embodiments, a mock 'ligated' product with a 3'-phosphate as the blocking group on the A probe end can be used. This mock 'ligated' product would represent ligation between the G probe and 3'-blocked A probe. However, using a 3'-blocked may result in a decrease in reaction speed/sensitivity as compared to using unblocked probe (e.g., FIG. 23). Thus, while 3'-blocking of the A probe is possible, the sensitivity may be affected. However, sensitivity can be restored by increasing the reaction time.

Figure 24:
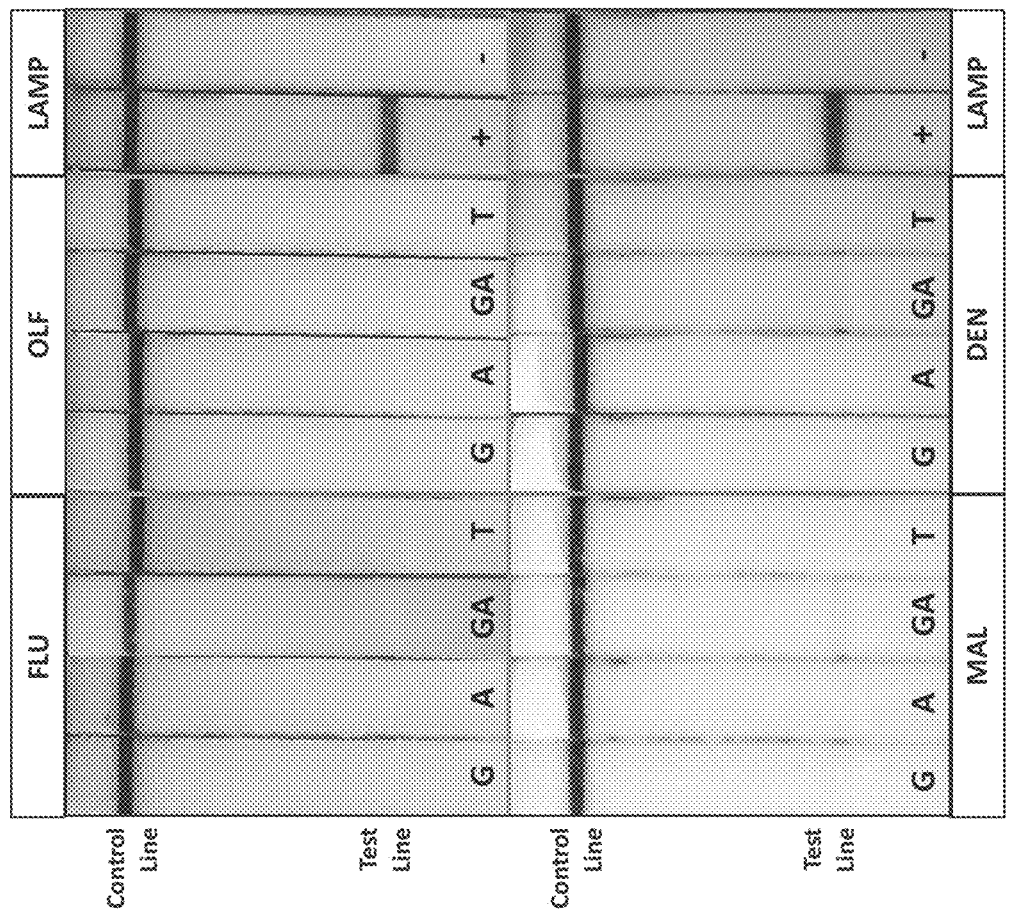
FIG. 24 shows TARA-L-LAMP control tests. LAMP reactions were performed on G probe alone (2 nM), A probe alone (2 nM), G and A probe mixture (2 nM each), or TARA-L-LAMP probe template alone (200 nM), for each of FLU, OLF, MAL and DEN. LAMP reactions were compared to a LAMP positive control (1 fM mock 'ligated' product) and LAMP negative control (water). No non-specific amplification reactions were observed in all controls tested by lateral flow strip; only the positive control showed a positive test line.

In some embodiments, the probes as designed (without blocking the 3' end of the A probe) do not result in any non-specific amplification in the absence of a target molecule (e.g., FIG. 24).

In some embodiments, the designed TARA-L-LAMP G and A probes both comprise at least one LAMP-primer binding site, and the A probe structure allows 3' extension and possible amplification in a manner similar to a normal LAMP reaction. In some embodiments, the LAMP assays may be potential inhibited by the presence of probes in the LAMP reaction due to competition with the ligated product for reagents and/or primers (e.g., FIG. 25). Thus, in some embodiments, in order to avoid any inhibition of the LAMP assays due to probes competing for LAMP reagents and primers, the concentration of both G and A probes are around 10 pM.

In some embodiments, a capture and wash step prior to the LAMP assay is preferable to reduce/eliminate all potential forms of LAMP inhibition.

In some embodiments, the capturing one of the probes, and thereby also capturing the ligated product, and washing away the other, is another means of reducing/preventing any potential inhibition by the probes competing for reagents/primers.

In some embodiments, the capture step can be performed in a variety of ways. Non-limiting examples include antibody-, avidin-, or nucleic acid-coated areas on a solid surface like a lateral flow strip, antibody-, avidin-, or nucleic acid-coated tubes or antibody-, avidin-, or nucleic acid-coated magnetic beads.

In some embodiments, unique barcode sequences are inserted between the LB and B2c sequences located in the single-stranded loop portion of the A probe. Corresponding reverse complement sequences are inserted between the F2 and LFc sequences located in the single-stranded loop portion of the G probe. The ligated product produces a dumbbell structure 1 (FIG. 26A). In some embodiments, early in the LAMP amplification cascade, LAMP amplification of dumbbell structure 1 by BIP primers 5'-tagged with a reporter generate dumbbell structure 2, as well as a larger more complex product (FIG. 26B). The larger product continues in the LAMP cascade to produce complex products of increasing size and complexity. Dumbbell structure 2 contains the 5' reporter and barcode sequence in the 3' end stem loop. LAMP amplification of dumbbell structure 2 by FIP primers 5'-tagged with a reporter regenerate dumbbell structure 1, as well as a larger more complex product that is essentially the reverse complement of the one produced by dumbbell structure 1 (FIG. 26B). This larger product also continues in the LAMP cascade to produce complex products of increasing size and complexity. All products with a 5' reporter tag and a barcode sequence located in a single-stranded loop region are detectable by lateral flow assay. Specific oligonucleotides complementary to each unique barcode sequence allow selective capture of specific products within the lateral flow strip for multiplexing.

TARAplex

In some embodiments, an automated device using which all aspects of the detection methods described herein can be carried out. The automated device provides an automated workflow (referred to herein as TARAplex) for sensitive and specific detection of target nucleic acids based on TARA-L. TARAplex can further comprise downstream steps with or without the need for enzymes (e.g., for amplification).

Figure 2:
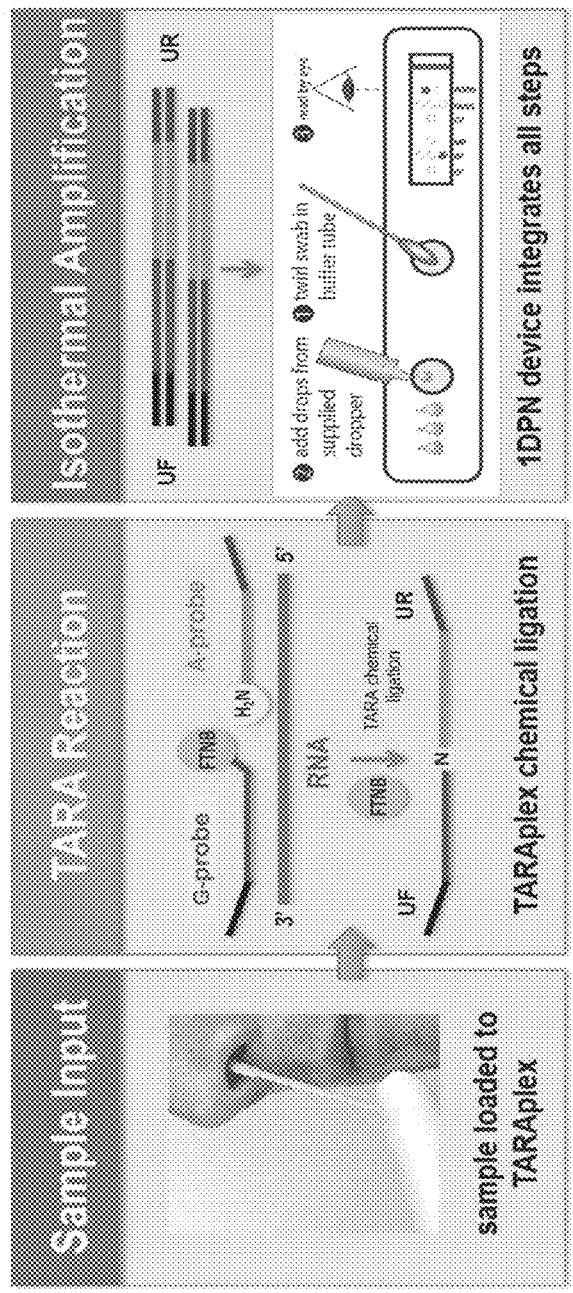
FIG. 2 shows an example of a workflow for analysis of a sample for respiratory pathogens using TARAplex chemical ligation followed by isothermal amplification. All steps of the analysis can be integrated in a 1-Dimensional Paper Network (1DPN) device.

A sample-to-answer workflow of a TARAplex is shown in FIG. 2A sample, such as a patient nasopharyngeal swab sample, is placed into CLBuffer, which lyses viruses or bacteria and stabilizes the nucleic acids, such as RNA and/or DNA. Two chemically-reactive probes hybridize to target sequence within a target nucleic acid, and undergo a rapid covalent chemical reaction without enzymes, resulting in ligation of two probes into a single probe with two universal primer sites. Isothermal amplification is used to amplify all ligated products using a single primer set. Amplicons can be captured at spots on a paper, for example by using barcode capture molecules for each target. Results can be read as visible dots or lines that are present when the analyte is present in the sample.

TARAplex can provide primary care doctors, outpatient pulmonary doctors, hospitalists, technicians and others a rapid (e.g., 30 minute), instrument-free, one-off, easy-to-use, accurate, stream-lined, point-of-care, and multiplexed test to identify analytes of interest, such as in a patient sample. For example, a doctor may be able to detect the presence of respiratory pathogens that cause upper respiratory tract infections.

Figure 3:
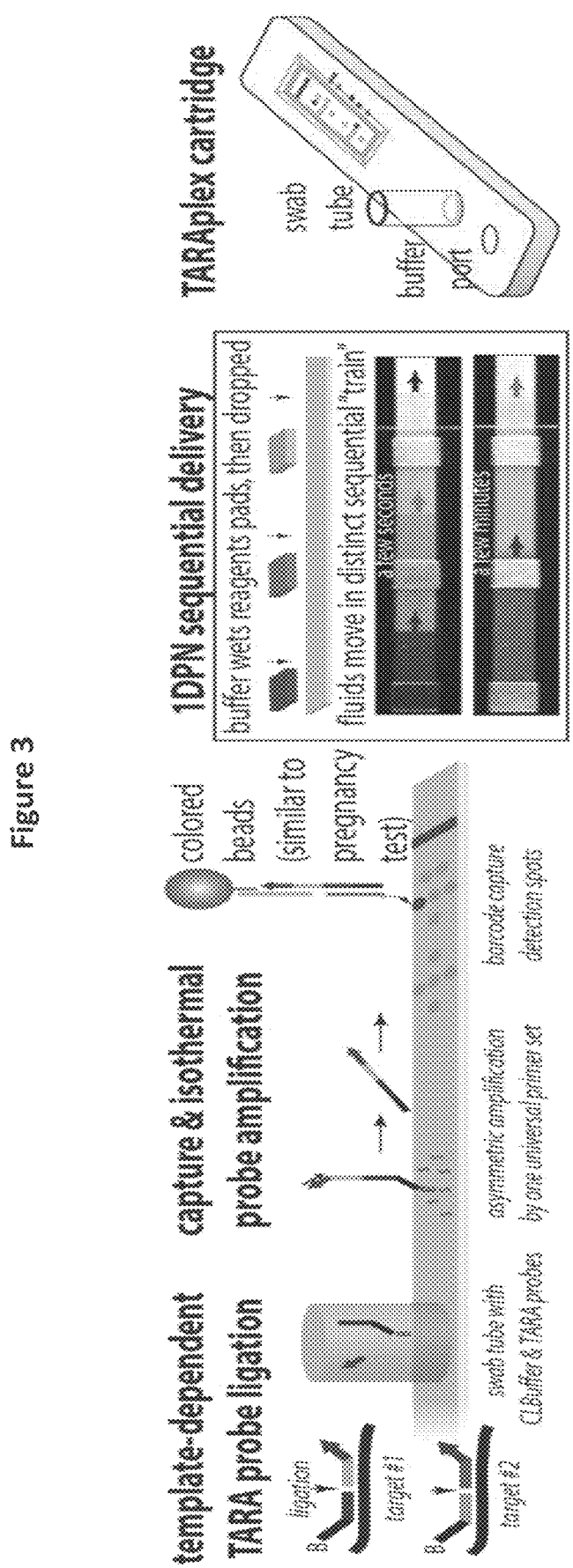
FIG. 3 shows an example of TARAplex automation based on sequential delivery in a 1-Dimensional Paper Network (1DPN) according to some embodiments. The left panel shows core processes for TARA probe ligation of a sample prepared in a swab tube, amplification, and detection. Capture of TARA ligated product and unreacted G-probes on paper allows for removal of unreacted and uncaptured A-probes prior to amplification. Amplicons are free to flow for detection in paper strips, such as by barcode capture. The middle panel shows demonstration of sequential delivery based on wicking in paper. Glass fiber pads with dyes represent dried reagents that are rehydrated with buffer before use; when these sources contact the paper strip, each fluid is released into the paper in an orderly sequence through the reaction zone to the detection line. The right panel shows that all processes from swab input to detection can be integrated into a simple cartridge (TARAplex cartridge) that may comprise low-cost heaters. A single buffer port can be used to distribute buffer to dry reagent pads.

In some aspects, detection methods can be implemented in a microfluidic device (lysis, TARA reaction, isothermal amplification, detection). In some aspects, detection methods can be implemented in a TARAplex, automated paper device (lysis, TARA reaction, isothermal amplification, detection). Low-cost paper-microfluidic devices are provided for instrument-free TARA-L, capture, amplification, and detection. The TARA-L chemistry allows all steps of the diagnostic methods to be automated in a paper device using dried reagents and minimal user steps. Further, paper devices can capture TARA probes, which concentrates the probes and allows for removal of non-reacted probes, for example prior to amplification. The integrated system illustrated in FIG. 3 involves 1) simultaneous lysis and TARA-L probe reaction, for example in CLBuffer, 2) capturing reacted TARA-L probes, such as by biotin labelling (allowing sample components and unreacted A-probe with primer sites to flow through to waste), 3) flowing isothermal amplification reagents across the captured TARA-L probes, and 4) detecting amplicons on spots using, for example, colored label detection. These sequential steps are made possible by a paper-microfluidics effect that allows delivery of multiple reagents in a timed sequence through paper strips in a device referred to as the 1-Dimensional Paper Network (1DPN). Reagents are stored in a dry shelf-stable form on pads; the user adds buffer to the device, and rehydrated reagents are delivered one-by-one across the reaction zone (FIG. 3 middle). Temperature control is provided by a low-cost heater inside the disposable device, as in the multiplexable autonomous disposable nucleic acid amplification test (MAD NAAT) platform (FIGS. 4A-4C). Engineered detection probes allow freedom to report pathogens as separate spots or to combine several pathogens (e.g., parainfluenza types) into a single spot for simplified reporting.

In some embodiments, a device for diagnosing a condition in a subject is provided. Embodiments of the device utilize the embodiments of the method of diagnosing a condition in a subject provided herein.

In some embodiments, the device is a TARAplex, automated 1DPN paper device.

In some embodiments, the device is a microfluidic device.

In some embodiments of the method of diagnosing a condition in a subject, the condition is associated with a pathogen selected from a group consisting of, but not limited to, bacteria, fungi, viruses, and parasites.

In some embodiments of the method of diagnosing a condition in a subject, the condition is associated with a pathogen that is one or more of a bacterium, a fungus, a virus, and/or a parasite.

In some embodiments of the method of diagnosing a condition in a subject, the virus is selected from the group consisting of, but not limited to, dengue virus, influenza virus, chikungunya virus, the human immunodeficiency virus (HIV), the hepatitis C virus (HCV), human papillomavirus (HPV), Middle East respiratory syndrome (MERS) virus, arboviruses, respiratory syncytial virus (RSV; also known as human orthopneumovirus) and Ebola virus.

In some embodiments of the method of diagnosing a condition in a subject, the virus is one or more of dengue virus, influenza virus, chikungunya virus, the human immunodeficiency virus (HIV), the hepatitis C virus (HCV), human papillomavirus (HPV), Middle East respiratory syndrome (MERS) virus, arboviruses, respiratory syncytial virus (RSV; also known as human orthopneumovirus) and Ebola virus.

In some embodiments of the method of diagnosing a condition in a subject, the bacterium is, but not limited to, methicillin-resistant *Staphylococcus aureus* (MRSA).

In some embodiments of the method of diagnosing a condition in a subject, the parasite is selected from the group consisting of, but not limited to, *Plasmodium falciparum* (malaria), *Candida auris* and Opisthorchiid liver flukes consisting of *Opisthorchis sinensis* (also known as *Clonorchis sinensis*), *Opisthorchi viverrini* and *Opisthorchis felineus*. Other parasites are also contemplated.

In some embodiments of the method of diagnosing a condition in a subject, the parasite is one or more of *Plasmodium falciparum* (malaria), *Candida auris* and Opisthorchiid liver flukes consisting of *Opisthorchis sinensis* (also known as *Clonorchis sinensis*), *Opisthorchi viverrini* and *Opisthorchis felineus*.

In some embodiments of the method of diagnosing a condition in a subject, the target nucleic acid is selected from the group consisting of, but not limited to, RNA, DNA, and microRNA.

In some embodiments of the method of diagnosing a condition in a subject, the target nucleic acid is one or more of RNA, DNA, and microRNA.

In some embodiments, a method of diagnosing a condition in a subject comprises obtaining a sample from the subject that may comprise a target nucleic acid associated with the condition, contacting the sample with a reaction mixture containing a reactive compound and at least one set of chemically-reactive probes, at least one set of chemically-reactive probes comprising a plurality of a first probe, the first probe containing a chemical modification such as, but not limited to, a thiophosphate group, and a first nucleic acid region that is complementary to a first part of the target nucleic acid sequence, and a plurality of a second probe, the second probe containing a chemical modification such as, but not limited to, a primary amine group, and a second nucleic acid region complementary to a second, different part of the target nucleic acid sequence, wherein a distance between the first part and the second part of the target nucleic acid sequence is from 0 to 10 nucleotides, ligating the first probe and the second probe, in the presence of the target nucleic acid sequence, in a chemical ligation reaction to obtain a ligated product, and detecting the ligated product by immunochromatographic analysis.

In some embodiments, a method for determining the presence and/or level of an analyte in a sample comprises obtaining the sample containing or to be analyzed for the presence of a target nucleic acid, contacting the sample with a reaction mixture containing a reactive compound and at least one set of chemically-reactive probes. The at least one set of chemically-reactive probes comprising a plurality of a first probe, the first probe containing a chemical modification such as a thiophosphate group, and a first nucleic acid region, the first nucleic acid region being complementary to a first part of the target nucleic acid sequence, and a plurality of a second probe, the second probe containing a chemical modification such as a primary amine group, and a second nucleic acid region complementary to a second, different part of the target nucleic acid sequence, ligating the first probe and the second probe, in the presence of the target nucleic acid sequence, in a chemical ligation reaction to obtain a ligated product, and detecting the ligated product, for example by immunochromatographic analysis.

In some embodiments the ligated product is detected by immunochromatographic analysis. For example, ligated product can be capture and visualized using immunochromatographic strips coated with test line reagents and signal particles.

In some embodiments, a kit for diagnosing a condition in a subject is provided. Embodiments of the kit are based on the embodiments of the method of diagnosing a condition in a subject provided herein. In some embodiments, the kit comprises a reaction mixture containing a reactive compound and at least one set of chemically-reactive probes, at least one set of chemically-reactive probes comprising a plurality of a first probe, the first probe containing a chemical modification such as, but not limited to, a thiophosphate group, and a first nucleic acid region that is complementary to a first part of the target nucleic acid sequence, and a plurality of a second probe, the second probe containing a chemical modification such as, but not limited to, a primary amine group, and a second nucleic acid region complementary to a second, different part of the target nucleic acid sequence, wherein a distance between the first part and the second part of the target nucleic acid sequence is from 0 to 10 nucleotides, wherein the first probe and the second probe are configured to ligate in the presence of the target nucleic acid sequence to generate a ligated product, and immunochromatographic strips coated with test and control line reagents and signal particles configured for capturing and detecting the ligated product.

Additional Embodiments

In some embodiments, methods of determining the presence of a target nucleic acid in a sample are provided.

In some embodiments, the methods of determining the presence of a target nucleic acid in a sample comprise contacting the sample with a reaction mixture comprising at least one set of chemically-reactive probes, the at least one set of chemically-reactive probes comprising a plurality of a first probe, the first probe comprising a first nucleic acid region that is complementary to a first part of the target nucleic acid sequence and a first chemical group at a 3'end of the first nucleic acid sequence, and a plurality of a second probe, the second probe comprising a second nucleic acid region complementary to a second, different part of the target nucleic acid sequence and a second, different chemical group at a 5'end. The reaction mixture may also comprise an activator. The first and second parts of the target nucleic acid sequence may be in proximity to each, for example they may be separated by 10 nucleotides or less, wherein in the presence of the target nucleic acid in the sample the first probe and second probe anneal to the first and second parts of the target nucleic acid sequence and ligate together through a chemical ligation reaction between the first chemical group and the second chemical group to form a chemically ligated product, and detecting the chemically ligated product by capturing and visualizing the chemically ligated product on an immunochromatographic test strip, wherein detection of the chemically ligated product indicates the presence of the target nucleic acid in the sample.

In some embodiments of the method of determining the presence of a target nucleic acid in a sample, the chemical ligation reaction comprises activation of the first chemical group or the second chemical group by the activator and ligation of the activated first chemical group or the activated second chemical group to the second chemical group or the first chemical group, respectively.

In some embodiments of the method of determining the presence of a target nucleic acid in a sample, the activator is selected from the group consisting of 2-Fluoro-5-nitropyridine (FNP), 1-Fluoro-2,4-dinitrobenzene (FDNB), 1-Fluoro-2,4,6-Trinitrobenzene (FNTB) and succinimidyl iodoacetate (SIA).

In some embodiments of the method of determining the presence of a target nucleic acid in a sample, the the first part and the second part of the target nucleic acid sequence are substantially adjacent to each other in the target nucleic acid sequence.

In some embodiments of the method of determining the presence of a target nucleic acid in a sample, the sample is contacted with the reaction mixture at a temperature of 50 to 60° C.

In some embodiments of the method of determining the presence of a target nucleic acid in a sample, detecting the chemically ligated product by capturing and visualizing the chemically ligated product on an immunochromatographic test strip is performed at room temperature within 5 to 10 min of contacting the sample with the reaction mixture.

In some embodiments of the method of determining the presence of a target nucleic acid in a sample, the target nucleic acid sequence is not amplified prior to contacting the sample with the reaction mixture.

In some embodiments of the method of determining the presence of a target nucleic acid in a sample, the sample comprises a nasal swab, nasal aspirate, oropharyngeal swab, urine, sweat, tears, lymph, plasma, serum, saliva, semen, cerebrospinal fluid, synovial fluid, or blood.

In some embodiments of the method of determining the presence of a target nucleic acid in a sample, the method comprises contacting the sample with one or more additional sets of probes, each additional set of probes being configured to ligate in the presence of a different target nucleic acid sequence.

In some embodiments, the method of determining the presence of a target nucleic acid in a sample further comprises amplifying the chemically ligated product prior to detecting the chemically ligated product by capturing and visualizing the chemically ligated product on an immunochromatographic test strip.

In some embodiments of the method of determining the presence of a target nucleic acid in a sample, the first and second probes further comprise universal primer sequences, specific primer sequences, or both.

In some embodiments of the method of determining the presence of a target nucleic acid in a sample, the first and second probes further comprise universal or specific adapter sequences.

In some embodiments of the method of determining the presence of a target nucleic acid in a sample, the adapter sequences further comprise at least one barcode sequence.

In some embodiments of the method of determining the presence of a target nucleic acid in a sample, the first probe comprises an adapter sequence that is blocked at the 5' end with a blocking group.

In some embodiments of the method of determining the presence of a target nucleic acid in a sample, the blocking group is selected from a group consisting of Biotin, FITC, FAM, phosphate, and C3-spacer.

In some embodiments of the method of determining the presence of a target nucleic acid in a sample, the universal or specific primers sequences are located 5' to the first nucleic acid region of the first probe and 3' to the second nucleic acid region of the second probe.

In some embodiments of the method of determining the presence of a target nucleic acid in a sample, the amplification is selected from the group consisting of TARA-L-PCR, TARA-L-RPA, and TARA-L-LAMP.

In some embodiments of the method of determining the presence of a target nucleic acid in a sample, the chemically ligated product is amplified by an isothermal amplification process selected from the group consisting of loop-mediated isothermal amplification (LAMP) and recombinase-polymerase amplification (RPA).

In some embodiments of the method of determining the presence of a target nucleic acid in a sample, the first and second probes each comprise a reporter.

In some embodiments of the method of determining the presence of a target nucleic acid in a sample, the reporter is configured for detection, product capture, multiplexing, or a combination thereof.

In some embodiments of the method of determining the presence of a target nucleic acid in a sample, the reporter is selected from a group consisting of Biotin, FITC, FAM and digoxin.

In some embodiments of the method of determining the presence of a target nucleic acid in a sample, the first chemical group is a thiophosphate group.

In some embodiments of the method of determining the presence of a target nucleic acid in a sample, the second chemical group is a primary amine.

In some embodiments, a method of diagnosing a condition in a subject is provided.

In some embodiments, the method of diagnosing a condition in a subject comprises obtaining a sample from the subject that may comprise a target nucleic acid associated with the condition, contacting the sample with a reaction mixture comprising an activator selected from the group consisting of 2-Fluoro-5-nitropyridine (FNP), 1-Fluoro-2,4-dinitrobenzene (FDNB), 1-Fluoro-2,4,6-Trinitrobenzene (FNTB) and succinimidyl iodoacetate (SIA) and at least one set of probes, the at least one set of probes comprising a plurality of a first probe comprising a first nucleic acid region that is complementary to a first part of the target nucleic acid sequence and a first thiophosphate group at a 3' end, and a plurality of a second probe, the second probe comprising a second nucleic acid region complementary to a second, different part of the target nucleic acid sequence and a primary amine group at a 5' end, wherein a distance the first part and the second part of the target nucleic acid sequence are separated by 0 to 10 nucleotides, wherein in the presence of the target nucleic acid sequence the first and second products are ligated through a reaction between the thiophosphate group and the primary amine group to form a chemically ligated product, and detecting the chemically ligated product by immunochromatographic analysis, wherein detection of the chemically ligated product diagnoses the condition in the patient.

In some embodiments of the method of diagnosing a condition in a subject, the target nucleic acid is from a bacterium, fungus, virus, or parasite.

In some embodiments of the method of diagnosing a condition in a subject, the target nucleic acid is from a virus selected from the group consisting of dengue virus, influenza virus, chikungunya virus, the human immunodeficiency virus (HIV), the hepatitis C virus (HCV), human papillomavirus (HPV), Middle East respiratory syndrome (MERS) virus, arboviruses, respiratory syncytial virus (RSV; also known as human orthopneumovirus), coronavirus, and Ebola virus.

In some embodiments of the method of diagnosing a condition in a subject, he bacterium is selected from the group consisting of methicillin-resistant *Staphylococcus aureus* (MRSA).

In some embodiments of the method of diagnosing a condition in a subject, the parasite is selected from the group consisting of *Plasmodium falciparum* (malaria), *Candida auris* and Opisthorchiid liver flukes consisting of *Opisthorchis sinensis* (also known as *Clonorchis sinensis*), *Opisthorchi viverrini* and *Opisthorchis felineus*.

In some embodiments of the method of diagnosing a condition in a subject, the target nucleic acid is selected from the group consisting of RNA, DNA, and microRNA.

In some embodiments of the method of diagnosing a condition in a subject, the sample comprises a nasal swab, nasal aspirate, oropharyngeal swab, urine, sweat, tears, lymph, plasma, serum, saliva, semen, cerebrospinal fluid, synovial fluid, or blood.

In some embodiments, a kit for diagnosing a condition in a subject is provided.

In some embodiments, a kit comprises a reaction mixture comprising at least one set of chemically-reactive probes, the at least one set of chemically-reactive probes comprising a plurality of a first probe (G probe), the first probe comprising a first chemical group at a 3' end, and a first nucleic acid region that is complementary to a first part of a target nucleic acid sequence, and a plurality of a second probe (A probe), the second probe comprising a second chemical group at a 5'end, and a second nucleic acid region complementary to a second, different part of the target nucleic acid sequence. In some embodiments the reaction mixture comprises an activator. In some embodients a distance between the first part and the second part of the target nucleic acid sequence is from 0 to 10 nucleotides. The first probe and the second probe are configured to ligate by a chemical ligation reaction between the first chemical group and the second chemical group in the presence of the target nucleic acid sequence to generate a chemically ligated product. The kit can also contain immunochromatographic strips coated with test and control line reagents that bind the chemically ligated product.

In some embodiments, the condition is associated with a pathogen selected from a group consisting of bacterium, fungus, virus, and parasite.

In some embodiments, the virus is selected from the group consisting of dengue virus, influenza virus, chikungunya virus, the human immunodeficiency virus (HIV), the hepatitis C virus (HCV), human papillomavirus (HPV), Middle East respiratory syndrome (MERS) virus, arboviruses, respiratory syncytial virus (RSV; also known as human orthopneumovirus), coronavirus, and Ebola virus.

In some embodiments of the kit for diagnosing a condition in a subject, the target nucleic acid comprises RNA or DNA. In some embodiments the target nucleic acid comprises microRNA.

In some embodiments of the kit for diagnosing a condition in a subject, the liquid sample is selected from the group consisting of nasal swab, nasal aspirate, oropharyngeal swab, urine, sweat, tears, lymph, plasma, serum, saliva, semen, cerebrospinal fluid, synovial fluid, and blood.

In some embodiments, the bacterium is methicillin-resistant *Staphylococcus aureus* (MRSA).

In some embodiments, the parasite is *Plasmodium falciparum* (malaria), *Candida auris* and Opisthorchiid liver flukes consisting of *Opisthorchis sinensis* (also known as *Clonorchis sinensis*), *Opisthorchi viverrini* or *Opisthorchis felineus*.

In some embodiments of the kit for diagnosing a condition in a subject, the first chemical group is a thiophosphate group. In some embodiments of the kit for diagnosing a condition in a subject, the second chemical group is a primary amine.

In some embodiments, the activator is selected from the group consisting of 2-Fluoro-5-nitropyridine (FNP), 1-Fluoro-2,4-dinitrobenzene (FDNB), 1-Fluoro-2,4,6-Trinitrobenzene (FNTB) and succinimidyl iodoacetate (SIA).

In some embodiments, a set of chemically-reactive nucleic acid probes is provided. In some embodiments, a set of chemically-reactive nucleic acid probes comprises a plurality of a first probe (G probe), the first probe comprising a first chemical group at a 3' end, a first nucleic acid region that is complementary to a first part of a target nucleic acid sequence, and a first LAMP adapter, and a plurality of a second probe (A probe), the second probe comprising a second chemical group at a 5' end, a second nucleic acid region complementary to a second, different part of the target nucleic acid sequence, and a second LAMP adapter, wherein each of the first and second LAMP adapters comprise a first stem region, a first loop region, a second loop regions and a second stem region, wherein the first stem region and second stem region are complementary to, and configured to bind to each other.

In some embodiments, each of the first and second probes further comprise a sequence between the first nucleic acid region and second nucleic acid region, respectively, wherein the sequence in the first probe is complementary to, and configured to bind to, a portion of the first nucleic acid region and the sequence in the second probe is complementary to, and configured to bind to, a portion of the second nucleic acid region.

In some embodiments each of the first and second LAMP adapters further comprising a barcode sequence between the first loop region and the second loop region, wherein the barcode sequence in the first LAMP adapter is complementary to, and configured to bind to, the barcode sequence in the second LAMP adapter.

EXAMPLES

The following examples are non-limiting and other variants within the scope of the art were also contemplated.

Example 1—TARA-L Ligation Chemistry Assessment

Example 1.1—TARA-L Ligation Chemistry Assessment Using microRNA Probes

TARA-L probes were designed to detect microRNA and contained universal PCR primer sequences for downstream amplification. Table 1 shows the sequences of the probes, primers, and templates designed and synthesized for TARA-L-based microRNA diagnostics. Probes were also modified with different chemical groups and were tested in different combinations for their ability to ligate in a template-assisted manner under TARA-L reaction conditions. Table 2 shows 10 different chemical-group combinations tested by TARA-L.

TABLE 1

Sequences of the probes, primers, and templates designed and synthesized for TARA-L-based microRNA diagnostics.

| Oligo | Sequence* |
|---|---|
| Mir21-G Probe | 5'-{BioBB}GGG TTC CCT AAG GGT TGT CAA CAT CAG{*}-3' (SEQ ID NO: 1) |
| Mir21-A Probe | 5'-{*}TC TGA TAA GCT AAG ATT GGA TCT TGC TGG CAC-FAM-3' (SEQ ID NO: 2) |
| Mir21 Template | 5'-TAG CTT ATC AGA CTG ATG TTG AAT TAA AA-3' (SEQ ID NO: 3) |
| Mir495-G Probe | 5'-{BioBB}GGG TTC CCT AAG GGT TGC GAA AAT AAC A{*}-3' (SEQ ID NO: 4) |
| Mir495-A Probe | 5'-{*}TGG GCA ACT TCA GAT TGG ATC TTG CTG GCA C-FAM-3' (SEQ ID NO: 5) |
| Mir495 Template | 5'-GAA GTT GCC CAT GTT ATT TTC GAT TAA AA-3' (SEQ ID NO: 6) |
| UF | 5'-GGG TTC CCT AAG GGT TG-3' (SEQ ID NO: 7) |
| UR | 5'-GTG CCA GCA AGA TCC AAT CT-3' (SEQ ID NO: 8) |
| Biotin-UF | 5'-/5 Biotin TEG/GGG TTC CCT AAG GGT TG-3' (SEQ ID NO: 9) |
| FITC-UR | 5'-/56-FAM/GTG CCA GCA AGA TCC AAT CT-3' (SEQ ID NO: 10) |

*Bold text shows UF/UR primer binding sites on the G and A probes, respectively; {*} implies chemical modification with or without activation as shown in Table 2.

TABLE 2

Chemical modifications of G and A probes for TARA ligation.

| Chemistry Pair | 3' G probe modification | 5' A probe modification |
|---|---|---|
| 1 | 2-Fluoro-5-nitropyridine (FNP) | NH₂ |
| 2 | FNP | Thiophosphate (PS) |
| 3 | PS | FNP |
| 4 | Hydroxyl (OH) | FNP |
| 5 | PS | NH₂ |
| 6 | PS | PS |
| 7 | OH | NH₂ |
| 8 | OH | PS |
| 9 | PS | Succinimidyl iodoacetate (SIA) |
| 10 | OH | SIA |

Figure 5:
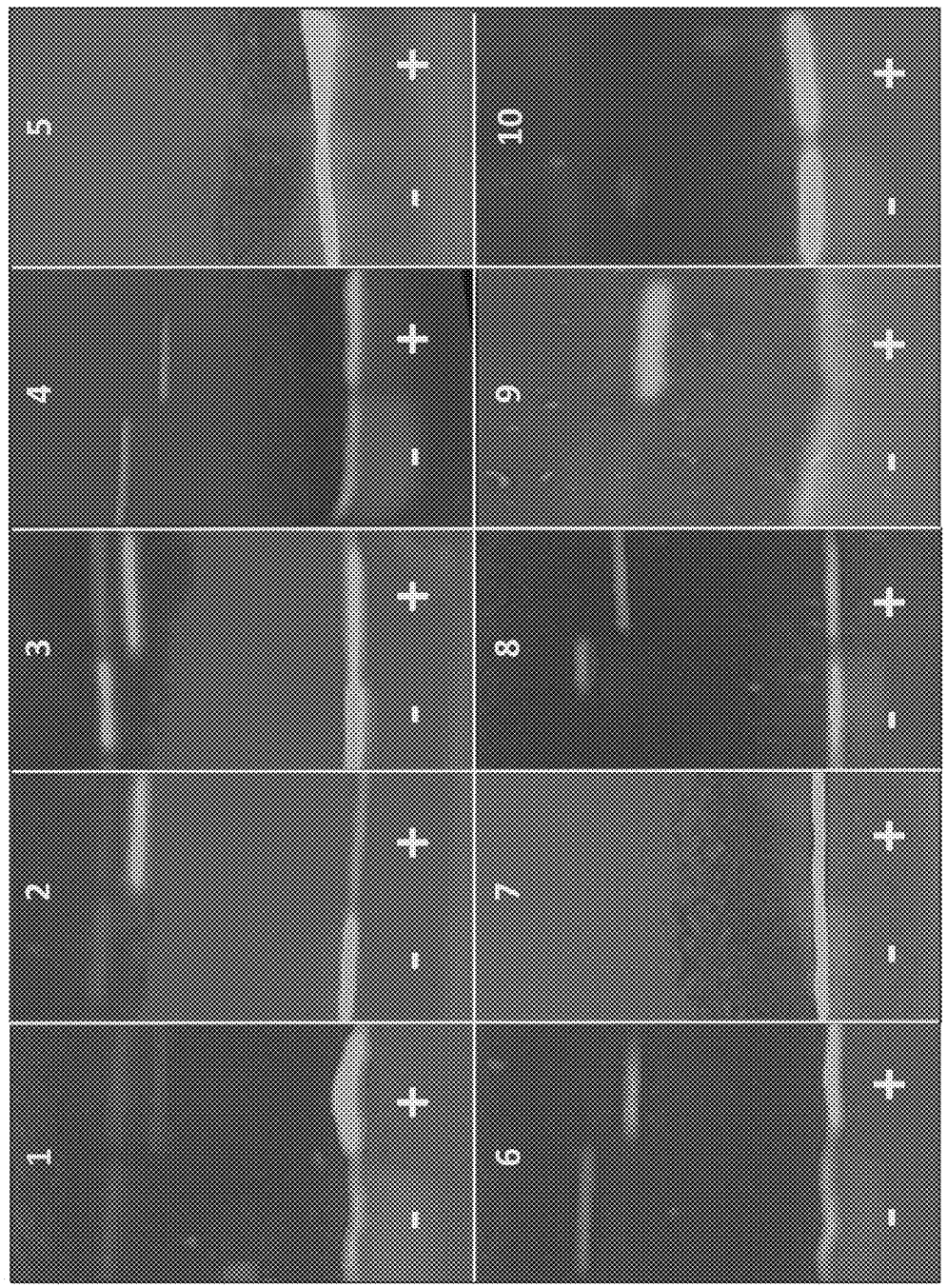
FIG. 5 shows SDS-PAGE results for TARA-L ligation tests using different chemistry pairs. Chemistry combinations 1-4, 6, and 8-9 are able to ligate probes in the presence of a template, while chemistry combinations 5, 7 and 10 do not ligate. Ligation on the SDS-PAGE can be seen as the appearance of an extra band, or a shift in the band position. Chemistry pairs were as follows (G and A probes, respectively): 1—FNP NH$_2$; 2—FNP PS; 3—PS FNP; 4—OH FNP; 5—PS NH$_2$; 6—PS PS; 7—OH NH$_2$; 8—OH PS; 9—PS SIA; 10—OH SIA.

TARA reactions were carried out using 0.4 µM probes and template for direct viewing by 16% SDS-PAGE (sodium dodecyl sulfate-polyacrilymide gel electrophoresis). SDS-PAGE analyses were performed because the denaturing properties of the gel would show a band shift only for ligation events and not for general annealing. The G probes were 5'-blocked with FAM, which doubled as a reporter molecule for direct viewing of bands in the SDS-PAGE gel. Following reaction completion, a 'STOP' solution containing 95% formamide, 5 mM EDTA (ethylenediaminetetraacetic acid) and 0.25 mg/ml bromophenol blue was added 1:1 (v:v) to each reaction to halt the TARA reaction, as well as double as a loading dye for SDS-PAGE analysis. Samples were heated to 95° C. for 5 minutes before loading 30 µl of sample per lane in a 16% SDS-PAGE gel. Results showed that chemistry combinations 1-4, 6, and 8-9 are able to ligate TARA probes in the presence of a template, with no observable ligation present in samples containing no template, while chemistry combinations 5, 7 and 10 do not ligate (FIG. 5). Due to the reactive nature of the chemical modifications, it is possible for ligation to occur between modifications among the same probe (e.g.: G-G probe ligation) at high concentrations and in the absence of an inhibitor compound such as a reducing agent. SDS-PAGE will show non-specific ligation; therefore; SDS-PAGE ligation results can be seen as the appearance of an extra band or a shift in the band position. Non-specific G-G probe ligations, for example, would not appear on lateral flow strips, when designed to detect dual-labelled ligation products, such as Biotin-FAM dual-labels.

Reactions between PS and PS (chemistry combination 6) are known to produce disulfide bonds (S—S) that can be broken using reducing agents. TCEP and DTT were used to test if reaction products can be disrupted using reducing agents. Chemistry pairs showing positive ligation (1-4, 6, 8-9) were tested for ligation in the presence of reducing agent. SDS-PAGE results for TARA reactions with and without the addition reducing agent suggest that DTT (FIG. 6) and TCEP can disrupt chemistry pairs 2-4, 6 and 8; only chemistry pairs 1 (—FNP $NH_2$—) and 9 (—SH SIA-) were unaffected by the presence of reducing agents; SIA chemistry (chemistry pair 9) was omitted from FIG. 6 due to the fact the SIA chemistry is run in buffer that already contains DTT or TCEP.

Figure 7A:
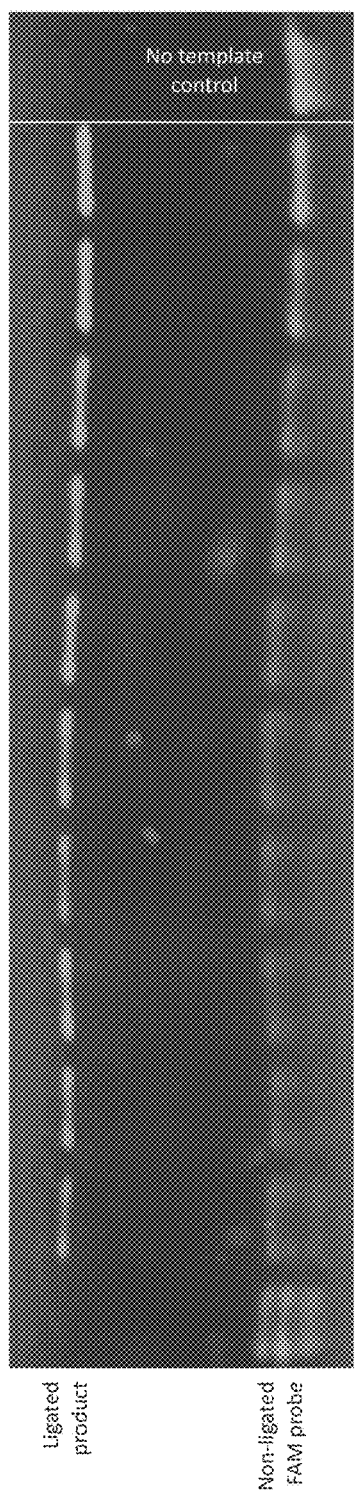
FIGS. 7A-7B show TARA-L time tests for chemistry pairs using SIA chemistry.
Figure 7B:
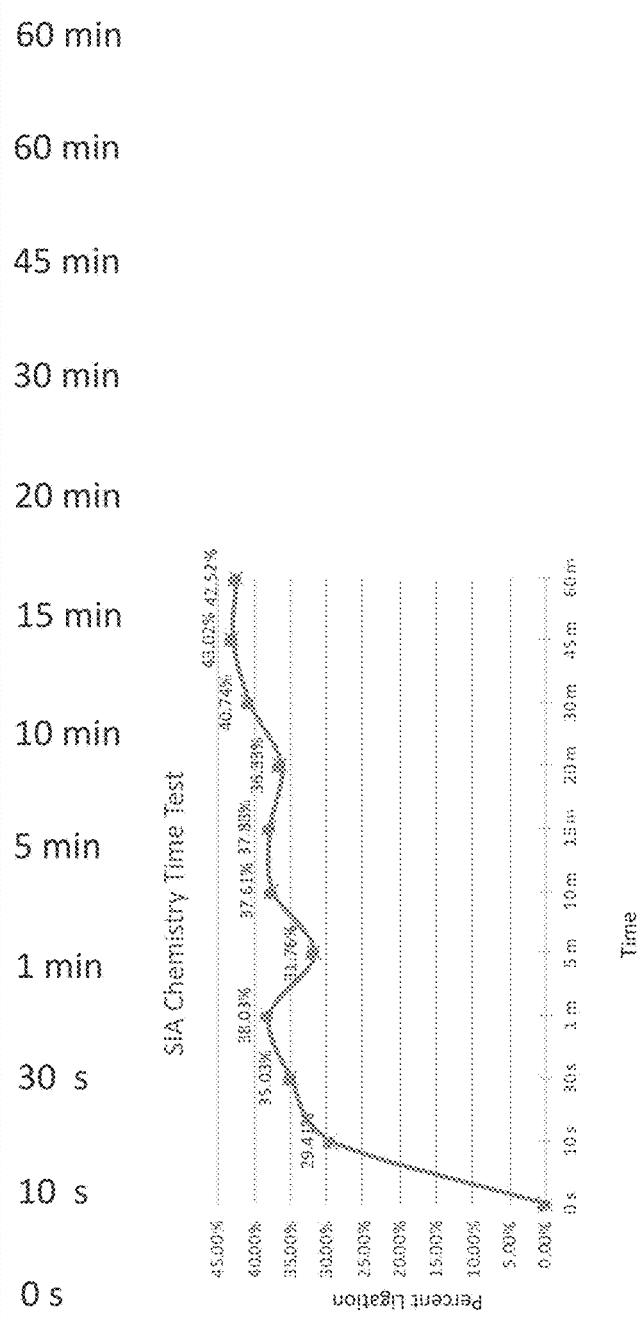

A time test was also conducted on the various chemistry pairs. TARA-ligation tests were run as 50-µl reactions containing 0.4 µM probes and template. TARA-ligation reactions took place at 55° C. and were 'stopped' at various time points by mixing samples 1:1 v:v with 'STOP' solution (95% formamide, 5 mM EDTA and 0.25 mg/ml bromophenol blue) and heating at 95° C. for 5 min. Reactions were loaded onto a 16% SDS-PAGE gel at 30 µl per well. Results indicate that ligation is extremely rapid, with positive results appearing as fast as 10 s. A no-template control was included, reacted for 60 min, and showed no observable ligation, validating the positive results. Results were similar for other chemistry pairs, with majority of the ligation taking place in less than 5 minutes. FIG. 7A-7B shows representative time test data from SIA chemistry.

TARA chemistry ligation reactions were also tested using downstream amplification with PCR to assess the possibility of amplification inhibition resulting from the bond formed during ligation. Each of the 10 different chemistry pairs were subjected to 50-µl TARA-ligation reactions, containing 10 nM probes, with or without 10 nM template (+ or –, respectively), at 55° C. for 15 min. All chemistries except SIA were run in water, while SIA was run in SIA buffer (70 mM Tris pH 7.0; 10 mM $MgCl_2$; 1 mM DTT). Completed TARA reactions were first tested on lateral flow strips (5 µl TARA sample per strip) to ensure proper initial TARA ligation. Reactions were then diluted 10-fold and retested by lateral flow strip to confirm that the concentration of ligated product was below the strip sensitivity (lateral flow strip negative). Diluted completed TARA reactions were then amplified by PCR. PCR was conducted in 20-µl reactions containing 1× Luna® Universal Probe qPCR Master Mix, 0.4 µM biotin-labelled F and FAM-labelled R primers (Table 1), and 5 µl diluted completed TARA reaction. PCR conditions were as follows: initial denaturing at 95° C. for 1 min followed by 25 cycles of denaturing at 95° C. for 15 s, annealing at 60° C. for 30 s and extension at 72° C. for 30 s. Completed PCR reactions were tested on lateral flow strips (5 µl TARA sample per strip).

TARA-L-PCR reactions corroborated SDS-PAGE gel results, demonstrating that chemistry combinations 1-4, 6, and 8-9 are able to ligate and amplify, as seen by the reappearance of the positive test line, while chemistry combinations 5, 7 and 10 do not (FIG. 8). Non-specific ligation in the absence of template was not observed by direct application of TARA-L samples to lateral flow strips due to the inherent sensitivity of the LFA; however, non-specific ligation in the absence of template was observed following downstream amplification by PCR.

Combined data suggest that while chemistry combinations 1-4, 6, and 8-9 work for TARA, there are potential issues that can arise for some chemistry pairs. There exists the potential for homo-ligated-dimers of probes containing the PS chemistry (G-G or A-A). There also exists the potential for PS-containing probes to non-specifically ligate to either 5'- or 3'-OH groups present in unmodified synthetic oligonucleotides. These issues can be resolved by the addition of a reducing agent, such as TCEP or DTT; however, this will also prevent proper template-assisted ligation.

Example 1.2—TARA-L Ligation Chemistry Inhibition Tests Using microRNA Probes

Figure 9:
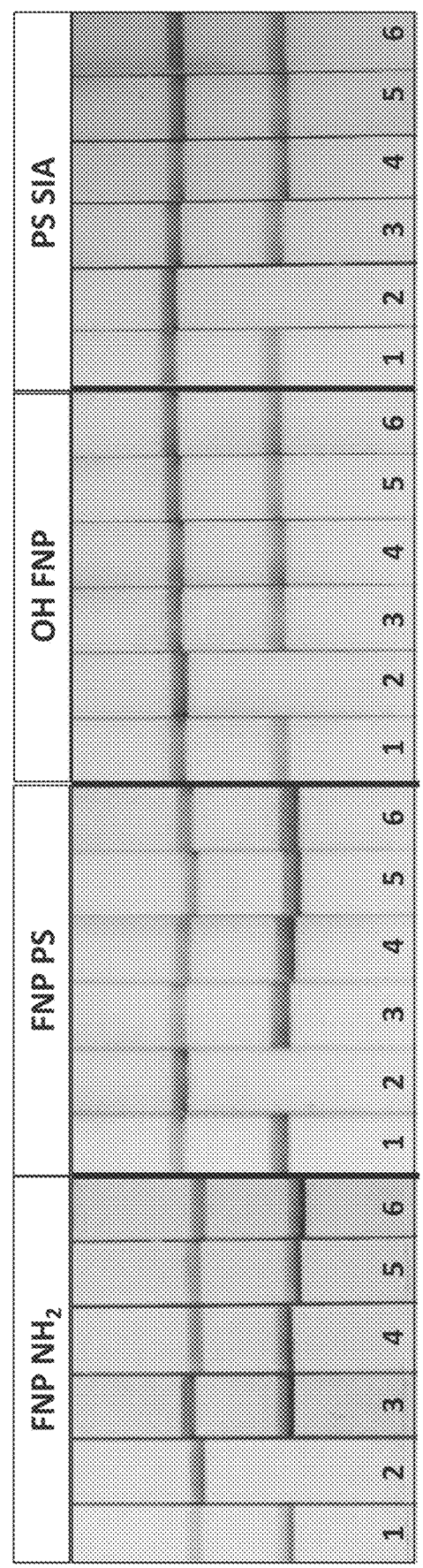
FIG. 9 shows four representative chemistry pairs tested for inhibition in the presence of biological material. Chemistry pairs were tested in a 50 μl TARA-L reactions containing high concentrations of biological sample material, along with positive and negative controls containing no biological material. The presence of biological sample material in the reaction did not affect the results for each chemistry pair relative to the positive control. 1) positive control (no biological material); 2) negative control (no template); 3) 30% saliva; 4) 30% blood plasma; 5) 30% urine; 6) 4% bovine serum albumin (BSA).

TARA-ligation reactions were also tested for functionality in the presence of biological material, using spiked biological samples. All ligating chemistry pairs were tested for ligation in the presence of saliva, blood plasma, urine and BSA (Bovine Serum Albumin). Chemistry pairs 1 and 9 (—FNP $NH_2$— and —PS SIA-) performed equally when TARA reactions were performed in 50-µl reactions containing as much as 15 µl saliva, blood plasma or urine (30% total), or 15 µl 10% BSA (4% total). Reactions were assessed by SDS-PAGE and lateral flow strips and showed no, if not minimal, inhibition of the TARA-ligation reaction in the presence of saliva, blood plasma and BSA. Reactions containing 30% urine showed a marked decrease in band intensity relative to the other biological samples under SDS-PAGE; however, TARA ligation still occurred and with decreased concentrations of urine, more TARA ligation was observed. FIG. 9 shows lateral flow strip results for four representative chemistry pairs. TARA ligation was also assessed under harsh lysis buffer conditions. Proper TARA ligation occurred even when reactions were run using CLBuffer-1 and CLBuffer-2. Together, these results demonstrate the robustness of the TARA-ligation reactions and their applicability to testing with biological samples.

Example 2—HIV-1 Diagnostics by Detection and Quantitation of Viral Nucleic Acids Using TARA-L TARA-L was used to detect and quantitate viral nucleic acids of HIV-1 for HIV diagnostics. Table 3 provides the sequences of the probes, primers, and templates designed and synthesized for the purpose of TARA-L-based HIV-1 diagnostics.

TABLE 3

Sequences of the probes, primers, and templates designed and synthesized for TARA-L-based HIV-1 diagnostics.

| Oligo | Sequences* |
|---|---|
| LHIV-G Probe | 5'-{BioBB}GGG TTC CCT AAG GGT TGG TTT AGC ATG GTG TTT AAA TCT TGT GGG G{.Sphos}-3' (SEQ ID NO: 11) |
| LHIV-A Probe | 5'-Amino-dT-GGC TCC TTC TGA TAA TGC TGA AAA CAT AGA TTG GAT CTT GCT GGC AC-C3-FAM-3' (SEQ ID NO: 12) |
| LHIV-1 Template | 5'-ATG TTT TCA GCA TTA TCA GAA GGA GCC ACC CCA CAA GAT TTA AAC ACC ATG CTA AAC-3' (SEQ ID NO: 13) |
| LHIV-1D Template | 5'-ATG TTT TCA GCA TTA TCA GAA GGA GCC ACC CA CAA GAT TTA AAC ACC ATG CTA AAC-3' (SEQ ID NO: 14) |
| UF | 5'-GGG TTC CCT AAG GGT TG-3' (SEQ ID NO: 15) |
| UR | 5'-GT GCC AGC AAG ATC AAT CT-3' (SEQ ID NO: 16) |
| Biotin-UF | 5'-/5 Biotin TEG/GGG TTC CCT AAG GGT TG-3' (SEQ ID NO: 17) |
| FITC-UR | 5'-/56-FAM/GT GCC AGC AAG ATC CAA TCT-3' (SEQ ID NO: 18) |

*Bold text shows UF/UR primer binding sites on the G and A probes, respectively.

Example 2.1—Reaction Conditions of TARA-L

To examine the reaction efficiency of TARA-L in different buffers, ligation reactions were carried out, using identical concentrations of templates and probes (Template (LHIV-1) 0.04 µM, FDNB-activated probe G or FNP-activated probe G (LHIV-G) 0.4 µM, and probe A (LHIV-A) 0.2 µM), in three different buffers at the same pH (CLBuffer-1, pH 8.0; CLBuffer-2, pH 8.0; and CLBuffer-2, pH 8.0 mixed with nasal swab).

Figure 10A:
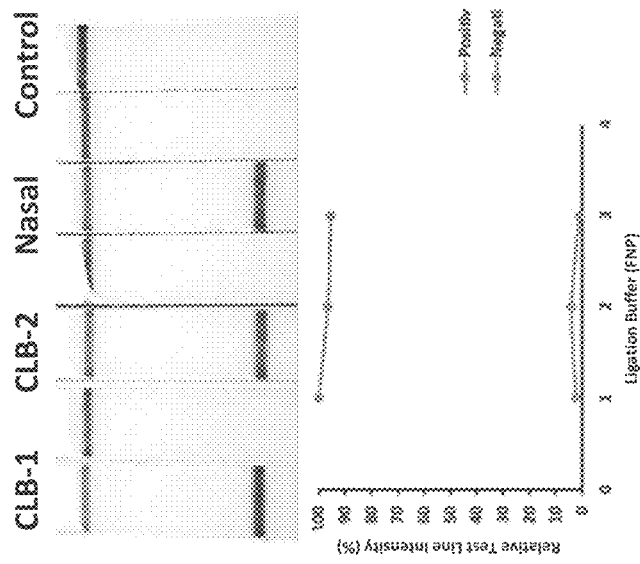
FIGS. 10A-10B show strip detection of TARA-L products where CLBuffer-1, CLBuffer-2, and CLBuffer-2 mixed with a nasal swab were used as ligation reaction buffers. Chase buffer only, without TARA-L samples, was also tested as a blank control (control). In the line graphs, upper line represents "Positive" and lower line represents "Negative."
Figure 10B:
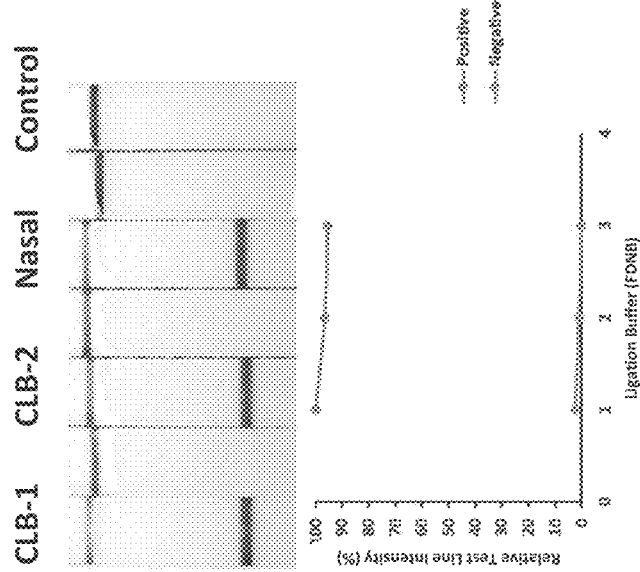

TARA-L reactions were carried out at 95° C. for 2 min and 55° C. for 30 min. The TARA-L products were directly applied to lateral flow strips for detection (5 µl per strip). FIGS. 10A-10B show that the TARA-L reactions took place in both buffers for both FDNB- (FIG. 10A) and FNP-activated (FIG. 10B) probe G. CLBuffer-2, mixed with nasal swab, did not significantly influence the TARA-L reaction according to the test line intensities of positive and negative controls. CLBuffer-2 was selected to be the buffer of choice for further pH optimization considering the simpler composition than that of CLBuffer-1.

Figure 11B:
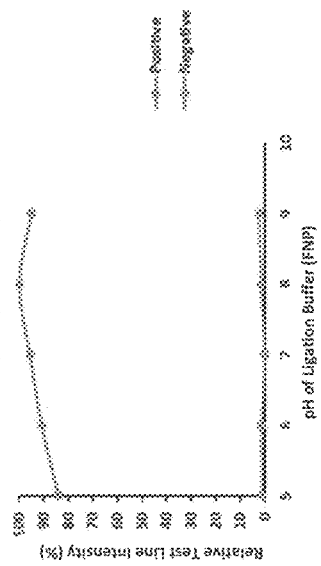
FIGS. 11A-11B show strip detection of TARA-L products where CLBuffer-2 at five different pH values (5.0, 6.0, 7.0, 8.0, and 9.0) was used as ligation reaction buffer. Chase buffer only, without TARA-L samples, was also tested as a blank control (control). In the line graphs, upper line represents "Positive" and lower line represents "Negative."
Figure 11A:
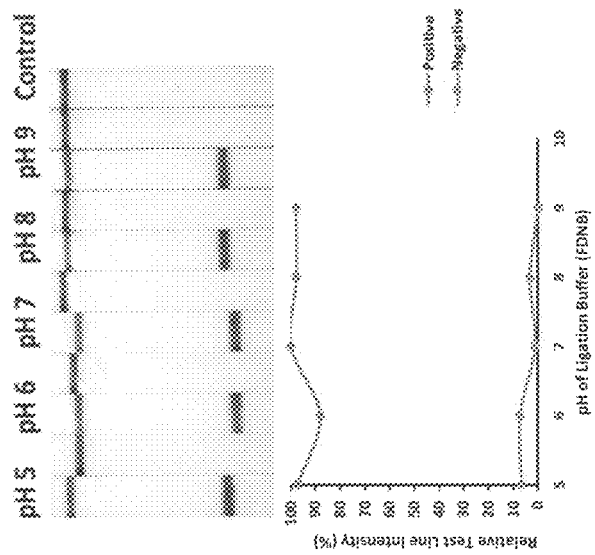

CLBuffer-2 was pH-adjusted using HCl and NaOH to produce buffers of five different pH's (pH 5.0, 6.0, 7.0, 8.0, and 9.0). These buffers were used as the reaction buffer for TARA-L reactions. Templates and probes were mixed (0.04 µM LHIV-1, 0.4 µM FDNB- or FNP-activated LHIV-G, and 0.2 µM LHIV-A) and reacted at 55° C. for 30 min. The TARA-L products were directly applied to lateral flow strips (5 µl per strip). FIGS. 11A-11B show that TARA-L reactions employing either FDNB-activated G probes (FIG. 11A) or FNP-activated G probes (FIG. 11B) proceed in all CLBuffer-2 at the five different pH's. The test line intensity showed that, for FDNB-LHIV-G, pH 7.0 buffer had the highest intensity for the positive control and the lowest intensity for the negative control (FIG. 11A). For FNP-LHIV-G, the TARA-L reaction had the best performance at pH 8.0 (FIG. 11B).

Figure 12A:
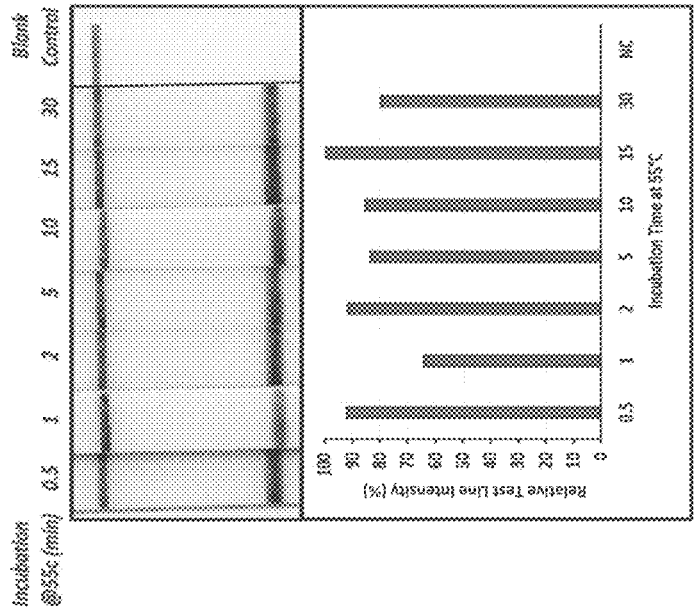
FIGS. 12A-12B show strip detection of TARA-L products after different reaction times at 55° C. (0.5, 1, 2, 5, 10, 15, and 30 min).
Figure 12B:
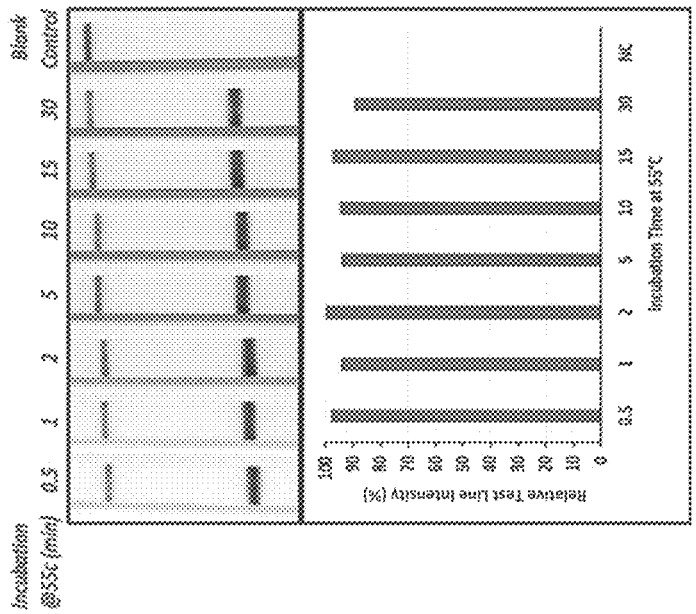

TARA-L reactions were carried out for different durations and then tested on lateral flow strips. TARA-L reactions (total volume 50 µl), including template LHIV-1 (0.04 µM), FNP-activated LHIV-G (0.4 µM), and LHIV-A (0.2 µM) in CLBuffer-2 (1×, pH 8.0), were incubated at 95° C. for 2 min, then 55° C. for 0.5, 1, 2, 5, 10, 15, and 30 min (FIG. 12A), or directly incubated at 55° C. for different durations (without the initial heating at 95° C.) (FIG. 12B). Water was used instead of template as a blank control. After the TARA-L reactions, 5 µl of each TARA-L product was applied to lateral flow test strips for detection. TARA-L reactions were found to happen very fast; the test line of 0.5 min or 1 min reactions had almost the same intensities as those of longer reaction times of 10, 15, or 30 min (FIG. 12A). Without the initial step of denaturation at 95° C., the TARA-L reactions at 55° C. took place at a comparably fast speed, with the test lines of 0.5 min reaction product having almost the same intensities as those of longer reaction times of 10, 15, or 30 min (FIG. 12B).

Figures 13A, 13B:
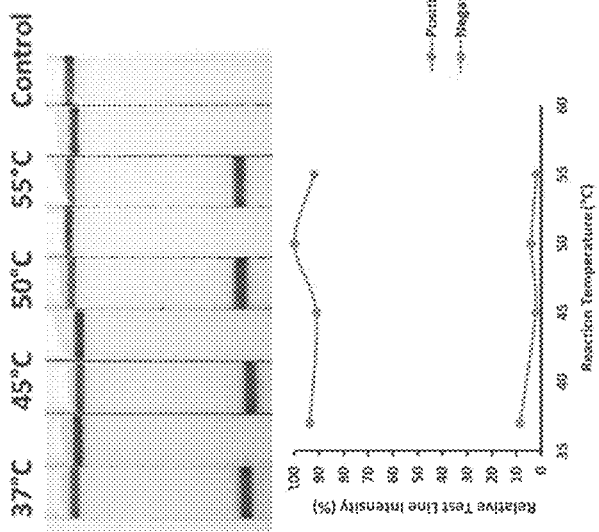

TARA-L reactions, with the same amount of template and probes (LHIV-1 0.04 µM, FDNB-activated LHIV-G 0.4 µM, and LHIV-A 0.2 µM), were incubated at different temperatures (37° C., 45° C., 50° C., and 55° C.) for 30 min after a 2-min preheating at 95° C. The resulting TARA-L products were directly detected on lateral flow test strips. FIGS. 13A-13B show that the reaction temperature did not have a significant effect on ligation efficiency. Reactions at higher temperatures (50° C. and 55° C.) showed a slightly higher intensity difference between test lines and control lines.

Example 2.2—TARA-L and TARA-rt-PCR Tests

Figure 14B:
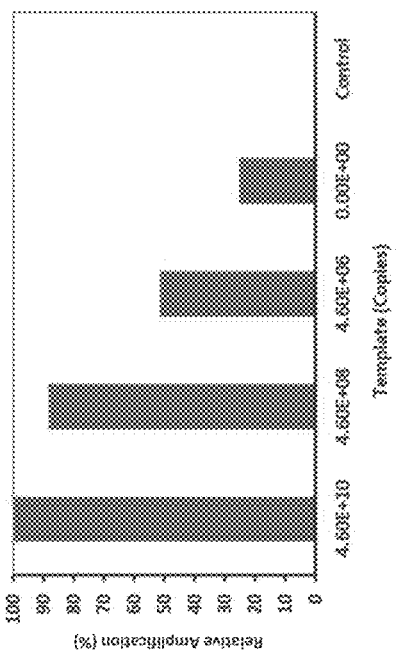
FIGS. 14A-14B show TARA-L assays of different concentrations of LHIV-1 templates, detected by strips (TARA-L) or rt-PCR (TARA-rt-PCR).
Figure 14A:
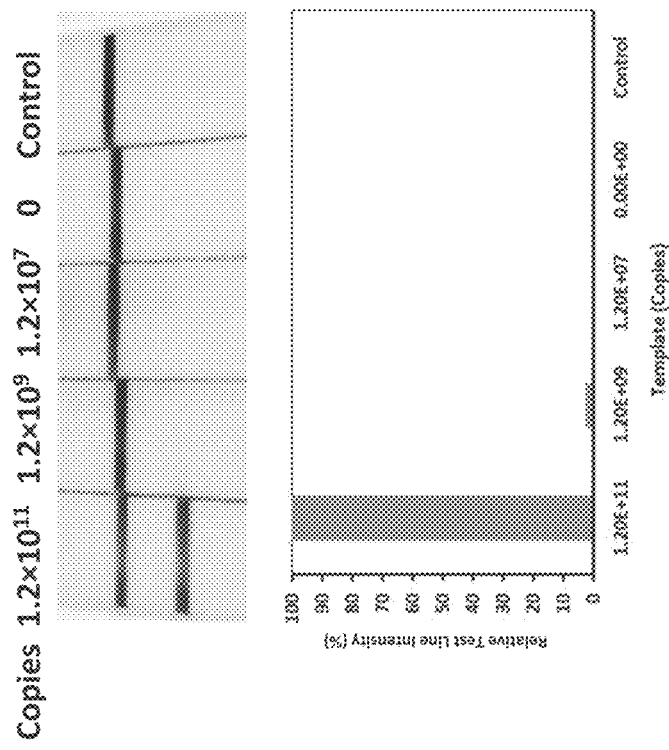

TARA-L reaction products were directly tested by lateral flow strips without subsequent amplification or amplified by real-time PCR (TARA-rt-PCR). The sensitivity of strip detection of TARA-L without PCR was determined using a series of ligation reactions containing the same amount of LHIV-G (FDNB-activated, 0.4 µM) and LHIV-A (0.2 µM), but different amounts of template LHIV-1 ($4 \times 10^{-2}$ µM (40 nM), $4 \times 10^{-4}$ µM (400 pM) and $4 \times 10^{-6}$ µM (4 pM)). The negative control contained FDNB-activated LHIV-G (0.4 µM) and probe LHIV-A (0.2 µM), with no template. For strip tests, 5 µl of TARA-L products were applied directly, which corresponded to $1.2 \times 10^{11}$, $1.2 \times 10^{9}$, and $1.2 \times 10^{7}$ copies of LHIV-1 template. Only the sample containing the highest concentration of template showed a strong test line, which corresponded to $1.2 \times 10^{11}$ copies (FIG. 14A). ImageJ analysis was performed on the strip images and the test-line intensities were calculated and normalized so the most and least intense test lines have 100% and 0% percent intensities, respectively. The test line of the second highest template level ($1.2 \times 10^{9}$ copies) was only discernible when analyzed by ImageJ (FIG. 14A). Therefore, the detection limit was taken to be between $1.2 \times 10^{11}$ and $1.2 \times 10^{9}$ copies. This sensitivity reflects the lateral flow strip's ability to provide a detectible result when TARA-L product is present in the sample; absence of a test line does not mean no ligated product, it just means that the strip was unable to detect the level present in the sample. Thus, amplification reactions can be used to subsequent to TARA-L to produce enough product that can be view by lateral flow strip.

Real-time PCR amplification was performed to better reflect the TARA-L ligation reaction results, as the lateral flow strip sensitivity was unable to detect the second highest template level by naked eye. For TARA-rt-PCR, TARA-L products were desalted using G-25 spin columns before rt-PCR and 2 µl of TARA-L reaction were used, which corresponded to $4.8\times10^{10}$, $4.8\times10^{8}$, and $4.8\times10^{6}$ copies of LHIV-1 template. Threshold cycle (CO values were normalized, with the level of the highest concentration assumed to be 100% and the water blank control being considered 0%, to account for background due to non-specific probe ligation in the absence of template in the negative control. FIG. 14B shows that $C_t$ values, and their corresponding normalization values, correlated positively to the amount of template added in each reaction; more template in the reaction produced a lower $C_t$ value, and thus a higher amplification level was obtained. The lowest concentration of template used for TARA-L ($4.8\times10^{6}$ copies) had lower $C_t$ value than that of the negative control (non-specific background amplification).

To determine the detection limit of the lateral flow strips, TARA-L reactions containing LHIV-1 (4 µM), FDNB-activated LHIV-G (4 µM) and LHIV-A (2 µM) were performed and then diluted with water 10-, 100-, 1000-, and 10,000-fold, before 5 µl of which were tested using the lateral flow strips. As shown in FIGS. 15A-15B, the detection limit for the lateral flow strips, without subsequent amplification of TARA-L products, was approximately $1.2\times10^{10}$ copies, the test line of which was discernible by the naked eye.

Example 2.3—TARA-Rt-PCR Versus TARA-L-PCR and FNP-Activation Versus FDNB-Activation TARA-L reactions, employing FNP or FDNB, were compared in terms of both sensitivity and specificity. FNP- or FDNB-activated LHIV-G was quantified using 260 nm absorption, following the activation reaction and desalting with a G25 column. A series of TARA-L reactions were carried out (100 µl in total), containing low concentrations of template LHIV-1 ($4\times10^{-6}$ µM (4 pM), $4\times10^{-7}$ µM (400 fM), $4\times10^{-8}$ µM (40 fM), $4\times10^{-9}$ µM (4 fM), $4\times10^{-10}$ µM (400 aM), and ddH$_2$O as negative control), LHIV-G activated with either FDNB or FNP (0.02 µM), LHIV-A (0.02 µM), and CLBuffer-2 (1x, pH 8.0). All reactions were incubated at 95° C. for 2 min and 55° C. for 30 min.

After TARA-L reactions, 2 µl of each TARA-L product was mixed with rt-PCR master mix, containing 250 nM unlabeled UF and UR, and amplified with real-time fluorescence monitoring according to the following conditions: 95° C. for 1 min, and 45 cycles of 95° C. for 15 s, 60° C. for 30 s, and 72° C. for 30 s. Furthermore, 2 µl of each TARA-L product was also mixed with PCR master mix, containing 250 nM FITC-UF and biotin-UR, and amplified according to the following conditions: 95° C. for 1 min, and 22 cycles of 95° C. for 15 s, 60° C. for 30 s, and 72° C. for 30 s. FIGS. 15A-15(B) show that amplification levels monitored using rt-PCR correlated positively with concentrations of template LHIV-1 in both TARA-L reactions employing either FDNB (FIG. 15A, FDNB-qPCR) or FNP (FIG. 15(B), FNP-qPCR). After PCR amplification for 22 cycles, 1 µl of amplified TARA-L samples was analyzed directly by lateral flow strips. The test-line intensities also correlated positively to the original template concentrations, especially for the FNP-activated G probe (FIG. 15(B), FNP-Strip). The FNP-activated G probe test-line intensity for the lowest template concentration was significantly higher than that of both negative controls; one is a TARA-L negative control for ligation containing probes, primers, and no template, while the other is a PCR negative control, containing primers and no TARA-L sample. In contrast, for FDNB-activated G probe (FIG. 15A, FDNB-Strip), the test-line intensity of the TARA-L negative control, containing probes and primers only, was higher than that of TARA-L sample containing the lowest amount of template.

Example 3—TARA-L-LAMP Theory, Design and Data

Example 3.1—TARA-L-LAMP Probe Design

TARA probes were designed specifically to be used directly with downstream LAMP assays through the creation of synthetic dumbbell-loop structures, which are attached to the 5'- and 3'-ends of the G and A probe target sequences, respectively. These 'universal' LAMP adapters were designed from purely randomized synthetic sequences and chosen to include all portions of a LAMP dumbbell, while meeting the suggested parameters for proper LAMP assay performance (FIG. 17A). TARA-L-LAMP probe target sequences would be chosen to specifically anneal to a desired nucleic acid target, such as, but not limited to, specific viral DNA/RNA, specific bacterial DNA/RNA, specific fungal DNA/RNA and/or specific parasite DNA/RNA. Sequences for the TARA-L-LAMP adapters are shown in Table 4.

TABLE 4

TARA-L-LAMP 'universal' probe adapter and primer sequences.

| | | OligoSequence (5'→3') |
|---|---|---|
| 'Universal' Probe Adapter | G | {B}AATGCGGATGCGGATGCCGACTCGTCAT GATGACTGGTGCCAACCCTTAGGGAACCCTC GGCATCCGCATCCGCATT* (SEQ ID NO: 19) |
| | A | *CGCATCCGGGTCCTCAGCGTGTGCCAGCAA GATCCAATCTATTGCGTATGTCGGTGCCTGA CGCTGAGGACCCGGATGCG (SEQ ID NO: 20) |
| 'Universal' LAMP Primers | FIP | AATGCGGATGCGGATGCCGACTCGTCATGAT GACTGGTGC (SEQ ID NO: 21) |
| | BIP | CGCATCCGGGTCCTCAGCGTCAGGCACCGAC ATACGCAAT (SEQ ID NO: 22) |
| | LF | BIOTIN-GGGTTCCCTAAGGGTTG (SEQ ID NO: 23) |
| | LB | FAM-GTGCCAGCAAGATCCAATCT (SEQ ID NO: 24) |
| TARA-LAMP ligated product PCR primers | F | CAACCCTTAGGGAACCC (SEQ ID NO: 25) |
| | R | AGATTGGATCTTGCTGGCAC (SEQ ID NO: 26) |

*TARA-L-LAMP 'universal' probe adapters attach to the 5' and 3' ends of the G and A probe target sequences, respectively.
{B}-5'-blocking group such as, but not limited to, Biotin, FITC, FAM, phosphate or C3-spacer.
Note:
Loop primers LF/LB can be labelled with different tags depending on the application and/or 5'-blocking group used for the G probe.

Non-specific ligation of TARA probes can occur in the absence of a target molecule, especially at high concentrations, due to the reactive ends of the probes coming into proximity randomly within solution. This becomes increasingly more important when TARA ligation is followed by a subsequent amplification step, as seen in FIG. 8 and FIG. 16. Hairpin stem-loops were designed into one or both probe target sequences (on G and/or A probe) to prevent non-specific ligation when the template/target is not present (FIG. 17B). Nucleotides were added between the LAMP adapters and the probe target sequences such that they have complementary base pairing with the distal end of the target sequence, thus promoting secondary hairpin stem-loop formation.

In the presence of a target molecule with complementary sequence to the probes, the stem-loops preferentially bind/anneal, open and allow the reactive ends to come into proximity to allow ligation (FIG. 18A). The 'universal' LAMP adapters produce a product, upon proper ligation, that can be directly amplified using LAMP (FIG. 18B). This product essentially represents the first dumbbell loop structure created during a LAMP reaction, therefore the outer primers (F3/B3) required by a standard LAMP reaction can be omitted, as they are only required to assist in creating the initial dumbbell loop structure. The subsequent LAMP reaction of the TARA-L-LAMP assay requires only four primers, the 'universal' inner (FIP/BIP) and loop (LF/LB) primers (Table 4, FIG. 18B). Loop primers are tagged with biotin and FAM/FITC, allowing results to be viewed by a simple lateral flow strip. In addition to the reduced primer requirement, starting with the prefabricated dumbbell loop structure should provide a significant speed advantage. Not having to organically build the initial dumbbell loop structure using primers reduces reaction time, which is also compounded by the fact that amplification and reproduction of the dumbbell loop structure during LAMP will begin immediately.

Example 3.2—TARA-L-LAMP Probe Ligation

In order to test the TARA-L-LAMP probe design, G and A probes were ordered and synthesized with a pair of reactive groups at their 3'- and 5'-ends, respectively. Probe target sequences were chosen to detect various organisms, including but not limited to influenza virus, dengue virus, HCV, malaria, and Opisthorchiid liver flukes. Hairpin stem-loops were designed into one or both probes to prevent non-specific ligation in the absence of a template. G probes were ordered with a 5'-FAM blocking group, which also allowed assessment of ligation by SDS-PAGE. Additionally, a synthetic DNA template was also ordered and synthesized to represent the "target" sequence that would be present in a DNA/RNA molecule of interest. Probes were activated with either FNP or SIA and then heated to 90° C. for 5 min and cooled in a −20° C. freezer to induce secondary structures designed into the 'universal' LAMP adapters, as well as the probe target sequences. TARA-L-LAMP probes were tested in ligation reactions under different conditions, varying reaction times (5-20 min), temperature (55-75° C.) and probe concentration. FIG. 19 shows that the TARA-L-LAMP probes work as designed. A band suggesting proper ligation of the FAM-labelled G probe with the A probe can be seen in "positive" samples, while no band was observed in the "negative" samples (FIG. 19).

Further testing was performed to assess proper probe ligation. Ligated product bands were extracted from the SDS-PAGE, purified with an oligonucleotide clean-up kit, and then quantified by absorbance at 260 nM. Gel-extracted samples for FLU, OLF, MAL and DEN were tested with PCR and LAMP for the ability of the 'ligated' products to amplify. PCR reactions were performed using primers shown in Table 4. PCR products were analyzed on a 3% agarose gel (FIG. 20A) and showed that gel-extracted 'ligated' bands were in fact amplifiable, by the presence of a band of appropriate size (122-125 bp). The positive control consisted of a mock 'ligated' product as the target molecule; G and A probe sequences were concatenated, ordered and synthesized as single DNA molecule. Gel-extracted bands were also tested by LAMP and lateral flow strips (FIG. 20B). LAMP results were congruent with PCR results and demonstrate that the ligated bands observed in the SDS-PAGE were true ligation events and that this ligated product was amplifiable.

Data from other experiments showed the same results, validating the utility of the hairpin stem-loop structures added into probe target sequences in preventing non-specific ligation. TARA-L-LAMP probe ligation is rapid, for both FNP and SIA chemistries, with a 5-min reaction producing similar amount of ligated product as a 15-min reaction. A TARA-ligation reaction temperature of 65° C. was chosen for all further testing, as this is the operating temperature of the downstream LAMP, allowing a single temperature to be used for the entire TARA-L-LAMP assay. The rapidity of the newly designed TARA-L-LAMP probe ligation reaction will significantly shorten the overall NAT time, which is ideal for POC scenarios.

Example 3.3—LAMP Amplification of Mock 'Ligated' TARA Probes

Figure 21:
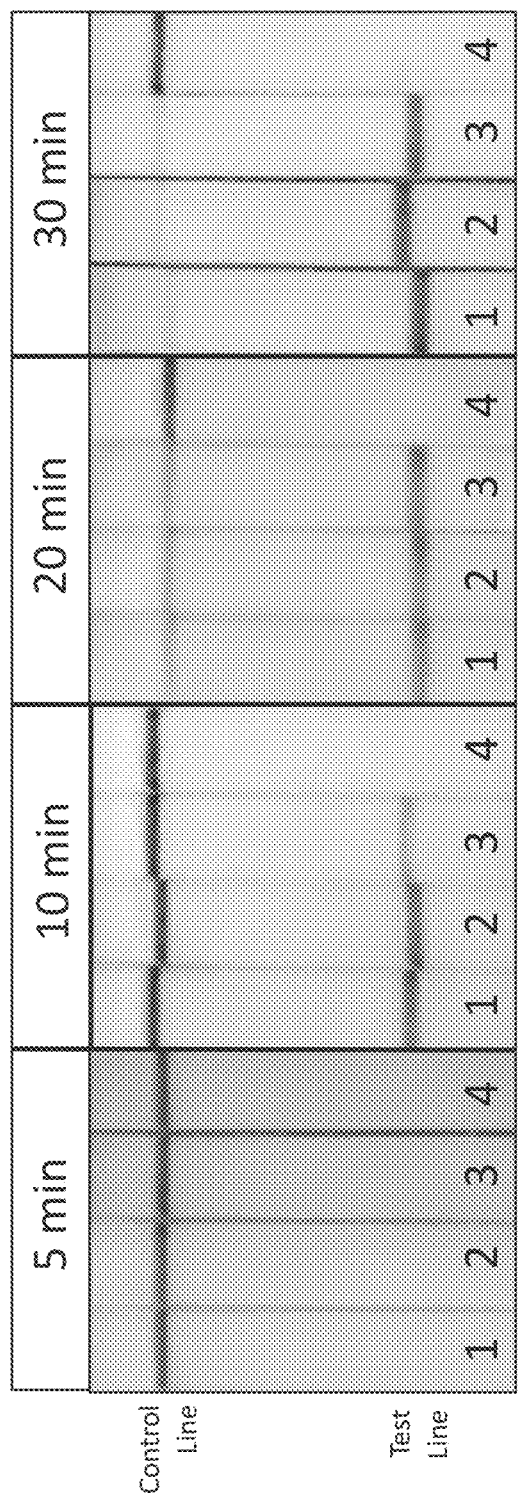
FIG. 21 shows a LAMP assay sensitivity and time test using mock 'ligated' product as the target molecule. Results were viewed by lateral flow strip and showed that LAMP sensitivity was as low as 150 copies in only 10 min at 65° C. No non-specific amplification was observed in the no template control. 1—3,000 copies; 2—300 copies; 3—150 copies; 4—no template control.

LAMP assays were performed using mock 'ligated' product as the target molecule; G and A probe sequences were concatenated, ordered and synthesized as single DNA molecule. The synthetic target molecule was heated to 90° C. for 5 min then cooled in a −20° C. freezer to induce secondary structures designed into the 'universal' LAMP adapters. The target molecule was tested in LAMP assays using different concentrations to establish a base-level sensitivity, as well as different reaction times to see the minimum time required to maintain sensitivity. LAMP-reaction master mix was made by combining 1.6 µM FIP/BIP, 0.8 µM LF/LB, 1× IsoAmp buffer (New England Biolabs), 6 mM additional (8 mM total) $MgSO_4$, 1.4 mM dNTPs, 320 U/ml Bst 2.0 (New England Biolabs), and water to a 20 µl volume per reaction. Different concentrations of mock 'ligated' product were added at 5 µl per reaction (25 µl total reaction volume) and reactions were heated to 65° C. for 5, 10, 20 and 30 min, followed by 85° C. for 2 min to terminate the reaction. LAMP data showed that as little as 150 copies could be consistently and rapidly amplified enough for result viewing on a lateral flow strip, following a LAMP reaction for 10 minutes at 65° C. (FIG. 21). Lower copy numbers were also detectable; however, the consistency with which lower copy numbers could be detected decreased, likely due to the inconsistencies inherent in pipetting and sampling from a solution.

Cumulative data suggests that TARA-L-LAMP could potentially work as a POC assay with results determined in around 15-20 minutes total time. Based on the sensitivity of the downstream LAMP assay and a theoretical workflow established by combining the TARA and LAMP steps (e.g.: run a 50-µl TARA-ligation reaction and then take 5 µl completed TARA as the sample for the LAMP assay), the upstream TARA reaction would require 1,500 copies of template/target to be present in a 50-µl TARA-ligation reaction to be detectable by a 10-min downstream LAMP reaction and lateral flow assessment. By decreasing the volume of the upstream TARA-ligation reaction, to a 25-µl reaction for example, the copies required by the TARA-ligation reaction would decrease to 750 copies. Another adjustment could be to decrease the amount of water in the LAMP-reaction master mix to make it 15 µl per LAMP reaction and use 10 µl of TARA-ligation reaction to maintain the 25-µl total LAMP-reaction volume. This would decrease the copies required in a 50-µl TARA-ligation reaction to 750 copies. Furthermore, decreasing the volume of the TARA-ligation reaction, to a 25-µl reaction for example, would compound the effect and decrease the copy requirement to 375 copies. Similarly, the LAMP-reaction volume could be increased to 50 µl and 10 µl or more of the TARA-ligation reaction could be added, thus decreasing the upstream copy requirement.

Using different 5'-blocking groups as labels and/or adding a barcoding sequence between the two primers sequences within the single stranded region of the dumbbell stem-loop for one or both probes would allow for probe capture, as well as have applications in multiplexing. Barcoding can also be used in conjunction with labeled primers, (one or more of LF, LB, FIP and BIP) to provide multiplexing capabilities by capture and signal reporting.

Example 3.4—LAMP Inhibition by Biological Samples

Figures 22A, 22B, 22C, 22D:
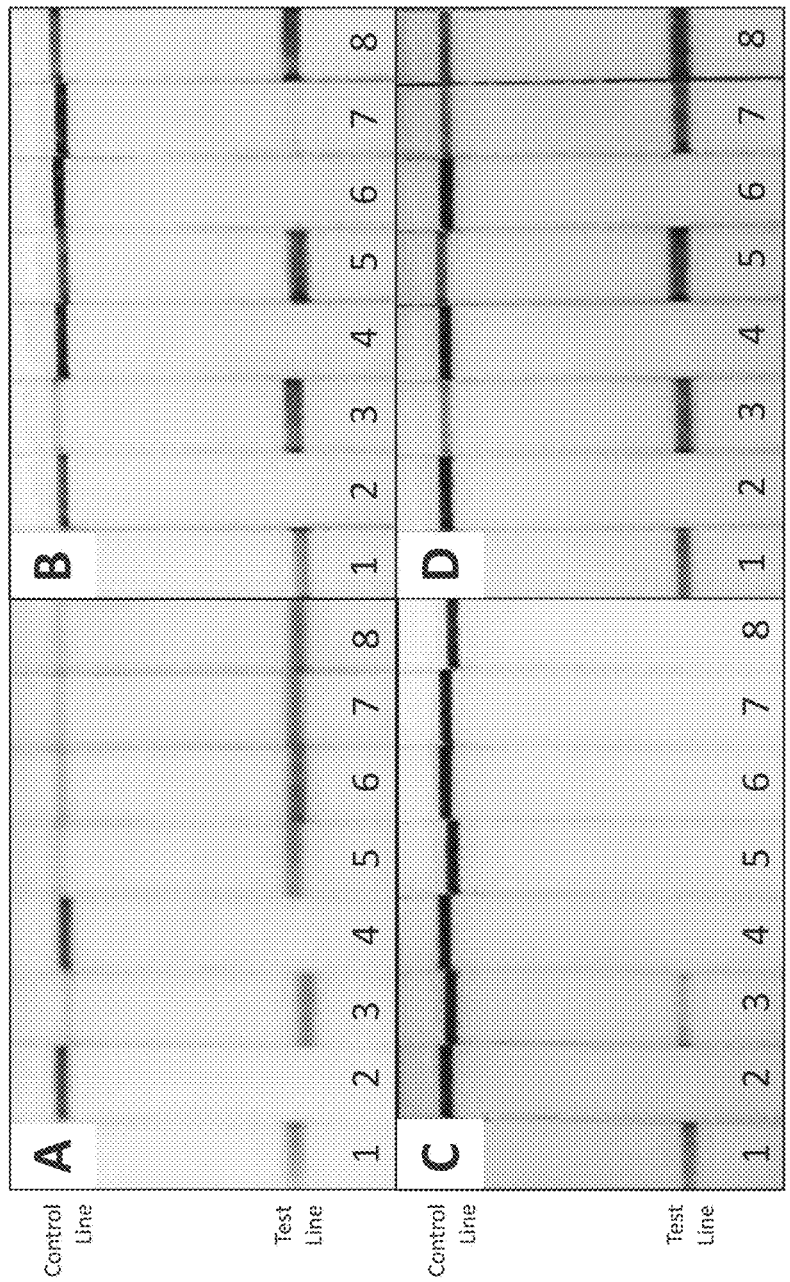
FIGS. 22A-22D show LAMP assays using mock 'TARA' samples. Mock 'TARA' samples were made using CLBuffer-1 spiked with 30,000 copies of mock 'ligated' probes in a 50-μl total reaction volume containing 15 μl of biological material (30%). LAMP assays were run using 5 μl mock 'TARA' reaction per LAMP reaction (3,000 copies of mock 'ligated' probes per LAMP reaction). 1: +control in water; 2: −control in water; 3: +control; 4: −control; 5: saliva; 6: blood plasma; 7: urine; 5: BSA.

LAMP assays were also tested for any possible inhibition by biological samples. Mock 'TARA' samples were made by adding 30,000 copies of mock 'ligated' product to 50-µl reactions (1 fM) containing as much as 15 µl saliva, blood plasma or urine (30% total), or 15 µl 10% BSA (4% total). LAMP reactions were also tested for inhibition by the harsh lysis buffer conditions of CLBuffer-1 and CLBuffer-2. These spiked samples were then tested by LAMP, using 5 µl of mock 'TARA' sample (3,000 copies per LAMP reaction). FIGS. 22A-22D represent one set of experiments to test the effect of lysis buffer and biological material on LAMP performance. CLBuffer-1 alone showed some inhibitory effects when LAMP was run for 10 min (FIG. 22C), but these effects were made negligible by increasing reaction time or reaction volume (FIG. 22D). More significant inhibition was observed in the presence of biological samples (FIG. 22C); however, most of these effects could be alleviated by increasing reaction time (FIGS. 22A-22B). Increasing reaction volume could also lessen inhibition, by basically diluting out inhibitory factors contained in the biological material (FIG. 22D). Blood plasma samples produced the most inhibition, with both increasing reaction volume to 50 µl for 10 min and increasing the 25-µl reaction time to 15 min being unable to regain a positive signal with 3,000 copies (FIGS. 22B and 22D). Urine showed the second most inhibition; however, increasing reaction time or reaction volume was able to combat inhibition (FIGS. 22A, 22B and 22D), with increasing reaction volume recovering the positive band completely (FIG. 22D), while increasing reaction time to 15 min only partially recovered the positive signal, as seen by the faint band produced (FIG. 22B). Increasing the reaction volume to 50 µl permitted detection of 3,000 copies within 10 min for most samples tested, with the exception of blood plasma samples (FIG. 22D). The LAMP assay was also tested with CLBuffer-2. CLBuffer-2 completely inhibited 25-µl LAMP reactions even at 15 min, most likely due to high salt content. Addition of a ligated product capture and wash step would benefit the downstream LAMP assay.

Example 3.5—TARA-L-LAMP Control Experiments

Figure 23:
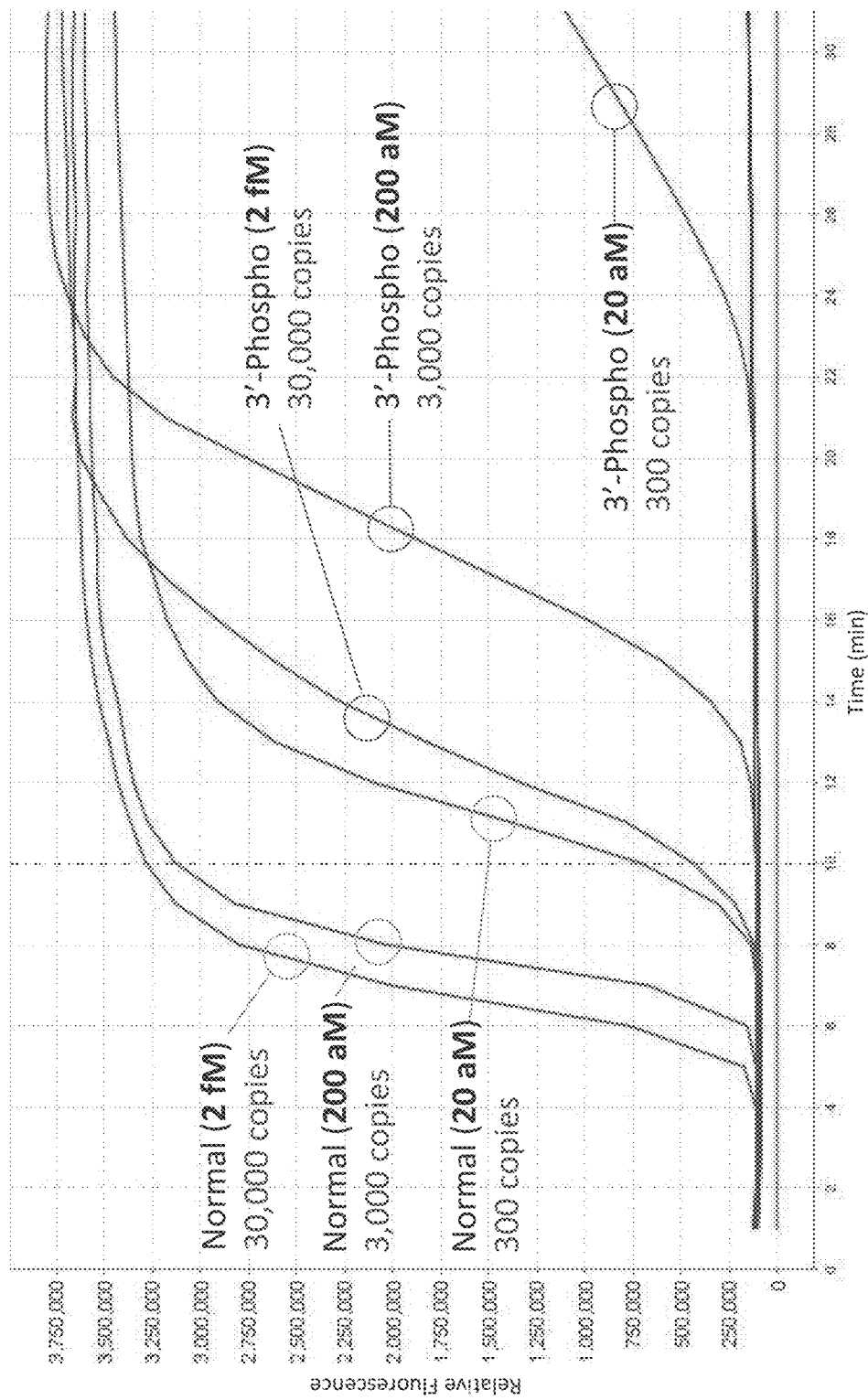
FIG. 23 shows rt-LAMP analysis of mock 'ligated' products, with or without a 3'-blocking group (phosphate) added to the A probe end, at different concentrations. Significant speed/sensitivity reduction is observed when a 3'-blocking group is added.

The designed TARA-L-LAMP probes both contain at least one LAMP-primer binding site, and the A probe structure allows 3' extension and possible amplification in a manner similar to a normal LAMP reaction. As a result, real-time analysis of TARA-L-LAMP is not feasible due to this non-specific amplification of individual probes masking the amplification of true ligated TARA probes; however, rt-LAMP assessment of 'ligated' product is possible due to the absence of probes. Lateral flow assessment of TARA-L-LAMP using tagged loop primers works as designed. The feasibility of limiting the A probe non-specific amplification by addition of a 3'-blocking group was tested. A new mock 'ligated' product ordered with a 3'-phosphate as the blocking group on the A probe end. This new mock 'ligated' product would represent ligation between the G probe and 3'-blocked A probe. Three concentrations (2 fM, 200 aM and 20 aM) of this new mock 'ligated' product, corresponding to 30,000 copies, 3,000 copies and 300 copies, were tested by rt-LAMP and LAMP with lateral flow strip assessment and compared to the unblocked original mock 'ligated' product. Real-time LAMP was carried out for 30 min using LAMP primers (Table 4), with LF/LB being unlabeled, and SYTO-9 for real-time fluorescence monitoring. Results showed a marked decrease in reaction speed/sensitivity between the same concentrations of 3'-blocked mock sample relative to the unblocked mock sample (FIG. 23). The highest concentration tested for the 3'-blocked mock sample amplified slightly slower than the lowest concentration of the unblocked mock sample, with amplification curves starting at approximately 8 min (FIG. 23). Conventional LAMP reactions were carried out for 10 min as described previously and results corroborated rt-LAMP results. At the 10 min LAMP reaction cut-off, only the original mock 'ligated' product produced positive bands on the lateral flow strips, for all three concentrations tested. The highest concentration of the 3'blocked mock 'ligated' product had a faint line while the other two lower concentrations were absent. Data shows that 3'-blocking of the A probe is possible, though sensitivity is compromised. Sensitivity can be restored by increasing the reaction time, but this does not attractive for the rapid POC scenarios.

Moving forward without blocking the 3' end of the A probe, control experiments were performed to assess the effects of each probe on LAMP amplification. LAMP assays were performed on G probe alone (2 nM), A probe alone (2 nM), G and A probes mixed together (2 nM each), and TARA-L-LAMP probe template alone (200 nM), for each of FLU, OLF, MAL and DEN (FIG. 24). A LAMP positive control (1 fM mock 'ligated' product) and LAMP negative control (water) were included. Results show that the probes and template do not produce a positive test line on lateral flow strips (FIG. 24); only the LAMP positive control produced a positive test line. Results for the G and A probe mixture, essentially a TARA-L negative sample (TARA-L with no target molecule present), suggest that the probes perform as designed, preventing non-specific amplification in the absence of a target molecule, as seen by the negative test lines on the lateral flow strips (FIG. 24).

Figure 25:
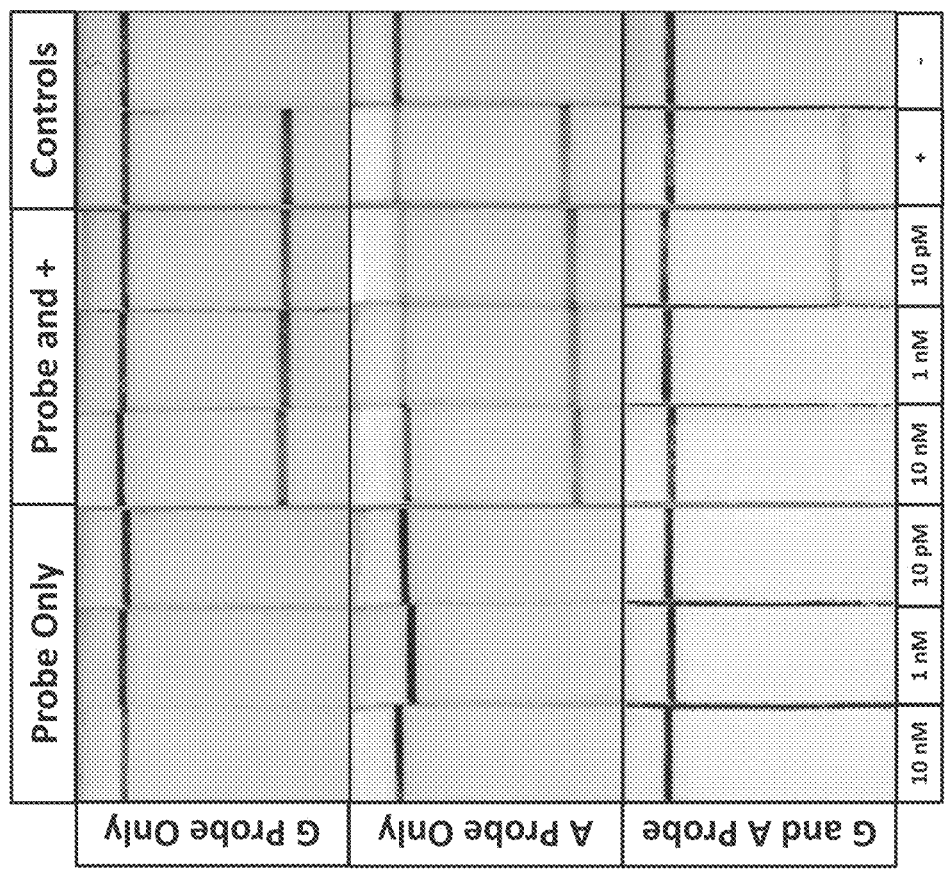
FIG. 25 shows competition tests between probes and mock 'ligated' product during LAMP amplification. Different concentrations (10 nM, 1 nM and 10 pM) of G probe only, A probe only, or G and A probe mixed together were tested with or without spiking with 100 aM (1,500 copies) of mock 'ligated' product and assayed using LAMP. A LAMP positive control (1 fM mock 'ligated' product) and LAMP negative control (water) were included. G probe and A probe alone do not appear to inhibit LAMP and lateral flow strip assessment of the mock 'ligated' product; however, mock 'ligated' product failed to produce a positive test line when mixed with 10 nM or 1 nM G and A probe.

As stated previously, the designed TARA-L-LAMP probes both contain at least one LAMP-primer binding site, and the A probe structure allows 3' extension and possible amplification in a manner similar to a normal LAMP reaction. LAMP assays were performed to assess any potential inhibition by the presence of probes in the LAMP reaction by competition with the ligated product for reagents and/or primers. Three different concentrations (10 nM, 1 nM and 10 pM) of G probe alone, A probe alone, or G and A probe mixed together were tested with or without spiking by mock 'ligated' product (3,000 copies) by LAMP and lateral flow strip (FIG. 25). Results indicate that the presence of the G probe or A probe in the LAMP reaction does not affect the result of the lateral flow strip. By contrast, presence of both G and A probes in the LAMP reaction inhibited the LAMP reaction for the two highest concentrations (10 nM and 1 nM) tested (FIG. 25). Results suggest that decreasing the amount of probes used for the TARA reaction will alleviate inhibition of the LAMP reaction due to probes competing for LAMP reagents and primers. Additionally, capturing one of the probes, and thereby also capturing the ligated product, and washing away the other, is another means of reducing/preventing any potential inhibition by the probes competing for reagents/primers.

When combined with previous data from LAMP inhibition tests using CLBuffers and biological material, a capture and wash step prior to the LAMP assay is preferable to reduce/eliminate all potential forms of LAMP inhibition. The capture step can be performed in a variety of ways such as, but not limited to, antibody-, avidin-, or nucleic acid-coated areas on a solid surface like a lateral flow strip, antibody-, avidin-, or nucleic acid-coated tubes or antibody-, avidin-, or nucleic acid-coated magnetic beads.

Example 3.6—TARA-L-LAMP Multiplex Capabilities

TARA-L-LAMP probes were also designed for multiplexing (FIG. 26A). Unique barcode sequences are inserted between the LB and B2c sequences located in the single-stranded loop portion of the A probe. Corresponding reverse complement sequences are inserted between the F2 and LFc sequences located in the single-stranded loop portion of the G probe. Probe sets designed to detect different targets have their own unique barcode sequences. The ligated products produce a dumbbell structure 1. Early in the LAMP amplification cascade, LAMP amplification of dumbbell structure 1 by BIP primers 5'-tagged with a reporter generate dumbbell structure 2, as well as a larger more complex product (FIG. 26B). The larger product continues in the LAMP cascade to produce complex products of increasing size and complexity. Dumbbell structure 2 contains the 5' reporter and barcode sequence in the 3' end stem loop. LAMP amplification of dumbbell structure 2 by FIP primers 5'-tagged with a reporter regenerate dumbbell structure 1, as well as a larger more complex product that is essentially the reverse complement of the one produced by dumbbell structure 1 (FIG. 26B). This larger product also continues in the LAMP cascade to produce complex products of increasing size and complexity. All products with a 5' reporter tag and a barcode sequence located in a single-stranded loop region are detectable by lateral flow assay. Specific oligonucleotides complementary to each unique barcode sequence allow selective capture of specific products within the lateral flow strip for multiplexing.

Example 4.1—TARA-L-PCR Versus TARA-L-RPA

An isothermal amplification method, recombinase polymerase amplification (RPA), was used in some experiments in place of traditional PCR. Table 5 provides the primer and probe sequences for RPA amplification.

TABLE 5

RPA primer and probe sequences for detection of LHIV-1.

| Primer or Probe | Sequences (5'→3') |
|---|---|
| Nfo probe | FAM-CAATCTATGTTTTCAGCATTATCAGAAGG(THF)GCCACCCCACAAGATT(ddT) (SEQ ID NO: 27) |
| Forward RPA primer | GTGCCAGCAAGATCCAATCTATGTTTTCAGC (SEQ ID NO: 28) |
| Reverse RPA primer | BIOTIN-GGGTTCCCTAAGGGTTGGTTTAGCATG GTGT (SEQ ID NO: 29) |

TARA-L-PCR reactions were carried out with the following conditions: A PCR mixture was prepared by mixing Universal Primers (250 nM Biotin-UF/FITC-UR) with PCR Master Mix (Luna® Universal qPCR Probe Mix, 1×). Then 2 µl of TARA-L products were added into each 18 µl PCR mixture. The PCR parameters were as follows: 95° C. for 1 min, followed by 25 cycles of 95° C. for 15 s, 60° C. for 30 s, and 72° C. for 30 s. Lateral flow strips were manufactured in house. Test lines (Neutravidin in 1×PBS, pH 7.4, 2.5 mg/ml) and control lines (goat anti-mouse IgG or GAM in 1×PBS, pH 7.4, 0.8 mg/ml) were coated at 1 µl/cm on nitrocellulose membrane (CN 140, Sartorius) using a Biodot XYZ3000 coating machine. Gold nanoparticles were synthesized using Turkevich method (40 nm), which were conjugated to FITC antibody (ThermoFisher #31242) by physical adsorption. Gold nanoparticle conjugates were dried on polyester conjugate pad (6613H, Ahlstrom) and assembled onto backing cards with 1-2 mm overlapping on the nitrocellulose membranes. Cellulose pads (CFS, GE Whatman) were assembled as absorbent pads with 1-2 mm overlapping onto nitrocellulose membranes. Assembled backing cards were cut into 3 mm strips using a Biodot strip cutter. TARA-L products, after cooling to room temperature, were directly applied (2 µl) to the conjugate pads of the strips. Then, strips were dipped into 50 µl chase buffer (1×PBS, pH 7.4, 0.5% (v/v) Tween-20) for 10 min before observation and/or photograph.

TARA-L-RPA reactions were carried out with the following conditions: RPA kits (TwistAmp® nfo kit, designed for lateral flow strip detection) were ordered from TwistDx. For RPA amplification, a whole new set of primers and an nfo probe were designed (Table 5) for LHIV-1 templates (Table 3). A typical 50 µl RPA reaction contains 29.5 µl of rehydration buffer, 8.2 µl of water, 2.1 µl of Forward RPA primer (10 µM), 2.1 µl of Reverse RPA primer (10 µM), 0.6 µl of RPA probe (10 µM), and 5 µl of TARA-L ligation products. In each 50 µL reaction, one enzyme pellet was added. The addition of 2.5 µl magnesium acetate (280 mM) starts the RPA amplification. The reactions were subjected to an initial incubation at 37° C. for 4 min first, then samples were vortexed for 5 seconds before another incubation at 37° C. for 30 min. The RPA-amplified TARA-L samples were then applied onto strips for detection.

Figure 27A:
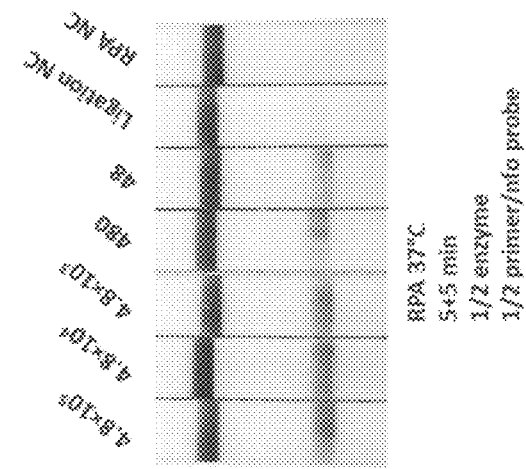
FIG. 27A-27C show parallel comparisons between TARA-L-PCR and TARA-L-RPA.
Figure 27B:
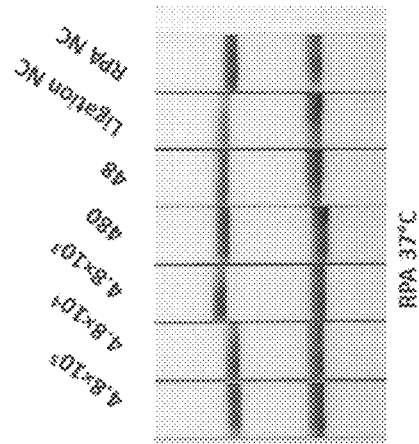

FIGS. 7A27A-27C show parallel comparisons between TARA-L-PCR and TARA-L-RPA. TARA reactions were performed as described previously, using serial dilutions of LHIV-1 template. TARA-L-PCR was carried out and 2 µl of each reaction were applied to lateral flow strips. FIG. 7A27A shows there was no non-specific test line for the PCR negative control (with PCR primers, without TARA-L sample). Additionally, there was no test line for TARA-L negative control (both G and A probes, no LHIV-1 template, PCR with primers). The 48 copy per test showed a much higher intensity test line than that of ligation negative control (FIG. 7A27A). FIG. 7B27B shows that with a typical RPA amplification protocol, TARA-L-RPA shows very high non-specific test lines for both the RPA negative control and TARA-L negative control, when reactions were directly applied to lateral strips without dilution.

Figure 27C:
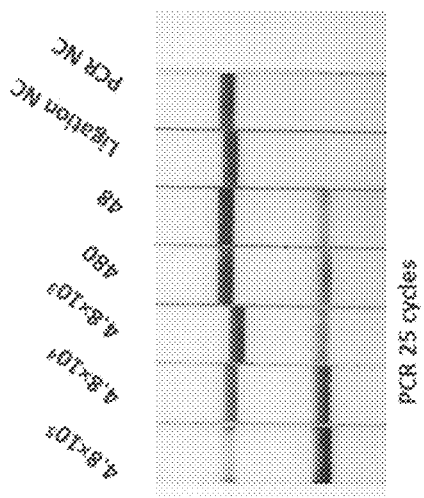

RPA reaction conditions were then optimized in order to maintain the high sensitivity, while removing the non-specific test lines from the negative controls. Additionally, TARA-L samples were buffer exchanged using G-25 columns into water due to the strong influence of CLBuffer-2 on RPA. The concentrations of enzyme pellet, RPA primer, and RPA probe were decreased to half of their original concentrations. Also, the RPA reactions incubated initially at 37° C. for 5 min instead of 4 min. After vortexing, reactions were incubated at 37° C. for another 5 min, instead of 30 min, before 2 µl of reaction were applied to strips. The results in FIG. 27C show that TARA-L-RPA was able to reach equal or better sensitivity within 10 min when compared TARA-L-PCR amplification for 25 cycles. Positive TARA-L-RPA reactions containing LHIV-1 template (48 copies per test) showed an obvious test line on strips, while the TARA-L and RPA negative controls did not show test lines (FIG. 27C).

Example 5. Single-Nucleotide Polymorphism (SNP) Detection Using TARA-L

Example 5.1. Single-Nucleotide Polymorphism (SNP) Detection in LHIV

Template sequences for LHIV-1 were designed to incorporate one mismatch or two mismatches close to the meeting point of two probes, when probes were hybridized with the template. If this meeting point was designated as position zero (0), the $n^{th}$ nucleotide to the 3'-end side of the template was position +n. Similarly, the $n^{th}$ nucleotide to the 5'-end side of the template was position −n. Table 6 lists the sequences of wild-type and mutated templates. LHIV-1M had one mismatch at +4 site; LHIV-1M2 had one mismatch at +1 site; LHIV-1M3 had one mismatch at −1 site; LHIV-1M4 had two mismatches at −1 and −2 sites; LHIV-1M5 had one mismatch at −3 site; LHIV-1M6 had two mismatches at −3 and −4 sites.

TABLE 6

Sequences of wild-type and mutated templates for LHIV-1.

| Template | Sequence (5'→3') |
|---|---|
| LHIV-1 | 5'-ATG TTT TCA GCA TTA TCA GAA GGA GCC A\|CC CCA CAA GAT TTA AAC ACC ATG CTA AAC-3' (SEQ ID NO: 30) |
| LHIV-1M | 5'-ATG TTT TCA GCA TTA TCA GAA GGA GCC A\|CC CGA CAA GAT TTA AAC ACC ATG CTA AAC-3' (SEQ ID NO: 31) |
| LHIV-1M2 | 5'-ATG TTT TCA GCA TTA TCA GAA GGA GCC A\|GC CCA CAA GAT TTA AAC ACC ATG CTA AAC-3' (SEQ ID NO: 32) |
| LHIV-1M3 | 5'-ATG TTT TCA GCA TTA TCA GAA GGA GCC T\|CC CCA CAA GAT TTA AAC ACC ATG CTA AAC-3' (SEQ ID NO: 33) |

TABLE 6-continued

Sequences of wild-type and mutated templates for LHIV-1.

| Template | Sequence (5'→3') |
|---|---|
| LHIV-1M4 | 5'-ATG TTT TCA GCA TTA TCA GAA GGA GCA T\|CC CCA CAA GAT TTA AAC ACC ATG CTA AAC-3' (SEQ ID NO: 34) |
| LHIV-1M5 | 5'-ATG TTT TCA GCA TTA TCA GAA GGA GAC A\|CC CCA CAA GAT TTA AAC ACC ATG CTA AAC-3' (SEQ ID NO: 35) |
| LHIV-1M6 | 5'-ATG TTT TCA GCA TTA TCA GAA GGA TAC A\|CC CCA CAA GAT TTA AAC ACC ATG CTA AAC-3' (SEQ ID NO: 36) |

|: probe junction site

Figure 28:
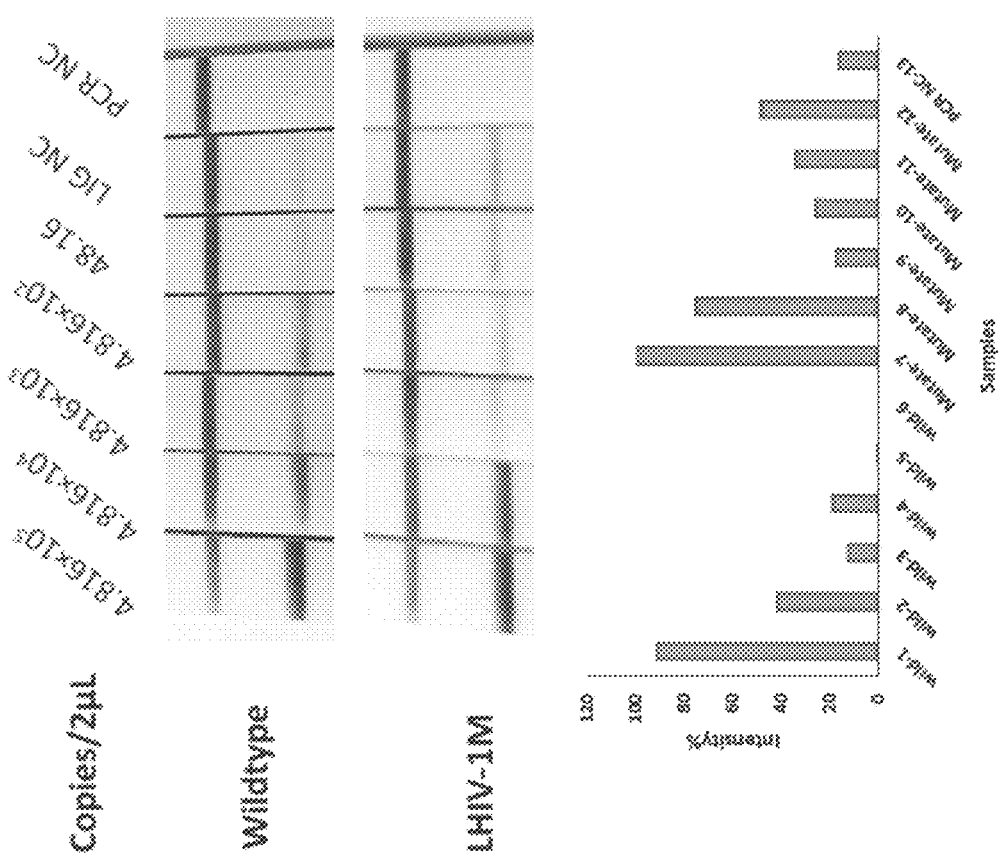
FIG. 28 shows a TARA-L-PCR assay of a mutated ssDNA sequence (LHIV-1M) with a mismatched nucleotide at site +4. LHIV-1M was used as the template for TARA-L reactions at different concentrations, which was then subsequently amplified by PCR (2 μl per reaction) and applied to strips (2 μl per strip). The results were compared with that of wild-type template (LHIV-1). LIG NC is a negative control for TARA ligation that contained probes only (no template). PCR NC is a negative control for PCR that contained only PCR master mix (no TARA-L product).

TARA-L-PCR reactions were performed as described previously, with 2-5 µl of reaction used per strip. FIG. 28 shows lateral flow strip assessment of TARA-L-PCR results, comparing LHIV-1M with the wild-type LHIV-1. LHIV-1M did not show inferior performance as a template when compared with the wildtype LHIV-1. In contrast, LHIV-1M showed slightly better performance as a template for TARA-L reaction.

Figure 29:
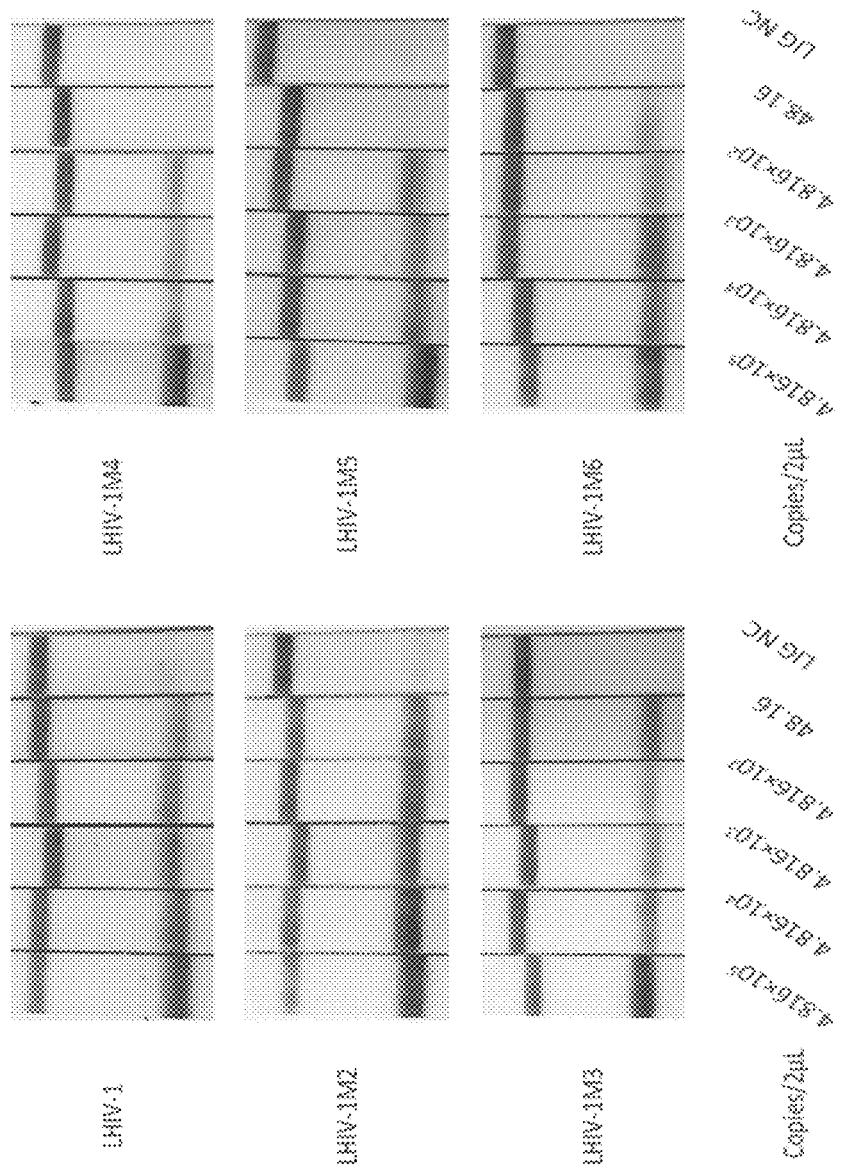
FIG. 29 shows TARA-L-PCR assays of mutated ssDNA sequences (LHIV-1M2, LHIV-1M3, LHIV-1M4, LHIV-1M5, and LHIV-1M6) with mismatched nucleotides at various sites. These were used as templates for TARA-L reactions at different concentrations, which was then subsequently amplified by PCR (2 µl per reaction) and applied to strips (2 µl per strip). The results were compared with that of wild-type template (LHIV-1). LIG NC is a negative control for TARA ligation that contained probes only (no template).

FIG. 29 shows a comparison of results for LHIV-1M2, LHIV-1M3, LHIV-1M4, LHIV-1M5, and LHIV-1M6, with the wild-type LHIV-1 as templates for TARA-L-PCR. When comparing results for the same serial-diluted concentrations of template, the most obvious observation was that LHIV-1M4 and LHIV-1M5 did not show test line for the lowest concentration of 48.16 copies/strip, while other mutated templates, including LHIV-1M2, LHIV-1M3 and LHIV-1M6, and the wild-type template LHIV-1 showed obvious test lines.

Figure 30:
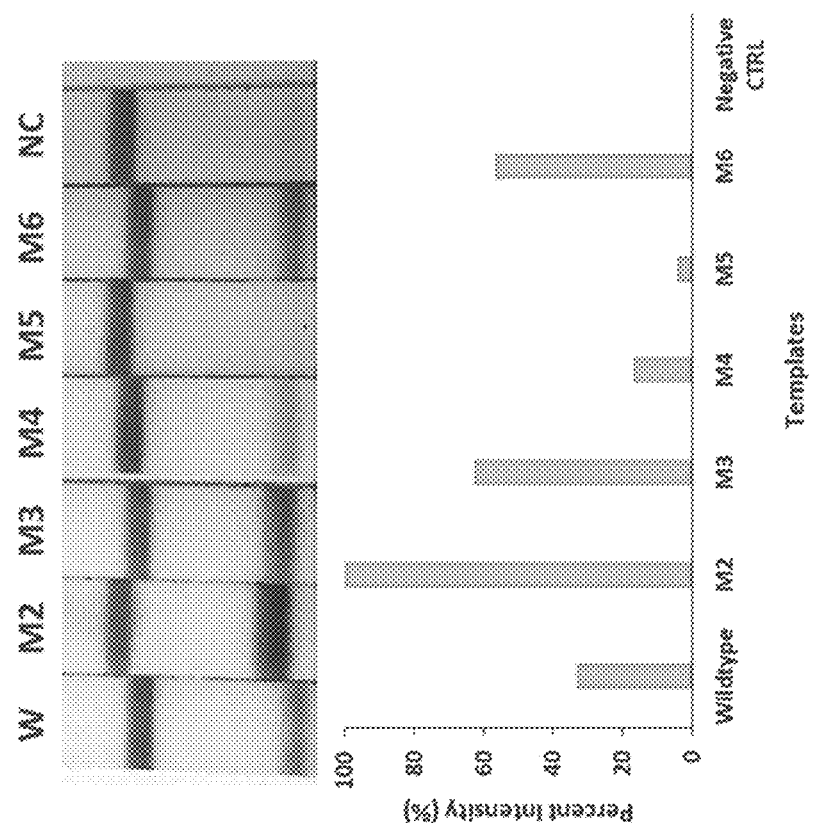
FIG. 30 shows TARA-L-PCR assays of mutated ssDNA sequences (LHIV-1M2, LHIV-1M3, LHIV-1M4, LHIV-1M5, and LHIV-1M6) with mismatched nucleotides at various sites. These were used as the templates for TARA-L-PCR reactions at a concentration of $4 \times 10^{10}$ µM, which was then subsequently amplified by PCR (2 µl per reaction) and applied to strips (2 µl per strip). The results were compared with that of wild-type template (LHIV-1). NC is a negative control for TARA ligation that contained probes only (no template).

In FIG. 30, TARA-L-PCR reactions were repeated at a single concentration of 48.16 copies/strip and results were compared. LHIV-1M2 showed consistently better performance than the wild-type, while LHIV-1M4 and LHIV-1M5 showed lower test line intensities than that of wild-type, confirming the results in FIG. 29.

Example 5.2. Single-Nucleotide Polymorphism (SNP) Detection in Influenza A

Similar experiments were performed using TARA probes and template for a different virus, influenza A. Table 7 lists the sequences of TARA probes and wild-type and mutated templates. FLUA1-M1 had one mismatch at −3 site; FLUA1-M2 had two mismatches at −3 and −4 sites; FLUA1-M3 had three mismatches at −3, −4 and −5 sites; FLUA1-K1 had one mismatch at +1 site.

TABLE 7

Sequences of probes and wild-type and mutated templates for influenza A.

| | Oligo | Sequence (5'→3') |
|---|---|---|
| Probes | FLUA1-G | BIOTIN-GGG TTC CCT AAG GGT TG CAT TTT GGA CAA AGC GTC TAC GC-PS (SEQ ID NO: 37) |
| | FLUA1-A | Amino-dT-GCA GTC CTC GCT CAC TGA GAT TGG ATC TTG CTG GCA C -FAM (SEQ ID NO: 38) |

TABLE 7-continued

Sequences of probes and wild-type and mutated templates for influenza A.

| | Oligo | Sequence (5'→3') |
|---|---|---|
| Template | FLUA1-WT | CCC AGT GAG CGA GGA CTG CA\|G CGT AGA CGC TTT GTC CAA AAT GC (SEQ ID NO: 39) |
| | FLUA1-M1 | CCC AGT GAG CGA GGA CTA CA\|G CGT AGA CGC TTT GTC CAA AAT GC (SEQ ID NO: 40) |
| | FLUA1-M2 | CCC AGT GAG CGA GGA GGA CA\|G CGT AGA CGC TTT GTC CAA AAT GC (SEQ ID NO: 41) |
| | FLUA1-M3 | CCC AGT GAG CGA GGA GGA CA\|G CGT AGA CGC TTT GTC CAA AAT GC (SEQ ID NO: 42) |
| | FLUA1-K1 | CCC AGT GAG CGA GGA CTG CA\|C CGT AGA CGC TTT GTC CAA AAT GC (SEQ ID NO: 43) |

|: probe junction site

Probes G (FNP-activated, 0.1 µM, 2 µl) and A (0.1 µM, 2 µl) were mixed with serial-diluted templates (1 µM, 0.1 µM (100 nM), 0.01 µM (10 nM), $10^{-3}$ µM (1 nM), $10^{-4}$ µM (100 pM), $10^{-5}$ µM (10 pM), $10^{-6}$ µM (1 pM), $10^{-7}$ µM (100 fM), $10^{-8}$ µM (10 fM), and $10^{-9}$ µM (1 fM)) and water to create a 50-µl TARA reaction. TARA reactions were incubated at 55° C. for 10 min and then 2 µl of TARA-L reaction products were mixed with 18 µl of LUNA® master mix for rt-PCR. rt-PCR reaction conditions were as follows: 95° C. for 1 min, followed by 40 cycles of 95° C. for 15 s, 60° C. for 30 s, and 75° C. for 30 s. Threshold cycle (CO values were normalized, with the wild-type assumed to be 100% and the water blank control being considered 0% (FIG. 31). FIG. 31 shows that relative amplification values for $10^{-5}$ µM (10 pM) correlated inversely to the number of mutations contained within the template; more mutations within the template produced higher $C_t$ value, and thus a lower amplification level was obtained. It is interesting to note that mutation K1 produced a higher relative amplification level than M1. Data from both LHIVL and FLU experiments suggest that TARA-L methods can utilize probes to differentiate analytes with mutations at specific sites.

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting.

As used in this specification and claims, the singular forms "a," "an" and "the" include plural references unless the content clearly dictates otherwise.

As used herein, "about" means a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

Although this disclosure is in the context of certain embodiments and examples, those skilled in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

What is claimed is:

1. A method of determining the presence of a target nucleic acid in a sample, the method comprising:

contacting the sample with a reaction mixture comprising at least one set of chemically-reactive probes, the at least one set of chemically-reactive probes comprising:

a plurality of a first probe, the first probe comprising a first nucleic acid region that is complementary to a first part of the target nucleic acid sequence and a first chemical group at a 3'end of the first nucleic acid region selected from a 2-Fluoro-5-nitropyridine (FNP) group, a 1-Fluoro-2,4,6-Trinitrobenzene (FNTB) group, a succinimidyl iodoacetate (SIA) group, an amine (NH2) group, thiophosphate (PS) group, or hydroxyl (OH) group, and a plurality of a second probe, the second probe comprising a second nucleic acid region complementary to a second, different part of the target nucleic acid sequence and a second, different chemical group at a 5'end of the second nucleic acid region selected from a 2-Fluoro-5-nitropyridine (FNP) group, a 1-Fluoro-2,4,6-Trinitrobenzene (FNTB) group, a succinimidyl iodoacetate (SIA) group, an amine (NH2) group, a thiophosphate (PS) group, or a hydroxyl (OH) group, wherein the first and second parts of the target nucleic acid sequence are separated by 10 nucleotides or less, wherein in the presence of the target nucleic acid in the sample the first probe and second probe anneal to the first and second parts of the target nucleic acid sequence and ligate together through a chemical ligation reaction between the first chemical group and the second chemical group to form a chemically ligated product; and detecting the chemically ligated product by capturing and visualizing the chemically ligated product on an immunochromatographic test strip, wherein detection of the chemically ligated product indicates the presence of the target nucleic acid in the sample, and wherein:

when the first chemical group at a 3'end of the first nucleic acid sequence is 2-Fluoro-5-nitropyridine (FNP) or a 1-Fluoro-2,4,6-Trinitrobenzene (FNTB) group, the second, different chemical group at a 5'end of the second nucleic acid, is an amine ($NH_2$), thiophosphate (PS), or hydroxyl (OH) group, when the first chemical group at a 3'end of the first nucleic acid sequence is an amine ($NH_2$), thiophosphate (PS), or hydroxyl (OH) group, the second, different chemical group at a 5'end of the second nucleic acid, is a 2-Fluoro-5-nitropyridine (FNP) group or a 1-Fluoro-2,4,6-Trinitrobenzene (FNTB) group, when the first chemical group at a 3'end of the first nucleic acid sequence is a hydroxyl (OH) group, the second, different chemical group at a 5'end of the second nucleic acid, is a succinimidyl iodoacetate (SIA) group, and when the first chemical group at a 3'end of the first nucleic acid sequence is a succinimidyl iodoacetate (SIA) group, the second, different chemical group at a 5'end of the second nucleic acid, is a hydroxyl (OH) group.

2. The method of claim 1, wherein the chemical ligation reaction comprises activation of the first chemical group or the second chemical group by an activator and ligation of the activated first chemical group or the activated second chemical group to the second chemical group or the first chemical group, respectively.

3. The method of claim 1, wherein the sample is contacted with the reaction mixture at a temperature of 50 to 60° C.

4. The method of claim 1, wherein detecting the chemically ligated product by capturing and visualizing the chemically ligated product on an immunochromatographic test strip is performed at room temperature within 5 to 10 min of contacting the sample with the reaction mixture.

5. The method according to claim 1, wherein the target nucleic acid sequence is not amplified prior to contacting the sample with the reaction mixture.

6. The method according to claim 1, wherein the sample comprises a nasal swab, nasal aspirate, oropharyngeal swab, urine, sweat, tears, lymph, plasma, serum, saliva, semen, cerebrospinal fluid, synovial fluid, or blood.

7. The method according to claim 1, wherein the method comprises contacting the sample with one or more additional sets of probes, each additional set of probes being configured to ligate in the presence of a different target nucleic acid sequence.

8. The method according to claim 1, further comprising amplifying the chemically ligated product prior to detecting the chemically ligated product by capturing and visualizing the chemically ligated product on an immunochromatographic test strip.

9. The method according to claim 8, wherein the first and second probes further comprise universal primer sequences, specific primer sequences, or both.

10. The method according to claim 9, wherein the first and second probes further comprise universal or specific adapter sequences.

11. The method according to claim 10, wherein the adapter sequences further comprise at least one barcode sequence.

12. The method according to claim 9, wherein the first probe comprises an adapter sequence that is blocked at the 5' end with a blocking group.

13. The method according to claim 12, wherein the blocking group is selected from a group consisting of biotin, FITC, FAM, phosphate, and C3-spacer.

14. The method according to claim 9, wherein the universal or specific primers sequences are located 5' to the first nucleic acid region of the first probe and 3' to the second nucleic acid region of the second probe.

15. The method according to claim 8, wherein the amplification is selected from the group consisting of chemical ligation-based template assisted rapid assay polymerase chain reaction (TARA-L-PCR), TARA-L-recombinase-polymerase amplification (TARA-L-RPA), and TARA-L-loop-mediated isothermal amplification (TARA-L-LAMP).

16. The method of claim 8, wherein the chemically ligated product is amplified by an isothermal amplification process selected from the group consisting of loop-mediated isothermal amplification (LAMP) and recombinase-polymerase amplification (RPA).

17. The method according to claim 1, wherein at least one of the first and second probes comprises a reporter.

18. The method according to claim 17, wherein the reporter is configured for detection, product capture, multiplexing, or a combination thereof.

19. The method according to claim 17, wherein the reporter is selected from a group consisting of biotin, FITC, FAM and digoxin.

20. The method of claim 1, wherein the first chemical group is a thiophosphate group.

21. The method of claim 1, wherein the second chemical group is a primary amine.

22. A method of diagnosing a condition in a subject, the method comprising:
obtaining a sample from the subject that may comprise a target nucleic acid associated with the condition;
contacting the sample with a reaction mixture comprising at least one set of probes, the at least one set of probes comprising:
a plurality of a first probe comprising a first nucleic acid region that is complementary to a first part of the target nucleic acid sequence and a first thiophosphate group at a 3' end, and
a plurality of a second probe, the second probe comprising a second nucleic acid region complementary to a second, different part of the target nucleic acid sequence and a 2-Fluoro-5-nitropyridine (FNP) group or a 1-Fluoro-2,4,6-Trinitrobenzene (FNTB) group at a 5' end,
wherein the first part and the second part of the target nucleic acid sequence are separated by 0 to 10 nucleotides;
wherein in the presence of the target nucleic acid sequence the first and second products are ligated through a reaction between the thiophosphate group and the primary amine group to form a chemically ligated product; and
detecting the chemically ligated product by immunochromatographic analysis on an immunochromatographic test strip,
wherein detection of the chemically ligated product diagnoses the condition in the subject.

23. The method according to claim 22, wherein the target nucleic acid is from a bacterium, fungus, virus, or parasite.

24. The method according to claim 23, wherein the target nucleic acid is from a virus selected from the group consisting of dengue virus, influenza virus, chikungunya virus, the human immunodeficiency virus (HIV), the hepatitis C virus (HCV), human papillomavirus (HPV), Middle East respiratory syndrome (MERS) virus, arboviruses, respiratory syncytial virus (RSV; also known as human orthopneumovirus), coronavirus, and Ebola virus.

25. The method according to claim 23, wherein the bacterium is methicillin-resistant *genus species* (MRSA).

26. The method according to claim 23, wherein the parasite is selected from the group consisting of *Plasmodium falciparum* (malaria), *Candida auris* and Opisthorchiid liver flukes consisting of *Opisthorchis sinensis* (also known as *Clonorchis sinensis*), *Opisthorchi viverrini* and *Opisthorchis felineus*.

27. The method according to claim 22, wherein the target nucleic acid comprises RNA, DNA or microRNA.

28. The method according to claim 22, wherein the sample comprises a nasal swab, nasal aspirate, oropharyngeal swab, urine, sweat, tears, lymph, plasma, serum, saliva, semen, cerebrospinal fluid, synovial fluid, or blood.

\* \* \* \* \*

UNITED STATES PATENT AND TRADEMARK OFFICE
CERTIFICATE OF CORRECTION

PATENT NO. : 11,685,960 B2
APPLICATION NO. : 16/868403
DATED : June 27, 2023
INVENTOR(S) : HyunDae Cho It is certified that error appears in the above-identified patent and that said Letters Patent is hereby corrected as shown below:

On the Title Page

Column 2 (Other Publications), Line 8, delete "Reserach" and insert -- Research --.

Page 2, Column 1 (Other Publications), Line 2, delete "Dased" and insert -- Based --.

Page 2, Column 1 (Other Publications), Line 6, delete "pii:" and insert -- pp. --.

Page 2, Column 1 (Other Publications), Line 66, delete "Carbodhmide" and insert -- Carbodiimide --.

In the Specification

Column 3, Line 9, delete "emodiments," and insert -- embodiments, --.

Column 9, Line 13, delete "ligate" and insert -- ligate. --.

Column 10, Line 54, delete "FIG." and insert -- FIGS. --.

Column 11, Line 40, delete "hyrdoxyl" and insert -- hydroxyl --.

Column 23, Line 9, delete "isothicyanate" and insert -- isothiocyanate --.

Column 25, Line 56, delete "polyacrilymide" and insert -- polyacrylamide --.

Column 29, Line 28, delete "assessment)" and insert -- assessment. --.

Column 29, Line 65, delete "sequences" and insert -- sequences. --.

Column 31, Line 24, line After "materials" delete "can be".

Signed and Sealed this
Tenth Day of October, 2023

Katherine Kelly Vidal
*Director of the United States Patent and Trademark Office*

CERTIFICATE OF CORRECTION (continued)
U.S. Pat. No. 11,685,960 B2

Column 31, Line 48, line After "limited" delete "by".

Column 36, Line 13, line After "sample," delete "the".

Column 38, Line 37, delete "embodients" and insert -- embodiments --.

Column 40, Line 59 (approx.), delete "polyacrilymide" and insert -- polyacrylamide --.

Column 41, Line 48, delete "FIG." and insert -- FIGS. --.

Column 45, Line 10, delete "(CO" and insert -- ($C_t$ --.

Column 52, Line 36, delete "(CFS," and insert -- (CF5, --.

Column 52, Line 61, delete "FIGS. 7A27A-27C" and insert -- FIGS. 27A-27C --.

Column 52, Lines 65-66, delete "FIG. 7A27A" and insert -- FIG. 27A --.

Column 53, Line 5, delete "(FIG. 7A27A)" and insert -- (FIG. 27A) --.

Column 53, Line 5, delete "FIG. 7B27B" and insert -- FIG. 27B --.

Column 55, Line 32, delete "(CO" and insert -- ($C_t$ --.

In the Claims

Column 73, Line 55, In Claim 1, delete "(NH2)" and insert -- ($NH_2$) --.

Column 73, Line 64, In Claim 1, delete "(NH2)" and insert -- ($NH_2$) --.

Column 76, Line 57, In Claim 25, delete "genus species" and insert -- staphylococcus aureus --.

SEQUENCE LISTING

<160> NUMBER OF SEQ ID NOS: 43

<210> SEQ ID NO 1
<211> LENGTH: 27
<212> TYPE: DNA
<213> ORGANISM: Artificial
<220> FEATURE:
<223> OTHER INFORMATION: Synthetic; Mir21-G Probe;
      5' Biotin modification; 3' Chemical modification

<400> SEQUENCE: 1
gggttcccta agggttgtca acatcag                                      27

<210> SEQ ID NO 2
<211> LENGTH: 32
<212> TYPE: DNA
<213> ORGANISM: Artificial
<220> FEATURE:
<223> OTHER INFORMATION: Synthetic; Mir21-A Probe;

5' Chemical modification; 3' Fluorescein modification

<400> SEQUENCE: 2
tctgataagc taagattgga tcttgctggc ac                32

<210> SEQ ID NO 3
<211> LENGTH: 29
<212> TYPE: DNA
<213> ORGANISM: Artificial
<220> FEATURE:
<223> OTHER INFORMATION: Synthetic; Mir21 Template

<400> SEQUENCE: 3
tagcttatca gactgatgtt gaattaaaa                    29

<210> SEQ ID NO 4
<211> LENGTH: 28
<212> TYPE: DNA
<213> ORGANISM: Artificial
<220> FEATURE:
<223> OTHER INFORMATION: Synthetic; Mir495-G Probe;
    5' Biotin modification; 3' Chemical modification

<400> SEQUENCE: 4
gggttcccta agggttgcga aaataaca                     28

<210> SEQ ID NO 5
<211> LENGTH: 31
<212> TYPE: DNA
<213> ORGANISM: Artificial
<220> FEATURE:
<223> OTHER INFORMATION: Synthetic; Mir495-A Probe;
    5' Chemical modification; 3' Fluorescein modification

<400> SEQUENCE: 5
tgggcaactt cagattggat cttgctggca c                 31

<210> SEQ ID NO 6
<211> LENGTH: 29
<212> TYPE: DNA
<213> ORGANISM: Artificial
<220> FEATURE:
<223> OTHER INFORMATION: Synthetic; Mir495 Template

<400> SEQUENCE: 6
gaagttgccc atgttatttt cgattaaaa                    29

<210> SEQ ID NO 7
<211> LENGTH: 17
<212> TYPE: DNA
<213> ORGANISM: Artificial
<220> FEATURE:
<223> OTHER INFORMATION: Synthetic; UF

<400> SEQUENCE: 7
gggttcccta agggttg                                 17

<210> SEQ ID NO 8
<211> LENGTH: 20
<212> TYPE: DNA
<213> ORGANISM: Artificial
<220> FEATURE:
<223> OTHER INFORMATION: Synthetic; UR

<400> SEQUENCE: 8
gtgccagcaa gatccaatct                              20

<210> SEQ ID NO 9
<211> LENGTH: 17
<212> TYPE: DNA
<213> ORGANISM: Artificial
<220> FEATURE:
<223> OTHER INFORMATION: Synthetic; Biotin-UF; 5' Biotin modification

<400> SEQUENCE: 9
gggttcccta agggttg                                                17

<210> SEQ ID NO 10
<211> LENGTH: 20
<212> TYPE: DNA
<213> ORGANISM: Artificial
<220> FEATURE:
<223> OTHER INFORMATION: Synthetic; FITC-UR; 5' Fluorescein modification

<400> SEQUENCE: 10
gtgccagcaa gatccaatct                                             20

<210> SEQ ID NO 11
<211> LENGTH: 46
<212> TYPE: DNA
<213> ORGANISM: Artificial
<220> FEATURE:
<223> OTHER INFORMATION: Synthetic; LHIV-G Probe;
    5' Biotin modification;
    3' phosphorothioate/thiophosphate modification

<400> SEQUENCE: 11
gggttcccta agggttggtt tagcatggtg tttaaatctt gtgggg                46

<210> SEQ ID NO 12
<211> LENGTH: 48
<212> TYPE: DNA
<213> ORGANISM: Artificial
<220> FEATURE:
<223> OTHER INFORMATION: Synthetic; LHIV-A Probe; 3' Fluorescein
    modification
<220> FEATURE:
<221> NAME/KEY: misc_feature
<222> LOCATION: (1)..(1)
<223> OTHER INFORMATION: n = Amino-deoxyThymidine

<400> SEQUENCE: 12
nggctccttc tgataatgct gaaaacatag attggatctt gctggcac              48

<210> SEQ ID NO 13
<211> LENGTH: 57
<212> TYPE: DNA
<213> ORGANISM: Artificial
<220> FEATURE:
<223> OTHER INFORMATION: Synthetic; LHIV-1 Template

<400> SEQUENCE: 13
atgttttcag cattatcaga aggagccacc ccacaagatt taaacaccat gctaaac    57

<210> SEQ ID NO 14
<211> LENGTH: 56
<212> TYPE: DNA
<213> ORGANISM: Artificial
<220> FEATURE:
<223> OTHER INFORMATION: Synthetic; LHIV-1D Template

<400> SEQUENCE: 14
atgttttcag cattatcaga aggagccacc cacaagattt aaacaccatg ctaaac     56

```
<210> SEQ ID NO 15
<211> LENGTH: 17
<212> TYPE: DNA
<213> ORGANISM: Artificial
<220> FEATURE:
<223> OTHER INFORMATION: Synthetic; UF

<400> SEQUENCE: 15
gggttcccta agggttg                                                   17

<210> SEQ ID NO 16
<211> LENGTH: 20
<212> TYPE: DNA
<213> ORGANISM: Artificial
<220> FEATURE:
<223> OTHER INFORMATION: Synthetic; UR

<400> SEQUENCE: 16
gtgccagcaa gatccaatct                                                20

<210> SEQ ID NO 17
<211> LENGTH: 17
<212> TYPE: DNA
<213> ORGANISM: Artificial
<220> FEATURE:
<223> OTHER INFORMATION: Synthetic; Biotin-UF; 5' Biotin modification

<400> SEQUENCE: 17
gggttcccta agggttg                                                   17

<210> SEQ ID NO 18
<211> LENGTH: 20
<212> TYPE: DNA
<213> ORGANISM: Artificial
<220> FEATURE:
<223> OTHER INFORMATION: Synthetic; FITC-UR; 5' Fluorescein modification

<400> SEQUENCE: 18
gtgccagcaa gatccaatct                                                20

<210> SEQ ID NO 19
<211> LENGTH: 77
<212> TYPE: DNA
<213> ORGANISM: Artificial
<220> FEATURE:
<223> OTHER INFORMATION: Synthetic; G;
      5' Biotin modification; 3' Chemical modification

<400> SEQUENCE: 19
aatgcggatg cggatgccga ctcgtcatga tgactggtgc caacccttag ggaaccctcg    60
gcatccgcat ccgcatt                                                   77

<210> SEQ ID NO 20
<211> LENGTH: 80
<212> TYPE: DNA
<213> ORGANISM: Artificial
<220> FEATURE:
<223> OTHER INFORMATION: Synthetic; A; 5' Chemical modification

<400> SEQUENCE: 20
cgcatccggg tcctcagcgt gtgccagcaa gatccaatct attgcgtatg tcggtgcctg    60
acgctgagga cccggatgcg                                                80
```

```
<210> SEQ ID NO 21
<211> LENGTH: 40
<212> TYPE: DNA
<213> ORGANISM: Artificial
<220> FEATURE:
<223> OTHER INFORMATION: Synthetic; FIP

<400> SEQUENCE: 21
aatgcggatg cggatgccga ctcgtcatga tgactggtgc                              40

<210> SEQ ID NO 22
<211> LENGTH: 40
<212> TYPE: DNA
<213> ORGANISM: Artificial
<220> FEATURE:
<223> OTHER INFORMATION: Synthetic; BIP

<400> SEQUENCE: 22
cgcatccggg tcctcagcgt caggcaccga catacgcaat                              40

<210> SEQ ID NO 23
<211> LENGTH: 17
<212> TYPE: DNA
<213> ORGANISM: Artificial
<220> FEATURE:
<223> OTHER INFORMATION: Synthetic; LF; 5' Biotin modification

<400> SEQUENCE: 23
gggttcccta agggttg                                                      17

<210> SEQ ID NO 24
<211> LENGTH: 20
<212> TYPE: DNA
<213> ORGANISM: Artificial
<220> FEATURE:
<223> OTHER INFORMATION: Synthetic; LB; ; 5' Fluorescein modification

<400> SEQUENCE: 24
gtgccagcaa gatccaatct                                                   20

<210> SEQ ID NO 25
<211> LENGTH: 17
<212> TYPE: DNA
<213> ORGANISM: Artificial
<220> FEATURE:
<223> OTHER INFORMATION: Synthetic; F

<400> SEQUENCE: 25
caacccttag ggaccc                                                       17

<210> SEQ ID NO 26
<211> LENGTH: 20
<212> TYPE: DNA
<213> ORGANISM: Artificial
<220> FEATURE:
<223> OTHER INFORMATION: Synthetic; R

<400> SEQUENCE: 26
agattggatc ttgctggcac                                                   20

<210> SEQ ID NO 27
<211> LENGTH: 46
<212> TYPE: DNA
<213> ORGANISM: Artificial
<220> FEATURE:
<223> OTHER INFORMATION: Synthetic; Nfo probe; 5' Fluorescein
      modification
```

```
<220> FEATURE:
<221> NAME/KEY: misc_feature
<222> LOCATION: (29)..(29)
<223> OTHER INFORMATION: n is g
<220> FEATURE:
<221> NAME/KEY: misc_feature
<222> LOCATION: (30)..(30)
<223> OTHER INFORMATION: n = g
<220> FEATURE:
<221> NAME/KEY: misc_feature
<222> LOCATION: (29)..(30)
<223> OTHER INFORMATION: Abasic site/spacer modification
<220> FEATURE:
<221> NAME/KEY: misc_feature
<222> LOCATION: (46)..(46)
<223> OTHER INFORMATION: n = dideoxyThymidine

<400> SEQUENCE: 27
caatctatgt tttcagcatt atcagaagnn ccaccccaca agattn           46

<210> SEQ ID NO 28
<211> LENGTH: 31
<212> TYPE: DNA
<213> ORGANISM: Artificial
<220> FEATURE:
<223> OTHER INFORMATION: Synthetic; Forward RPA primer

<400> SEQUENCE: 28
gtgccagcaa gatccaatct atgttttcag c                           31

<210> SEQ ID NO 29
<211> LENGTH: 31
<212> TYPE: DNA
<213> ORGANISM: Artificial
<220> FEATURE:
<223> OTHER INFORMATION: Synthetic; Reverse RPA primer; 5' Biotin
      modification

<400> SEQUENCE: 29
gggttcccta agggttggtt tagcatggtg t                           31

<210> SEQ ID NO 30
<211> LENGTH: 57
<212> TYPE: DNA
<213> ORGANISM: Artificial
<220> FEATURE:
<223> OTHER INFORMATION: Synthetic; LHIV-1
<220> FEATURE:
<221> NAME/KEY: misc_feature
<222> LOCATION: (28)..(28)
<223> OTHER INFORMATION: n = a
<220> FEATURE:
<221> NAME/KEY: misc_feature
<222> LOCATION: (29)..(29)
<223> OTHER INFORMATION: n = c
<220> FEATURE:
<221> NAME/KEY: misc_feature
<222> LOCATION: (28)..(29)
<223> OTHER INFORMATION: probe junction site

<400> SEQUENCE: 30
atgttttcag cattatcaga aggagccnnc ccacaagatt taaacaccat gctaaac     57

<210> SEQ ID NO 31
<211> LENGTH: 57
<212> TYPE: DNA
<213> ORGANISM: Artificial
<220> FEATURE:
<223> OTHER INFORMATION: Synthetic; LHIV-1M
<220> FEATURE:
<221> NAME/KEY: misc_feature
```

-continued

```
<222> LOCATION: (28)..(28)
<223> OTHER INFORMATION: n = a
<220> FEATURE:
<221> NAME/KEY: misc_feature
<222> LOCATION: (29)..(29)
<223> OTHER INFORMATION: n = c
<220> FEATURE:
<221> NAME/KEY: misc_feature
<222> LOCATION: (28)..(29)
<223> OTHER INFORMATION: probe junction site

<400> SEQUENCE: 31
atgttttcag cattatcaga aggagccnnc cgacaagatt taaacaccat gctaaac      57

<210> SEQ ID NO 32
<211> LENGTH: 57
<212> TYPE: DNA
<213> ORGANISM: Artificial
<220> FEATURE:
<223> OTHER INFORMATION: Synthetic; LHIV-1M2
<220> FEATURE:
<221> NAME/KEY: misc_feature
<222> LOCATION: (28)..(28)
<223> OTHER INFORMATION: n = a
<220> FEATURE:
<221> NAME/KEY: misc_feature
<222> LOCATION: (29)..(29)
<223> OTHER INFORMATION: n = g
<220> FEATURE:
<221> NAME/KEY: misc_feature
<222> LOCATION: (28)..(29)
<223> OTHER INFORMATION: probe junction site

<400> SEQUENCE: 32
atgttttcag cattatcaga aggagccnnc ccacaagatt taaacaccat gctaaac      57

<210> SEQ ID NO 33
<211> LENGTH: 57
<212> TYPE: DNA
<213> ORGANISM: Artificial
<220> FEATURE:
<223> OTHER INFORMATION: Synthetic; LHIV-1M3
<220> FEATURE:
<221> NAME/KEY: misc_feature
<222> LOCATION: (28)..(28)
<223> OTHER INFORMATION: n = t
<220> FEATURE:
<221> NAME/KEY: misc_feature
<222> LOCATION: (29)..(29)
<223> OTHER INFORMATION: n = c
<220> FEATURE:
<221> NAME/KEY: misc_feature
<222> LOCATION: (28)..(29)
<223> OTHER INFORMATION: probe junction site

<400> SEQUENCE: 33
atgttttcag cattatcaga aggagccnnc ccacaagatt taaacaccat gctaaac      57

<210> SEQ ID NO 34
<211> LENGTH: 57
<212> TYPE: DNA
<213> ORGANISM: Artificial
<220> FEATURE:
<223> OTHER INFORMATION: Synthetic; LHIV-1M4
<220> FEATURE:
<221> NAME/KEY: misc_feature
<222> LOCATION: (28)..(28)
<223> OTHER INFORMATION: n = t
<220> FEATURE:
<221> NAME/KEY: misc_feature
<222> LOCATION: (29)..(29)
<223> OTHER INFORMATION: n = c
<220> FEATURE:
```

```
<221> NAME/KEY: misc_feature
<222> LOCATION: (28)..(29)
<223> OTHER INFORMATION: probe junction site

<400> SEQUENCE: 34
atgttttcag cattatcaga aggagcannc ccacaagatt taaacaccat gctaaac    57

<210> SEQ ID NO 35
<211> LENGTH: 57
<212> TYPE: DNA
<213> ORGANISM: Artificial
<220> FEATURE:
<223> OTHER INFORMATION: Synthetic; LHIV-1M5
<220> FEATURE:
<221> NAME/KEY: misc_feature
<222> LOCATION: (28)..(28)
<223> OTHER INFORMATION: n = a
<220> FEATURE:
<221> NAME/KEY: misc_feature
<222> LOCATION: (29)..(29)
<223> OTHER INFORMATION: n = c
<220> FEATURE:
<221> NAME/KEY: misc_feature
<222> LOCATION: (28)..(29)
<223> OTHER INFORMATION: probe junction site

<400> SEQUENCE: 35
atgttttcag cattatcaga aggagacnnc ccacaagatt taaacaccat gctaaac    57

<210> SEQ ID NO 36
<211> LENGTH: 57
<212> TYPE: DNA
<213> ORGANISM: Artificial
<220> FEATURE:
<223> OTHER INFORMATION: Synthetic; LHIV-1M6
<220> FEATURE:
<221> NAME/KEY: misc_feature
<222> LOCATION: (28)..(28)
<223> OTHER INFORMATION: n = a
<220> FEATURE:
<221> NAME/KEY: misc_feature
<222> LOCATION: (29)..(29)
<223> OTHER INFORMATION: n = c
<220> FEATURE:
<221> NAME/KEY: misc_feature
<222> LOCATION: (28)..(29)
<223> OTHER INFORMATION: probe junction site

<400> SEQUENCE: 36
atgttttcag cattatcaga aggatacnnc ccacaagatt taaacaccat gctaaac    57

<210> SEQ ID NO 37
<211> LENGTH: 40
<212> TYPE: DNA
<213> ORGANISM: Artificial
<220> FEATURE:
<223> OTHER INFORMATION: Synthetic; FLUA1-G;
    3' phosphorothioate/thiophosphate modification

<400> SEQUENCE: 37
gggttcccta agggttgcat tttggacaaa gcgtctacgc                        40

<210> SEQ ID NO 38
<211> LENGTH: 38
<212> TYPE: DNA
<213> ORGANISM: Artificial
<220> FEATURE:
<223> OTHER INFORMATION: Synthetic; FLUA1-A; 3' Fluorescein modification
<220> FEATURE:
<221> NAME/KEY: misc_feature
<222> LOCATION: (1)..(1)
```

<223> OTHER INFORMATION: n = Amino-deoxyThymidine

<400> SEQUENCE: 38
ngcagtcctc gctcactgag attggatctt gctggcac    38

<210> SEQ ID NO 39
<211> LENGTH: 44
<212> TYPE: DNA
<213> ORGANISM: Artificial
<220> FEATURE:
<223> OTHER INFORMATION: Synthetic; FLUA1-WT
<220> FEATURE:
<221> NAME/KEY: misc_feature
<222> LOCATION: (20)..(20)
<223> OTHER INFORMATION: n = a
<220> FEATURE:
<221> NAME/KEY: misc_feature
<222> LOCATION: (21)..(21)
<223> OTHER INFORMATION: n = g
<220> FEATURE:
<221> NAME/KEY: misc_feature
<222> LOCATION: (20)..(21)
<223> OTHER INFORMATION: probe junction site

<400> SEQUENCE: 39
cccagtgagc gaggactgcn ncgtagacgc tttgtccaaa atgc    44

<210> SEQ ID NO 40
<211> LENGTH: 44
<212> TYPE: DNA
<213> ORGANISM: Artificial
<220> FEATURE:
<223> OTHER INFORMATION: Synthetic; FLUA1-M1
<220> FEATURE:
<221> NAME/KEY: misc_feature
<222> LOCATION: (20)..(20)
<223> OTHER INFORMATION: n = a
<220> FEATURE:
<221> NAME/KEY: misc_feature
<222> LOCATION: (21)..(21)
<223> OTHER INFORMATION: n = g
<220> FEATURE:
<221> NAME/KEY: misc_feature
<222> LOCATION: (20)..(21)
<223> OTHER INFORMATION: probe junction site

<400> SEQUENCE: 40
cccagtgagc gaggactacn ncgtagacgc tttgtccaaa atgc    44

<210> SEQ ID NO 41
<211> LENGTH: 44
<212> TYPE: DNA
<213> ORGANISM: Artificial
<220> FEATURE:
<223> OTHER INFORMATION: Synthetic; FLUA1-M2
<220> FEATURE:
<221> NAME/KEY: misc_feature
<222> LOCATION: (20)..(20)
<223> OTHER INFORMATION: n = a
<220> FEATURE:
<221> NAME/KEY: misc_feature
<222> LOCATION: (21)..(21)
<223> OTHER INFORMATION: n = g
<220> FEATURE:
<221> NAME/KEY: misc_feature
<222> LOCATION: (20)..(21)
<223> OTHER INFORMATION: probe junction site

<400> SEQUENCE: 41
cccagtgagc gaggacgacn ncgtagacgc tttgtccaaa atgc    44

```
<210> SEQ ID NO 42
<211> LENGTH: 44
<212> TYPE: DNA
<213> ORGANISM: Artificial
<220> FEATURE:
<223> OTHER INFORMATION: Synthetic; FLUA1-M3
<220> FEATURE:
<221> NAME/KEY: misc_feature
<222> LOCATION: (20)..(20)
<223> OTHER INFORMATION: n = a
<220> FEATURE:
<221> NAME/KEY: misc_feature
<222> LOCATION: (21)..(21)
<223> OTHER INFORMATION: n = g
<220> FEATURE:
<221> NAME/KEY: misc_feature
<222> LOCATION: (20)..(21)
<223> OTHER INFORMATION: probe junction site

<400> SEQUENCE: 42
cccagtgagc gaggaggacn ncgtagacgc tttgtccaaa atgc          44

<210> SEQ ID NO 43
<211> LENGTH: 44
<212> TYPE: DNA
<213> ORGANISM: Artificial
<220> FEATURE:
<223> OTHER INFORMATION: Synthetic; FLUA1-K1
<220> FEATURE:
<221> NAME/KEY: misc_feature
<222> LOCATION: (20)..(20)
<223> OTHER INFORMATION: n = a
<220> FEATURE:
<221> NAME/KEY: misc_feature
<222> LOCATION: (21)..(21)
<223> OTHER INFORMATION: n = c
<220> FEATURE:
<221> NAME/KEY: misc_feature
<222> LOCATION: (20)..(21)
<223> OTHER INFORMATION: probe junction site

<400> SEQUENCE: 43
cccagtgagc gaggactgcn ncgtagacgc tttgtccaaa atgc          44
```